United States Patent
Dininno et al.

(10) Patent No.: US 6,277,843 B1
(45) Date of Patent: Aug. 21, 2001

(54) CARBAPENEM ANTIBACTERIAL COMPOUNDS, COMPOSITIONS CONTAINING SUCH COMPOUNDS AND METHODS OF TREATMENT

(75) Inventors: Frank P. Dininno, Old Bridge; Helen Chen, Livingston, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/421,078

(22) Filed: Oct. 19, 1999

Related U.S. Application Data

(63) Continuation of application No. 09/133,196, filed on Aug. 13, 1998, now abandoned.
(60) Provisional application No. 60/059,111, filed on Sep. 17, 1997.

(51) Int. Cl.⁷ .................. C07D 477/14; A61K 31/407; A61K 31/4995; A61K 31/4178; A61P 31/04
(52) U.S. Cl. ........................ 514/210.09; 540/302
(58) Field of Search .................. 540/302; 514/210.09

(56) References Cited

U.S. PATENT DOCUMENTS

| | | | |
|---|---|---|---|
| 4,309,438 | 1/1982 | Christensen et al. | 424/274 |
| 4,479,947 | 10/1984 | Christensen | 424/203 |

FOREIGN PATENT DOCUMENTS

| | | |
|---|---|---|
| 0 007614 | 2/1980 | (EP) . |
| 0 072 014 | 2/1983 | (EP) . |
| 0 480 715 A1 | 4/1992 | (EP) . |

OTHER PUBLICATIONS

S. M. Schmitt Et Al., *J. Antibiotic* 41(6) p 780–787 (1988).
W. M. Stanley, *J. Am Chem Soc.* 55, p 706 (1933).

*Primary Examiner*—Mark L Berch
(74) *Attorney, Agent, or Firm*—Sylvia A. Ayler; Mark R. Daniel

(57) ABSTRACT

The present invention relates to carbapenem antibacterial agents of the formula I:

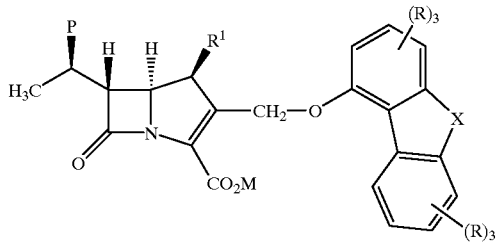

as well as salts and hydrates thereof. Pharmaceutical compositions and methods of treatment are also included wherein X is present or absent, when present, represents a members selected from the group consisting of:

$CH_2$, $C(R)_2$, $C=CR_2$, O, $S(O)x$, with x equal to 0, 1 or 2; C(O), C(O)O, OC(O) and NR—.

14 Claims, No Drawings

CARBAPENEM ANTIBACTERIAL COMPOUNDS, COMPOSITIONS CONTAINING SUCH COMPOUNDS AND METHODS OF TREATMENT

This application claims the benefit of U.S. Provisional Application No. 60/059,111, filed Sep. 17, 1997, and is continuation of U.S. Ser. No. 09/133,196, filed Aug. 13, 1998 abandoned.

BACKGROUND OF THE INVENTION

The present invention relates to carbapenem antibacterial agents in which the carbapenem nucleus is substituted at the 2-position with an aryl platform, linked through a $CH_2$—O— group. The aryl platform is further substituted with various substituent groups, typically including at least one cationic group The carbapenems of the present invention are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy for treating infections caused by these difficult to control pathogens.

There is an increasing need for agents effective against such pathogens (MRSA/MRCNS) which are at the same time relatively free from undesirable side effects.

SUMMARY OF THE INVENTION

The present invention relates to a compound represented by formula I:

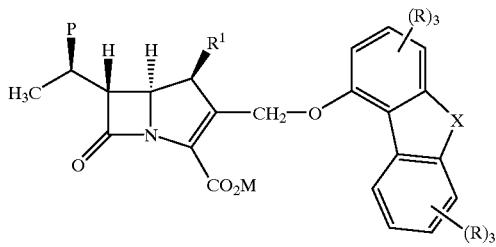

I or a salt or hydrate thereof, wherein:

$R^1$ represents H or methyl;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

X is present or absent, and when present, represents members selected from the group consisting of: $CH_2$, $C(R)_2$, $C=CR_2$, O, $S(O)x$, with x equal to 0, 1 or 2, $C(O)$, $CO_2$, OCO and NR;

each R group is independently selected from: hydrogen; halo; —CN; —$N_2$; —$NR^aR^b$; —$OR^c$; —$SR^c$; —C(O)$NR^aR^b$; —C(O)$OR^h$; —S(O)$R^c$; —$SO_2R^c$; —$SO_2NR^aR^b$; —$NR^aSO_2R^b$; —C(O)$R^a$; —OC(O)$R^a$; —OC(O)$NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; —A—$(CH_2)_n$—Q and —$C_{3-7}$ cycloalkyl, unsubstituted or substituted with one to four $R^d$ groups;

A represents O, S or —$CH_2$—;

n represents an integer 0–3;

each $R^a$, $R^b$ and $R^c$ independently represents hydrogen, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$ or —$NR^eC(NR^f)R^g$;

$R^e$, $R^f$ and $R^g$ represent hydrogen; —R*; —$C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3-C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

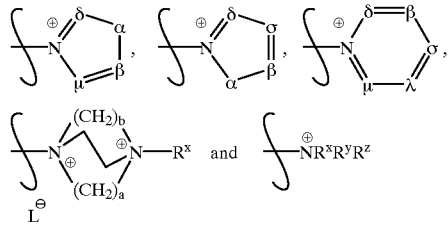

wherein:

a and b are 1, 2 or 3;

L- is a pharmaceutically acceptable counterion;

α represents O, S or $NR^s$;

β, δ, λ, μ and σ represent $CR^t$, N or $N^+R^s$, provided that no more than one of β, δ, λ, μ and σ is $N^+R^s$;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —NO$_2$; —NR"R$^v$; —OR"; —SR"; —CONR"R$^v$; —COOR$^h$; —SOR"; —SO$_2$R"; —SO$_2$NR"R$^v$; —NR"SO$_2$R$^v$; —COR"; —NR"COR$^v$; —OCOR"; —OCONR"R$^v$; —NR"CO$_2$R$^v$; —NR"CONR$^v$R$^w$; —OCO$_2$R$^v$; —C$_{1-6}$ straight- or branched chain alkyl, unsubstituted or substituted with one to four R$^i$ groups;

R" and R$^v$ represent hydrogen or —C$_{1-6}$ straight- or branched-chain alkyl, unsubstituted or substituted with one to four R$^i$ groups;

or R" and R$^v$ together with any intervening atoms represent a 4–6 membered saturated ring optionally interrupted by one or more of O, S, NR$^w$ or —C(O)—, said ring being unsubstituted or substituted with one to four R$^i$ groups;

each R$^w$ independently represents hydrogen; —C$_{1-6}$ straight- or branched chain alkyl, unsubstituted or substituted with one to four R$^i$ groups; C$_{3-6}$ cycloalkyl optionally substituted with one to four R$^i$ groups; phenyl optionally substituted with one to four R$^i$ groups, or heteroaryl optionally substituted with 1–4 R$^i$ groups;

or R$^h$ and R$^w$ taken together with any intervening atoms represent a 5–6 membered saturated ring, optionally interrupted by one or two of O, S, SO$_2$, NH or NCH$_3$;

R$^x$ represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

R$^y$ and R$^z$ represent hydrogen; phenyl; —C$_{1-6}$ straight or branched chain alkyl, unsubstituted or substituted with one to four R$^i$ groups, and optionally interrupted by O, S, NR$^w$, N$^+$R$^h$R$^w$ or —C(O)—;

or R$^x$ and R$^y$ together with any intervening atoms represent a 4–6 membered saturated ring optionally interrupted by O, S, SO$_2$, NR$^w$, N$^+$R$^h$R$^w$ or —C(O)—, unsubstituted or substituted with 1–4 R$^i$ groups, and when R$^x$ and R$^y$ together represent a 4–6 membered ring as defined above, R$^z$ is as defined above or R$^z$ represents an additional saturated 4–6 membered ring fused to the ring represented by R$^x$ and R$^y$ taken together, optionally interrupted by O, S, NR$^w$ or —C(O)—, said rings being unsubstituted or substituted with one to four R$^i$ groups.

Pharmaceutical compositions and methods of treatment are also included.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from R$^d$ and R$^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

  

pyrrole (pyrrolyl)  imidazole (imidazolyl)  thiazole (thiazolyl)

  

oxazole (oxazolyl)  furan (furyl)  thiophene (thienyl)

  

triazole (triazolyl)  pyrazole (pyrazolyl)  isoxazole (isoxazolyl)

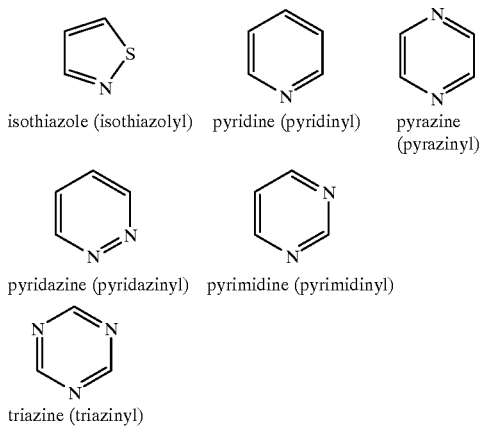

Heteroarylium refers to heteroaryl groups bearing a quaternary nitrogen atom and thus a positive charge. Examples include the following:

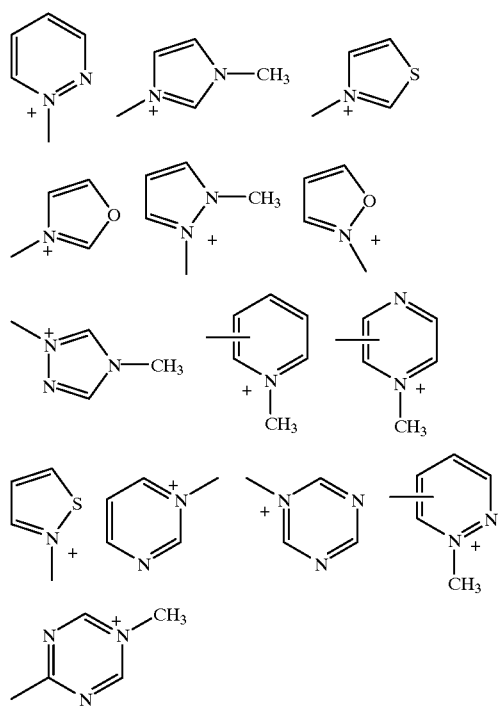

When a charge is shown on a particular nitrogen atom in a ring which contains one or more additional nitrogen atoms, it is understood that the charge may reside on a different nitrogen atom in the ring by virtue of charge resonance that occurs.

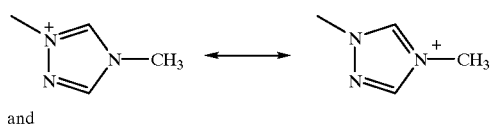
and

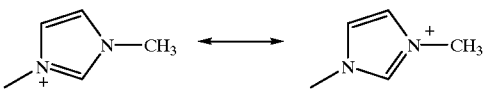

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

Guanidinyl refers to the group: $H_2NC(NH)NH$—.
Carbamimidoyl refers to the group: $H_2NC(NH)$—.
Ureido refers to the group: $H_2NC(O)NH$—.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

When a group is "optionally interrupted", this includes one or more of the interrupting moieties in combination, as well as said moieties located at either or both ends of the chain. Thus, it includes terminating the group as well.

In some of the carbapenem compounds of the present invention, M is a readily removable carboxyl protecting group, and/or P represents a hydroxyl which is protected by a hydroxyl-protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

Examples of suitable C-6 hydroxyethyl protecting groups include triethylsilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group).

The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intestinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

$L^-$ can be present or absent as necessary to maintain the appropriate charge balance. When present, $L^-$ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when $L^-$ represents a specie with more than one negative charge, such as malonate, tartrate or ethylenediaminetetraacetate (EDTA), an appropriate number of carbapenem molecules can be found in association therewith to maintain the overall charge balance and neutrality.

When the side chain is neutral, and the 3-carboxylate is in the form of an anion, the molecule is charge balanced by the presence of an appropriately charged group, such as $L^+$. Suitable positively charged groups include cations, such as sodium, potassium, calcium, magnesium and the like. Protonated moieties are also acceptable, such as tetraalkylammonium and the like.

A subset of compounds of the invention which is of particular interest is described with reference to formula I wherein $R^1$ represents methyl. Within this subset, all other variables are as originally defined.

Another subset of compounds of the invention which is of particular interest is described with reference to formula I wherein $CO_2M$ represents a carboxylic acid or a carboxylate anion. Hence, M in this instance represents a negative charge which will be balanced by a positively charged group, such as in the positively charged R group. Likewise, if the positively charged R group contains more than one positive charge, a negatively charged counterion may be present which in combination with the carboxylate anion, provides overall charge neutrality.

Another subset of compounds of the invention which is of particular interest is described with reference to formula I wherein P represents hydroxyl or hydroxyl protected by hydroxyl-protecting group. Within this subset, all other variables are as originally defined.

Another subset of compounds of the invention which is particular interest is described with reference to formula I wherein at least one of the R groups attached to the phenyl ring contains a positively charged moiety. More particularly, one of the R groups represents —A—(CH$_2$)$_n$—Q, and the remaining R groups represent hydrogen or another value of R other than —A—(CH$_2$)$_n$—Q. Within this subset, A, n, Q and all other variables are as originally defined.

Another subset of compounds of the invention which is of particular interest is described with reference to formula I one of the R groups represents —A—(CH$_2$)$_n$—Q, and A represents —CH$_2$—. Within this subset, all other variables are as originally defined.

Another subset of compounds of the invention which is of particular interest is described with reference to formula I wherein one of the R groups represents —A—(CH$_2$)$_n$—Q, and n represents 0 or 1. Within this subset, all other variables are as originally defined.

Another subset of compounds of the invention which is of particular interest is described with reference to formula I wherein one of the R groups represents —A—(CH$_2$)$_n$—Q, and Q represents

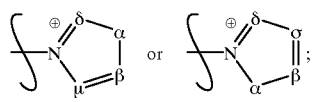

α represents O, S or NR$^s$;

and β, δ, λ, μ and σ represent CR$^t$, N or N$^+$R$^s$, provided that no more than one of β, δ, λ, μ and σ is N$^+$R$^s$, balanced by L$^-$ which is a pharmaceutically acceptable counterion, and R$^s$ is as originally defined. Within this subset, all other variables are as originally defined.

Another subset of compounds of the invention which is of particular interest is described with reference to formula I wherein one of the R groups represents —A—(CH$_2$)$_n$—Q, and Q is selected from the group consisting of:

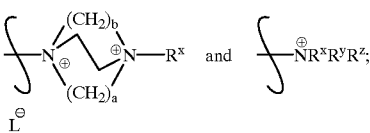

a and b are 2;

L$^-$ is a pharmaceutically acceptable counterion;

and R$^x$, R$^y$ and R$^z$ are as originally defined.

Within this subset, all other variables are as originally defined.

A more preferred subset of compounds of the invention which is of interest is described with reference to formula I wherein one of the R groups represents —A—(CH$_2$)$_n$—Q, and Q is

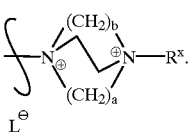

Within this subset, all other variables are as originally defined.

Another subset of compounds of the invention which is of particular interest is described with reference to formula I wherein one of the R groups represents —A—(CH$_2$)$_n$—Q, and Q is

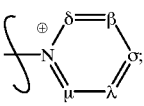

wherein:

α represents O, S or NR$^s$;

β, δ, λ, μ and σ represent CR$^t$, N or N$^+$R$^s$, provided that no more than one of β, δ, λ, μ and σ is N$^+$R$^s$, balanced by L$^-$, which is a pharmaceutically acceptable counterion, and all other variables are as originally defined.

Representative examples of compounds of the invention are as follows:

TABLE 1

| Cpd No. | Compound |
| --- | --- |
| 2 | |

TABLE 1-continued
| Cpd No. | Compound |
|---|---|
| 3 | 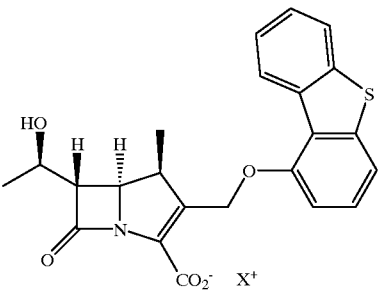 |
| 4 | 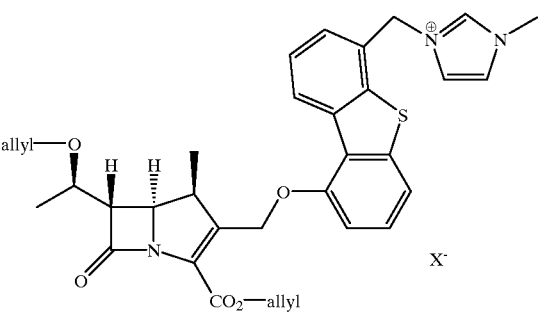 |
| 5 | 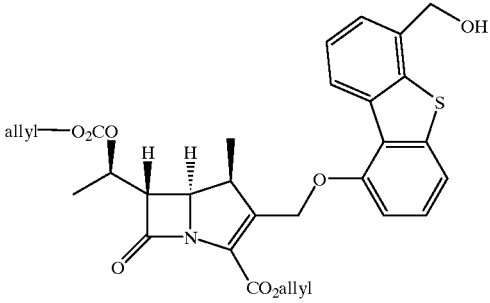 |
| 6 | 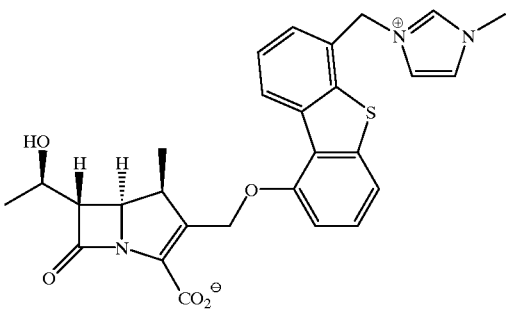 |

TABLE 1-continued

| Cpd No. | Compound |
|---|---|
| 7 | (structure) |
| 8 | (structure) |
| 9 | (structure) |
| 10 | (structure) |

TABLE 1-continued
| Cpd No. | Compound |
|---|---|
| 11 | 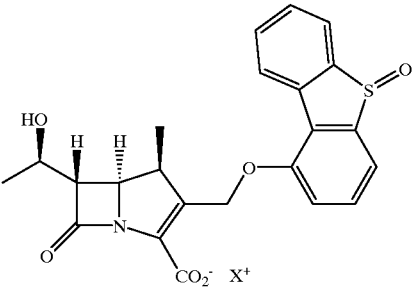 |
| 12 | 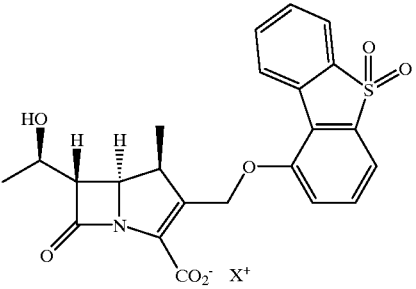 |
| 13 | 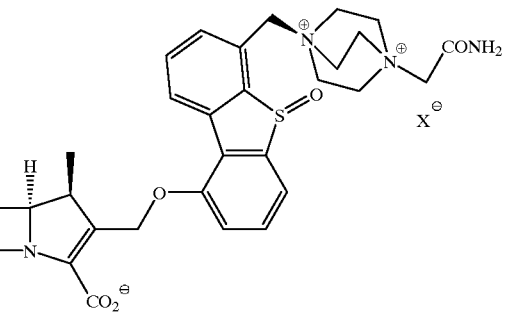 |
| 14 | 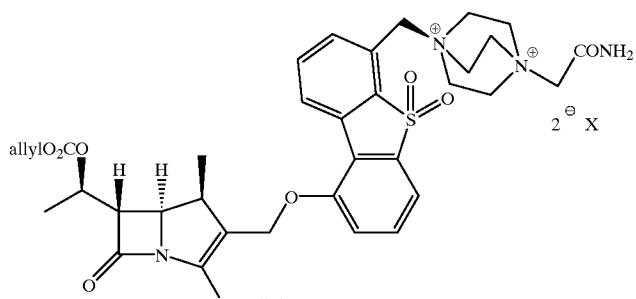 |

TABLE 1-continued
| Cpd No. | Compound |
|---|---|
| 15 | 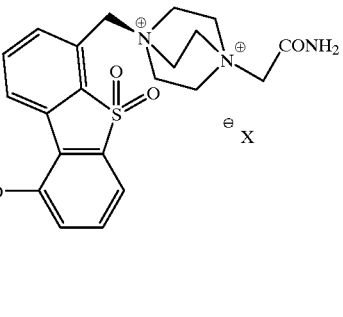 |
| 16 | 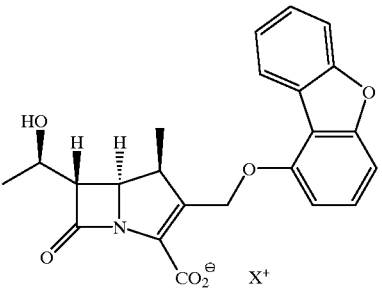 |
| 17 | 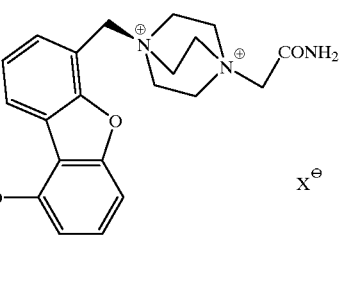 |
| 18 | 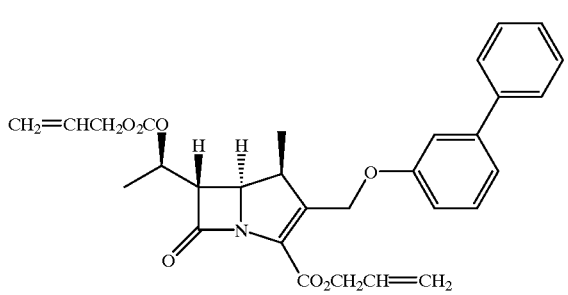 |
| 19 | 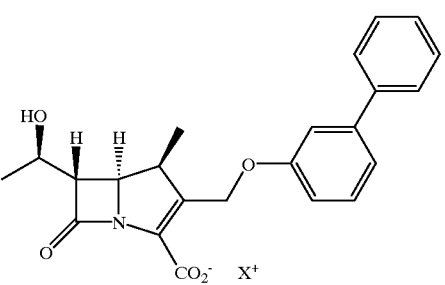 |

TABLE 1-continued
| Cpd No. | Compound |
| --- | --- |
| 20 | 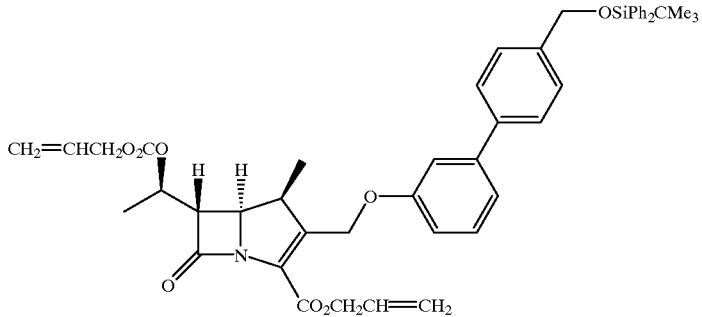 |
| 21 | 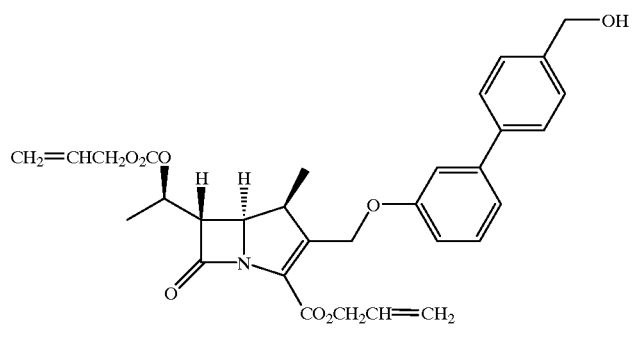 |
| 22 | 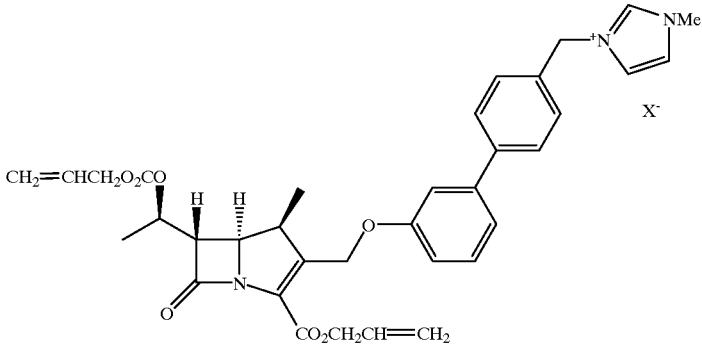 |
| 23 | 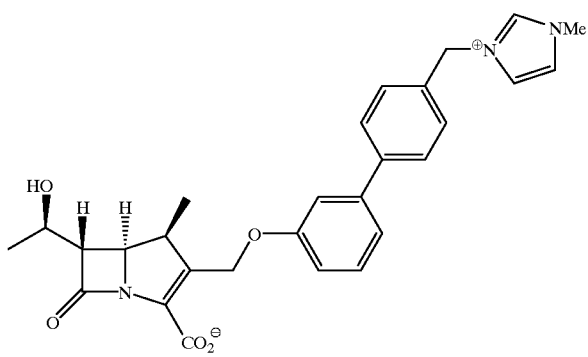 |

TABLE 1-continued
| Cpd No. | Compound |
|---|---|
| 24 | 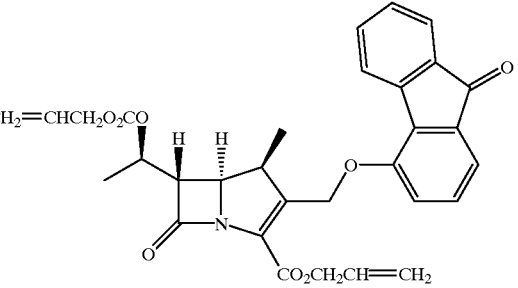 |
| 25 | 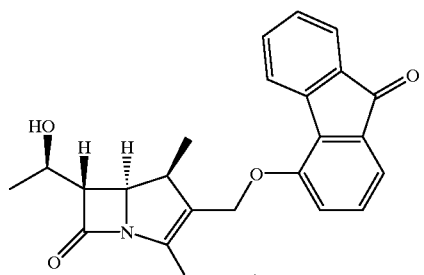 |
| 26 | 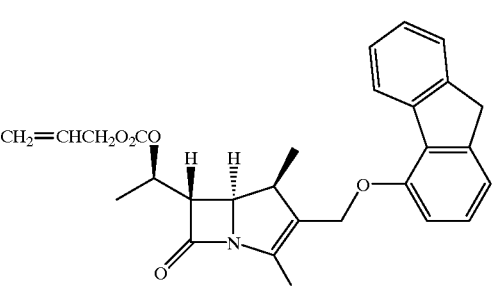 |
| 27 | 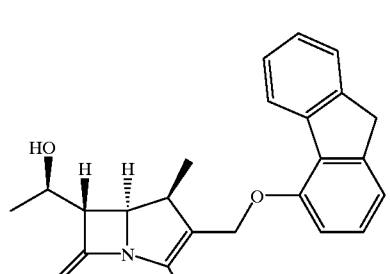 |
| 28 | 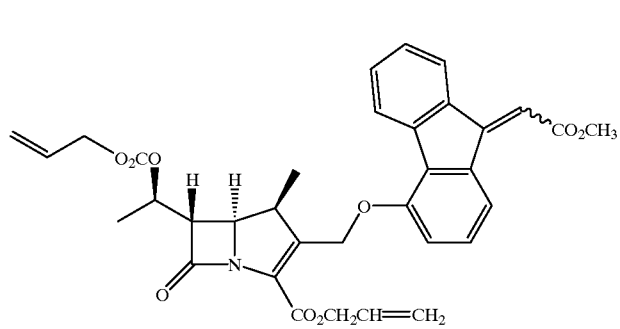 |

TABLE 1-continued
| Cpd No. | Compound |
|---|---|
| 29 | 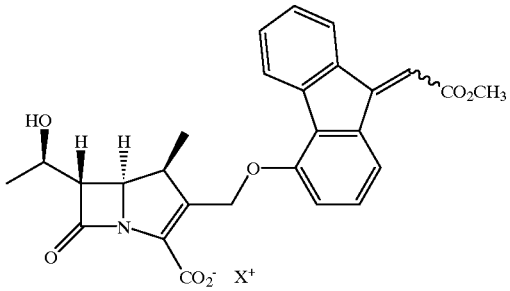 |
| 30 | 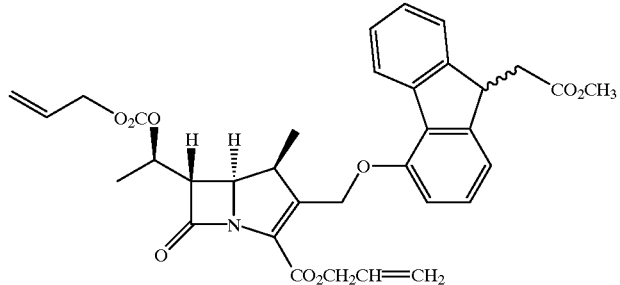 |
| 31 | 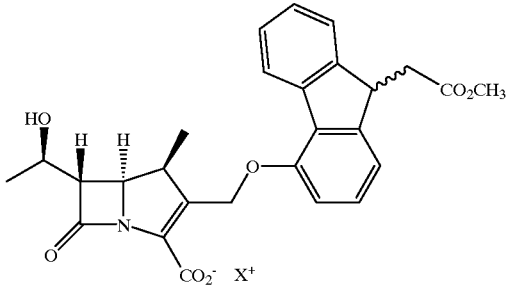 |
| 32 | 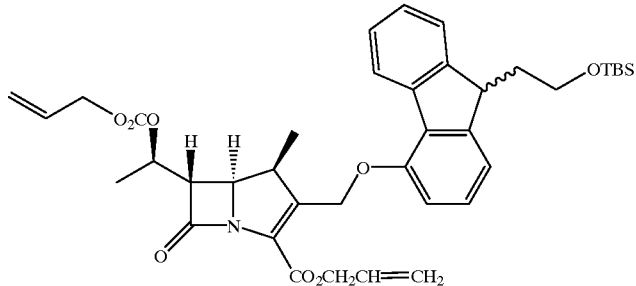 |
| 33 | 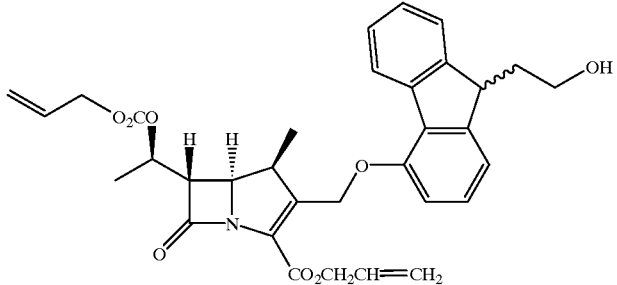 |

TABLE 1-continued
| Cpd No. | Compound |
|---|---|
| 34 | 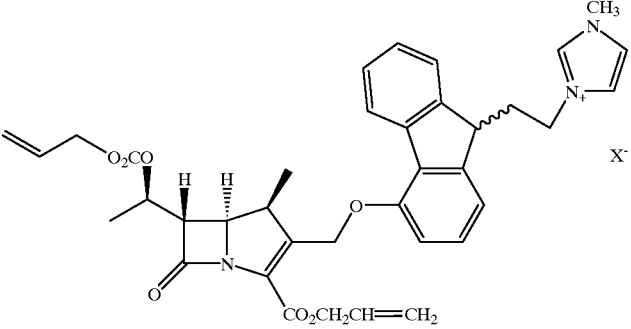 |
| 35 | 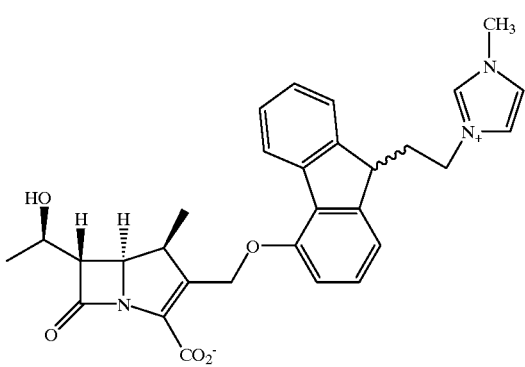 |
| 36 | 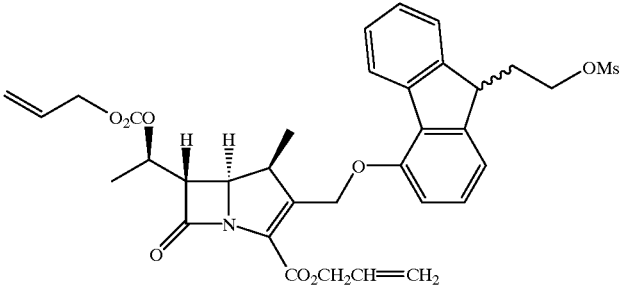 |
| 37 | 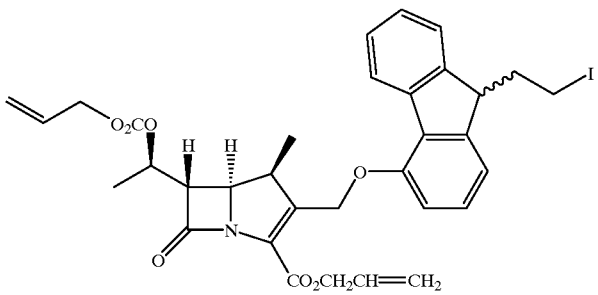 |

TABLE 1-continued
| Cpd No. | Compound |
|---|---|
| 38 | 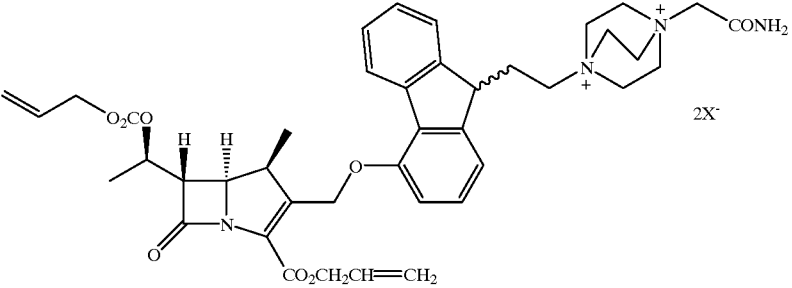 2X⁻ |
| 39 | 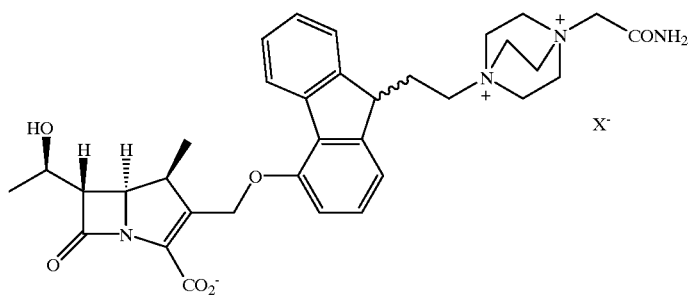 X⁻ |
| 40 | 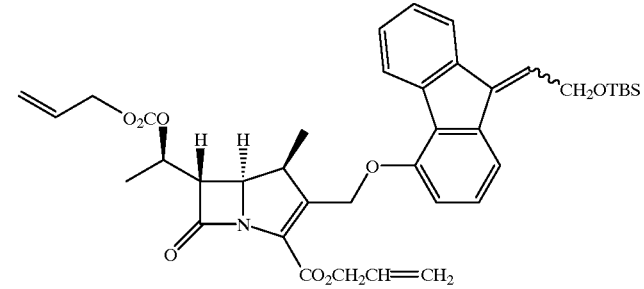 |
| 41 | 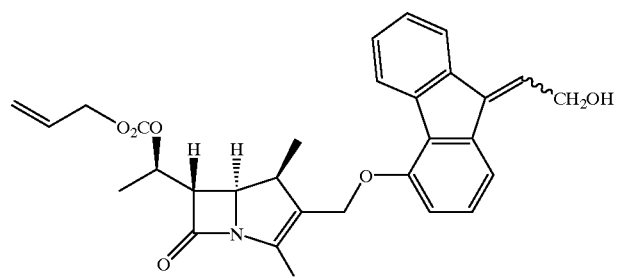 |
| 42 | 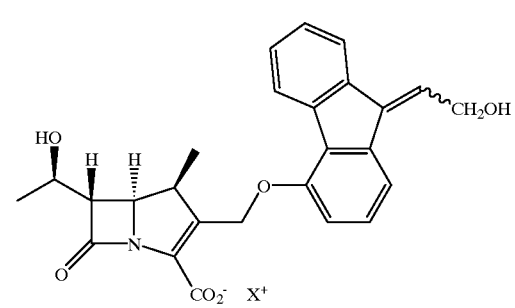 |

TABLE 1-continued

| Cpd No. | Compound |
|---|---|
| 43 | (structure: carbapenem with allyloxycarbonyl group, methyl, CO₂CH₂CH=CH₂, linked via OCH₂ to fluorenone bearing CH₂OTBS) |
| 44 | (structure: same carbapenem core linked to fluorenone bearing CH₂OH) |
| 45 | (structure: same carbapenem core linked to fluorenone bearing CH₂OMs) |
| 46 | (structure: same carbapenem core linked to fluorenone bearing CH₂I) |

TABLE 1-continued

| Cpd No. | Compound |
|---|---|
| 47 | |
| 48 | |
| 49 | |

TABLE 1-continued

| Cpd No. | Compound |
|---------|----------|
| 50 | *(chemical structure)* |
| 51 | *(chemical structure)* |
| 52 | *(chemical structure)* |

TABLE 1-continued
| Cpd No. | Compound |
|---|---|
| 53 | 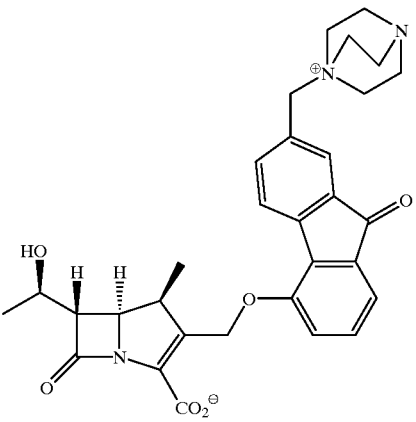 |
| 54 | 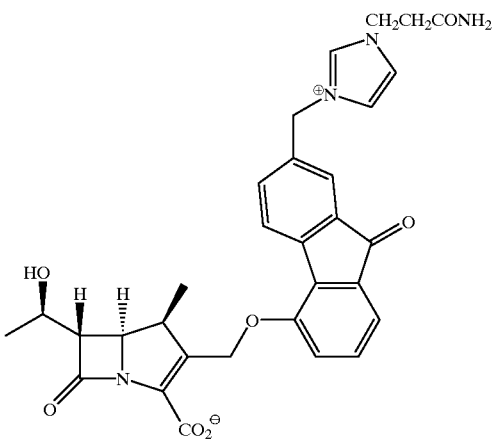 |
| 55 | 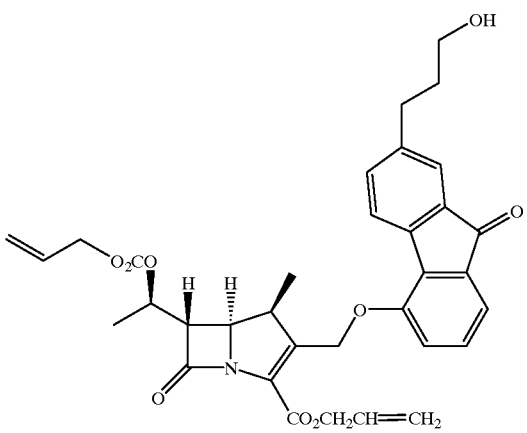 |

TABLE 1-continued
| Cpd No. | Compound |
|---|---|
| 56 | 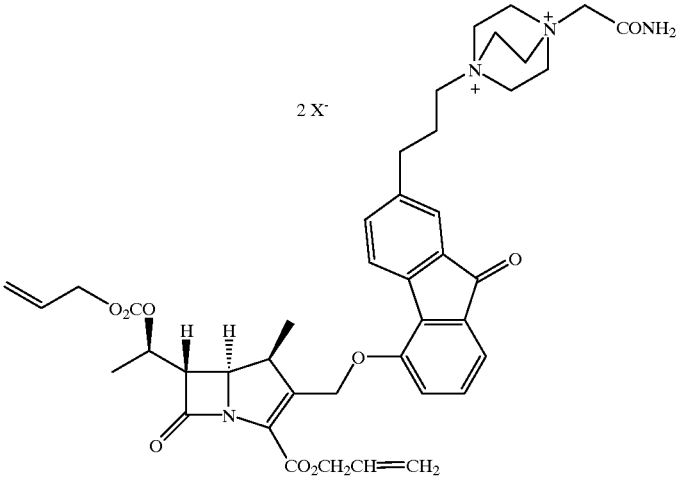 |
| 57 | 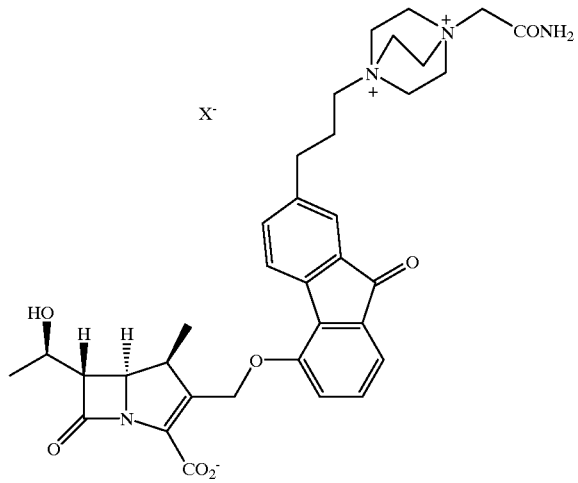 |
| 58 | 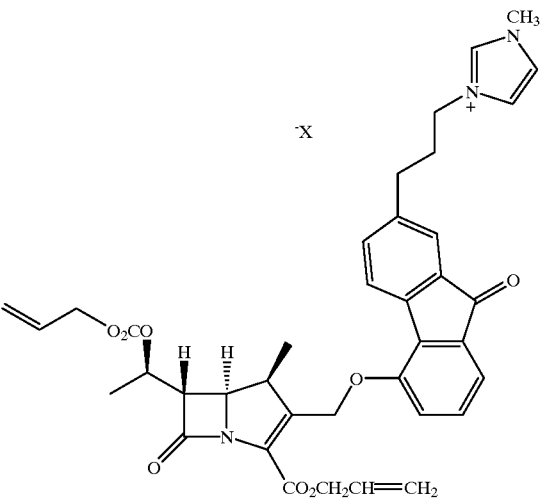 |

TABLE 1-continued
| Cpd No. | Compound |
|---|---|
| 59 | 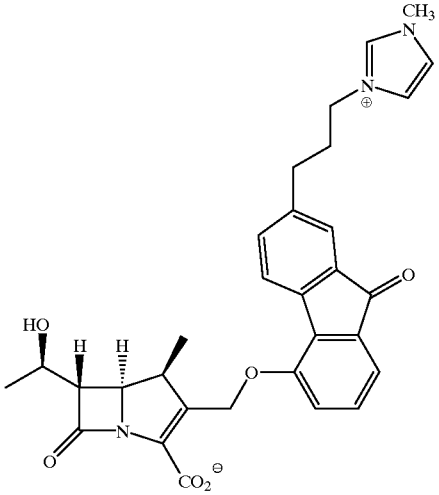 |
| 60 | 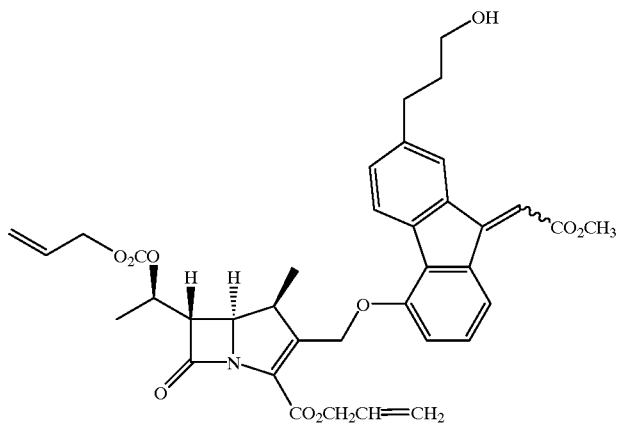 |
| 61 | 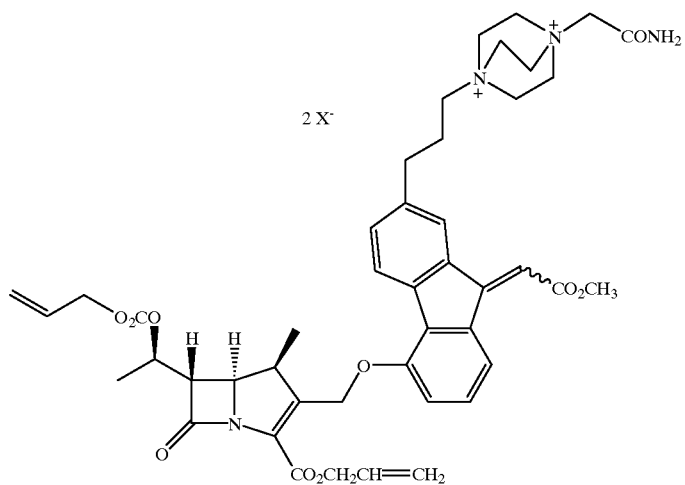 |

TABLE 1-continued
| Cpd No. | Compound |
|---|---|
| 62 | 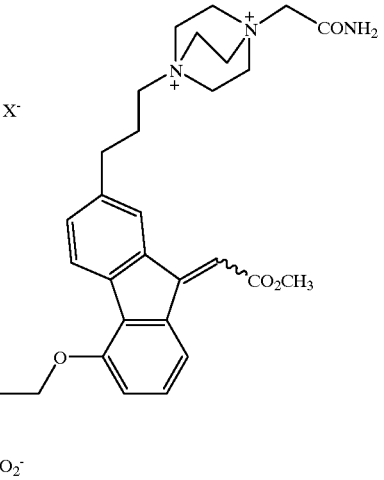 |
| 63 | 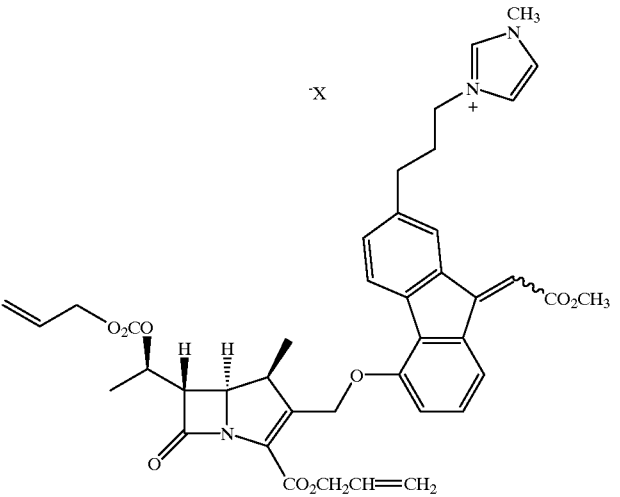 |
| 64 | 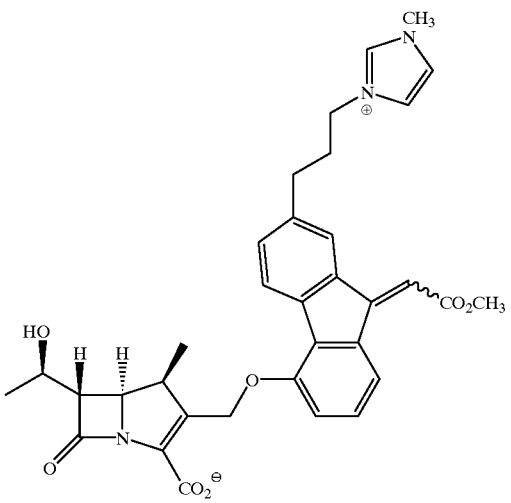 |

TABLE 1-continued

| Cpd No. | Compound |
|---|---|
| 65 | 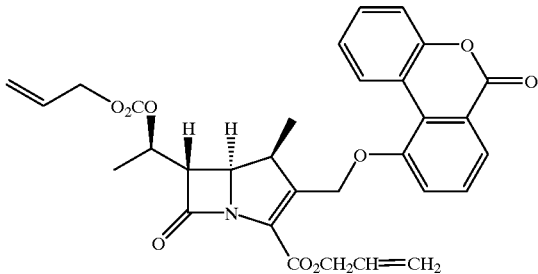 |
| 66 | 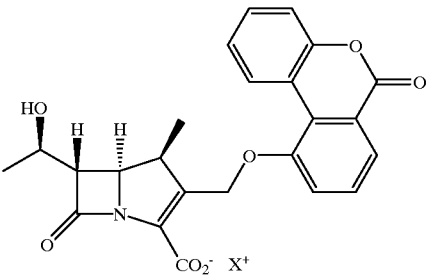 |

$X^+$ and $X^-$ represent appropriately charged counterions which are present to provide overall charge balance.

The compounds of the present invention are prepared by reacting a suitably protected, activated 2-hydroxymethyl-carbapen-2-em-3-carboxylate with an appropriately substituted phenyl ring, and then removing any protecting groups which are present to afford the desired final product. The process is illustrated by the following generic schemes:

FLOW SHEET A

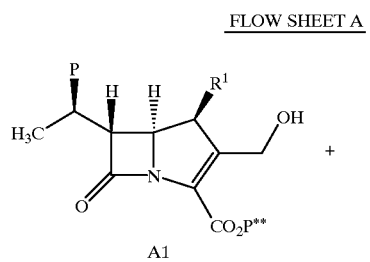

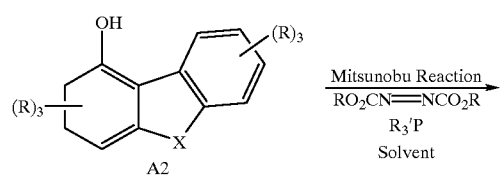

-continued

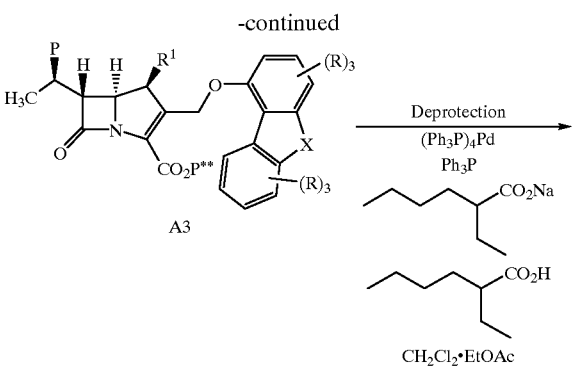

FLOW SHEET B

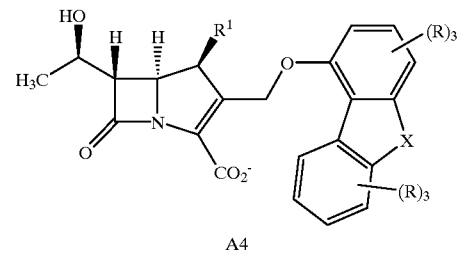

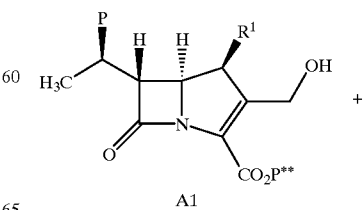

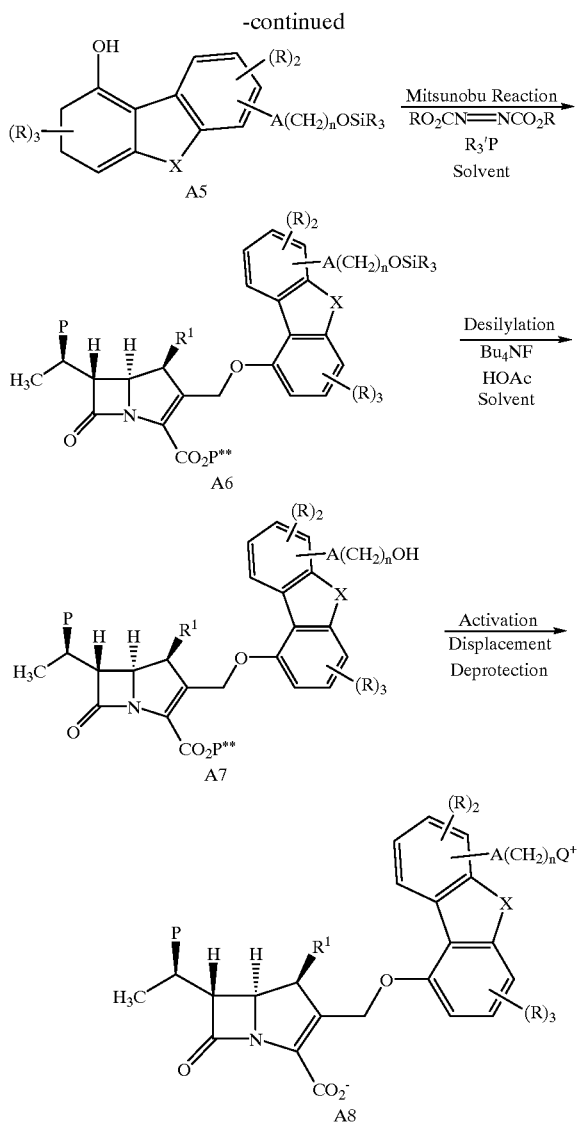

With reference to the Flow Sheets above, P, R, $R^1$, A, Q and n are as defined with respect to the compounds of formula I. P** is a carboxyl covering group.

The side chain A2 or A5 is initially reacted with a suitably protected carbapen-2-em-3-carboxylate having an activated hydroxymethyl group at the 2-position.

The carbapenem nucleus having a hydroxymethyl substituent at position 2 can be obtained in accordance with Schmitt, S. M. et al., *J. Antibiotics* 41(6): 780–787 (1988), the teachings of which are incorporated herein by reference. The carboxylic acid group at C-3 of the carbapenem is generally protected as a carboxyl protecting group such as p-nitrobenzyl (PNB), allyl, p-methoxybenzyl, trichloroethyl, 2-trimethylsilylethyl and the like. Furthermore, the hydroxyl group of the 6-hydroxyethyl) side chain is protected with a hydroxyl protecting group such as trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxycarbonyl, 2-trichloroethoxycarbonyl and the like.

The addition of the side chain to the carbapenem is accomplished by treating a solution of the hydroxymethyl-carbapenem A1 and the side chain A2 or A5 in a suitable solvent such as tetrahydrofuran (THF), ether, acetonitrile, dimethylformamide (DMF), benzene, dimethylsulfoxide (DMSO), and the like with a combination of reagents that comprise the Mitsunobu reaction (for a review see: Hughes, D. L. *Organic Reactions*, Paquette, L. ed., Vol. 42, John Wiley & Sons, USA, 1992. ) such as an azodicarboxylate like diethylazodicarboxylate (DEAD), diisopropyldiazodi-carboxylate (DIAD), and tetramethyldiazodicarboxamide (TMAD), or the like, and a tri-substituted phosphine, such as triphenylphosphine, tri-n-butylphosphine, and the like, at a temperature between about −20° C. and 35° C. for about 5 to 90 minutes.

Alternatively, the naphthosultam and carbapenem can be simultaneously added to a preformed complex of the diazocarboxylate and phosphine. Once the naphthosultam, carbapenem, and activating reagent(s) have been mixed, the reaction is allowed to proceed at a temperature between about −20° C. and 35° C. for about 5 to 90 minutes.

The resulting mixture is then subjected to a standard work-up procedure to afford a crude methyl substituted carbapenem which is purified, if necessary, by recrystallization or by chromatography on silica gel, eluting with a suitable solvent or mixture of two or more solvents, such as hexane, ethyl acetate, ether, benzene, dichloromethane, chloroform, acetone, methanol and the like.

Modification of the side chain, which is generally necessary to introduce the charged substituent, is best accomplished before reacting the carbapenem and the side chain, as in Flow Sheet B. Afterwards, the removal of protecting groups on the hydroxyethyl side chain andlor 3-carbapenem carboxylate can be accomplished. For compounds which contain a hydroxyl group in the side chain, a positively charged substituent may be introduced into the side chain by first activating the hydroxyl group. This entails converting it to a suitable leaving group such as a triflate, mesylate, tosylate, iodide, chloride, bromide, and the like, and then displacing the resulting leaving group with a compound Q, such as N-methyl-imidazole, N-(2-hydroxyethyl)-imidazole, N-methyl-diazabicyclooctane, 1-(carbamoylmethyl)-4-aza-1-azoniabicyclo[2.2.2]octane, 1-(3-hydroxyprop-1-yl)-4-aza-1-azoniabicyclo[2.2.2] octane, pyridine, morpholine and the like which contains a nitrogen atom that can act as a nucleophile.

Alternatively, in some cases, the charged substituent may be incorporated in the side chain after addition of the side chain to the carbapenem, or after deprotection. Introduction of the charged moiety Q before deprotection is greatly preferred.

In some cases, activation of the hydroxyl group and displacement by Q to produce A8 may be accomplished in a single step by taking advantage of the basic character of compound Q and using it as a base in the activation reaction.

The conversion of the hydroxyl group to a suitable leaving group is accomplished by treating the hydroxyl substituted compound in a suitable solvent such as dichloromethane, tetrahydrofuran, ether, benzene, and the like with an activating reagent, such as trifluoromethane-sulfonic anhydride, methanesulfonic anhydride, toluene-sulfonic anhydride, methanesulfonyl chloride, benzene-sulfonyl chloride, toluenesulfonyl chloride, and the like in the presence of a suitable base such as triethylamine, tributylamine, diisopropylethylamine and the like at a temperature between about −100° C. and 0° C. for about 5 to 120 minutes. The intermediate thus obtained contains a leaving group, which may be converted to an alternative leaving group, iodide, by treating a solution of the intermediate in a suitable solvent such as acetone, methyl ethyl ketone, and the like at about −10° C. to 50° C. with an excess of sodium iodide or potassium iodide for about 0.25 to 24 hours.

In many cases, the iodide is obtained in sufficiently pure form that it may be used without further purification. For ease of handling, the iodide, if not crystalline, may be lyophilized from benzene to afford an amorphous, easily handled, solid.

The activated hydroxyl group or iodide is displaced by reacting the activated intermediate with reagent Q. In some cases, activation and displacement of the hydroxyl group may be accomplished in a single step. The activating reagent is added to a solution of the hydroxyl substituted compound in the presence of a suitable base in a suitable solvent such as dichloromethane, tetrahydrofuran, ether, DMF, benzene, acetonitrile, DMSO and the like as described in the preceding paragraphs. The resulting activated intermediate is treated with 1–3 molar equivalents of compound Q at a temperature between −78° C. and 50° C. for about 15 to 120 minutes. In some cases, it is desirable to form the activated intermediate in one solvent, isolate the activated intermediate, and conduct the displacement reaction in a different solvent. In other cases, the displacement may be conducted without isolation of the intermediate and, in cases where Q is also used as a base, may even be concurrent with the formation of the activated intermediate.

In cases where the displacement reaction is best accomplished by using the iodide, a solution of the iodide is combined with an approximately equivalent amount (0.9–1.05 molar equivalents) of compound Q. A silver salt of a non-nucleophilic acid, such as silver trifluoromethanesulfonate, silver tetrafluoroborate and the like is then added. Although the reaction will proceed in the absence of the silver salt, the reaction proceeds more rapidly in the presence of the silver salt. In addition, the silver salt assists in the removal of the displaced iodide from the reaction mixture which can improve the efficiency of subsequent steps. The resulting mixture is then subjected to a standard work-up procedure familiar to those skilled in the art to afford a crude product which is purified, if necessary, by recrystallization or chromatography.

An alternative method for introducing a positive charge into the side chain may be applied to side chains that contain a nitrogen atom which may be quaternized by reaction with a suitable alkylating reagent, such as methyl iodide, methyl bromide, benzyl trichloroacetimidate, methyl trifluoromethanesulfonate, triethyloxonium tetrafluoroborate, and the like. Quaternization of the nitrogen atom in the side chain is effected by treating a solution of the compound with a slight excess (1.05 to 1.2 molar equivalents) of the alkylating reagent.

The synthesis of the target compound is completed by removing any protecting groups which are present in the penultimate intermediate using standard techniques. The deprotected final product is then purified, as necessary, using standard techniques such as ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

The compounds of the present invention are valuable antibacterial agents active against various Gram-positive and to a lesser extent Gram-negative bacteria, and accordingly find utility in human and veterinary medicine.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampoules, or in multidose containers. The injectable compositions may take such forms as suspensions, solutions, or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

EXAMPLE 1

Preparation of 1-hydroxydibenzothiophene

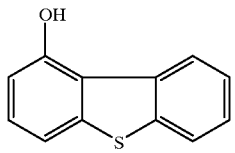

Step A

A stirred mixture of 3-methoxy benzenethiol (0.5 g, 3.6 mmoles), 1-fluoro-2-nitrobenzene (0.5 g, 3.6 mmoles), 37% KF/Al$_2$O$_3$ (1.4755 g, 3 w/w), and 18crown-6 (0.1255 g, 0.36 mmoles) in sieve-dried acetonitrile (5 mL) was refluxed at 90° C. under a N$_2$ atmosphere for 1 hr. The reaction was allowed to cool to ambient temperature. The insoluble solids present in the reaction were filtered off and washed with EtOAc. The filtrate was collected and concentrated in vacuo to give a black/red solid (1.1487 g). The product was purified by plate layer chromatography with a mixture of 2:1 hexane/CH$_2$Cl$_2$ to afford the desired product as a yellow solid (0.7095 g).

$^1$H NMR (CDCl$_3$) δ: 3.82 (s, 3H), 6.90 (dd, 1H), 7.01 (dd, 1H), 7.12–7.23 (m, 3H), 7.33–7.39 (m, 2H), 8.22 (dd, 1H).

Step B

To a stirred solution of the product obtained from Step A (0.7095 g, 2.7 mmoles) in absolute EtOH (7 mL) was added SnCl$_2$.H$_2$O (1.8563 g, 8.1 mmoles). The resulting mixture was refluxed at 90° C. for 1.5 hrs under an atmosphere of N$_2$. The reaction was cooled to ambient temperature, poured into a mixture of ice, brine, and 5 N NaOH, and extracted with EtOAc (2×). The organic layers were combined, washed with brine, and dried over Na$_2$SO$_4$. Concentration in vacuo afforded the desired product as a yellow oil (0.6826 g). The product was purified by plate layer chromatography with 1:1 CH$_2$Cl$_2$/hexane to give the desired amine (0.52 g, quantitative yield).

$^1$H NMR (CDCl$_3$) δ: 3.72 (s, 3H), 4.29 (br s, 2 H), 6.62–6.69 (m, 3H), 6.73–6.80 (m, 2H), 7.11 (t, 1H), 7.21 (t, 1H), 7.44 (dd, 1H).

Step C

To a thick slurry of the amine (0.277 g, 1.74 mmoles) from Step B in 2 N HCl (1.76 mL) and HOAc (0.54 mL) was added absolute EtOH (1.76 mL) to solubilize the mixture. The stirred mixture was cooled to 0° C. and a solution of NaNO$_2$ (0.1552 g, 2.09 mmoles) in water (0.2 mL) was added under N$_2$. The resulting light brown solution was stirred at 0° C. for 20 min. before adding a 93.1 mg/mL aqueous solution of KPF$_6$ (2.7 mL). Upon addition, yellow solid immediately precipitated out of solution. The yellow/brown solid was collected by vacuum filtration and washed with cold water (2×) and cold Et$_2$O (3×). After drying in vacuo over 18 hrs, the diazonium salt was collected as a yellow solid (0.3149 g).

$^1$H NMR (d$_6$-acetone) δ: 3.83 (s, 3H), 7.16 (dd, 1H), 7.27 (s, 1H), 7.27–7.30 (dd, 1H), 7.47 (t, 1H), 7.79 (d, 1H), 7.88 (t, 1H), 8.18 (t, 1H), 8.84 (dd, 1H).

Step D

A solution of FeSO$_4$.7H$_2$O (0.2258 g, 0.81 mmoles) in distilled water (3 mL) was heated to 100° C. The diazonium salt from Step C was added in one portion and the resulting mixture was stirred at 100° C. under N$_2$. Gas evolution was observed for the first 5–10 min. of the reaction. With time, the product oiled out of solution. After 30 min., the reaction was partitioned between EtOAc and ice/brine. The organic layer was collected, dried over Na$_2$SO$_4$, and concentrated in vacuo to give a green/brown oil (0.3317 g). The crude material was purified by plate layer chromatography with 20% CH$_2$Cl$_2$/hexane to afford the desired product as a white solid (0.040 g).

$^1$H NMR (CDCl$_3$) δ: 4.07 (s, 3H), 6.89 (d, 1H), 7.36–7.45 (m, 4H), 7.80 (dd, 1H), 8.64 (dd, 1H).

Step E

To a stirred solution of the dibenzothiophene (0.040 g, 0.19 mmoles) isolated from Step D in HOAc (2.5 mL) was added 40% HBr (0.65 mL, 5.6 mmoles) under N$_2$. The reaction was heated to 130° C. for 20 hrs. The resulting green solution was partitioned between EtOAc and ice/brine. The organic layer was washed with sat. NaHCO$_3$ (2×) and brine. The EtOAc extract was dried over Na$_2$SO$_4$ and concentrated in vacuo to give an off-white solid (0.0366 g). Purification by plate layer chromatography with 1:1 hexane/CH$_2$Cl$_2$ afforded the desired phenol as a white solid (0.0294 g).

$^1$H NMR (CDCl$_3$) δ: 5.53 (s, 1H), 6.77 (d, 1H), 7.26 (t, 1H), 7.43–7.49 (m, 3H), 7.82 (dd, 1H), 8.63 (dd, 1H).

EXAMPLE 2

Preparation of Carbapenem 1

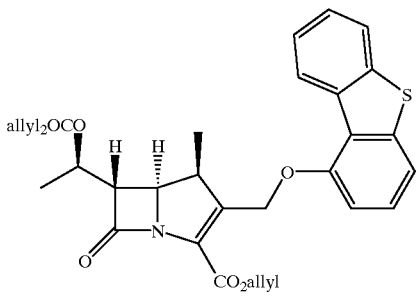

A solution of 1-hydroxybenzothiophene (0.0294 g, 0.15 mmoles), the bis-allyl protected carbinol (0.0684 g, 0.19 mmoles), and triphenylphosphine (0.0592 g, 0.22 mmoles) in distilled THF (1.5 mL) was cooled to 0° C. and placed under a $N_2$ atmosphere. To this stirred solution was added dropwise diisopropylazodicarboxylate (0.06 mL, 0.22 mmoles). The reaction was stirred for 1 hr, and concentrated in vacuo. The residue was purified by plate layer chomatography with double elution using 20% hexane/$CH_2Cl_2$ to afford the coupled product as a yellow oil (0.037 g).

$^1$H NMR (CDCl$_3$) δ: 1.28 (d, 3H), 1.43 (d, 3H), 3.40 (m, 2H), 4.18 (dd, 1H), 4.58–4.63 (dd, 2H), 4.74–4.93 (m, 2H), 5.00 (d, 1H), 5.09 (m, 1H), 5.22–5.52 (m, 4H), 5.84–6.07 (m, 3H), 6.87 (d, 1H), 7.33 (t, 1H), 7.43–7.50 (m, 3H), 7.83 (dd, 1H), 8.57 (dd, 1H).

EXAMPLE 3

Preparation of Carbapenem 2

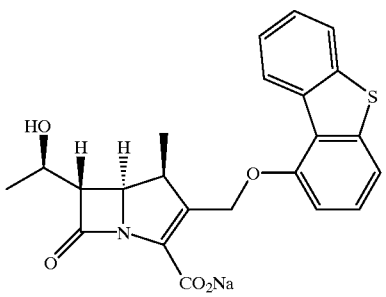

To a solution of carbapenem 1 (0.037 g, 0.068 mmoles) in 1:1 $CH_2Cl_2$/EtOAc (1 mL) was added under $N_2$, 2-ethylhexanoic acid (0.01 mL, 0.074 mmoles), 0.5 M solution of sodium-2-ethyl-hexanoate (0.15 mL, 0.074 mmoles), triphenylphosphine (0.0115 g, 0.004 mmoles), and Pd(PPh$_3$)$_4$ (0.0175 g, 0.001 mmoles) in that order. The reaction was stirred at ambient temperature for 5 min. and then stirred at 0° C. for another 30 min. The product was precipitated out of solution with addition of Et$_2$O (5 mL). The resulting mixture was centrifuged and the supernatant discarded. The product was triturated with additional Et$_2$O (5 mL) and dried in vacuo to give a white/orange solid (0.0146 g). The crude material was purified by reverse phase plate layer chromatography with 7:3 H$_2$O/CH$_3$CN. The desired product was eluted off the silica gel with 4:1 CH$_3$CN/H$_2$O. Lyophilization gave the final compound as a white solid (0.023 g).

$^1$H NMR (5:2 D$_2$O/CD$_3$CN) δ: 1.43 (t, 6H), 3.59–3.63 (m, 2H), 4.36–4.44 (m, 2 H), 5.24 (d, 1H), 6.05 (d, 1H), 7.35 (d, 1H), 7.70–7.83 (m, 4H), 8.19 (dd, 1H), 8.93 (dd, 1H).

EXAMPLE 4

Preparation of 1-hydroxy-5-t-butyldimethylsilyloxymethyl dibenzothiophene

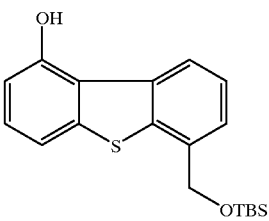

Step A

2-Bromo3-nitrotoluene and 3-methoxy benzenethiol were coupled using the procedures described in Example 1 (Step A) to afford the desired product as a yellow oil.

$^1$H NMR (CDCl$_3$) δ: 2.38 (s, 3H), 3.73 (s, 3H), 6.62–6.66 (m, 2H), 6.68 (dd, 1H), 7.11 (t, 1H), 7.39 (m, 2H), 7.53 (dd, 1H).

Step B

The coupled product from Step A was reduced to its corresponding amine using the procedures described in Example 1 (Step B). The amine was obtained as a green/yellow oil.

$^1$H NMR (CDCl$_3$) δ: 2.39 (s, 3H), 3.71 (s, 3H), 6.58–6.65 (m, 3H), 6.71–4.76 (m, 2H), 7.09 (q, 2H).

Step C

Utilizing the procedure described in Example 1 (Step C), the amine from Step B was converted to its diazonium salt. The product was isolated as a green/yellow solid.

$^1$H NMR (d$_6$-acetone) δ: 2.49 (s, 3H), 3.78 (s, 3H), 6.97–7.02 (m, 3H), 7.35 (t, 1H), 8.04 (t, 1H), 8.31 (d, 1H), 8.87 (d, 1H).

Step D

To a solution of the diazonium salt (0.9275 g, 2.3 mmoles) obtained from Step C in anhydrous DMSO (20 mL) was added 3A molecular sieves. The mixture was heated to 60° C. and stirred for 1 hr. The orange mixture was filtered and the molecular sieves washed well with EtOAc. The filtrate was collected and washed with H$_2$O (4×) followed by brine. The organic layer was dried over Na$_2$SO$_4$ and concentrated in vacuo to give a dark red/orange oil. The crude material was purified by plate layer chromatography with 2:1 hexane/CH$_2$Cl$_2$ to give the desired dibenzothiophene as a white solid (0.1047 g).

$^1$H NMR (CDCl$_3$) δ: 2.58 (s, 3H), 4.08 (s, 3H), 6.91 (d, 1H), 7.25 (d, 1H), 7.36 (t, 2H), 7.47 (d, 1H), 8.50 (d, 1H).

Step E

Utilizing the procedure described in Example 1 (Step E), the product from Step D was demethylated to give the phenol as a white solid.

$^1$H NMR (CDCl$_3$) δ: 2.58 (s, 3H), 6.77 (d, 1H), 7.24–7.31 (2d, 2H), 7.38 (t, 1H), 7.43 (t, 1H), 8.48 (d, 1H).

Step F

To a solution of the phenol (0.076 g, 0.35 mmoles) from Step E in CH$_2$Cl$_2$ (1 mL) was added NEt$_3$ (0.059 mL, 0.42 mmoles) at 0° C. under N$_2$. The reaction was stirred for 10 min. before adding acetyl chloride (0.027 mL, 0.39 mmoles). The reaction was then stirred at 0° C. for another 15 min. and poured into ice/H$_2$O. The mixture was extracted with EtOAc. The organic layers were washed with 1 N HCl followed by brine, and dried over $Na_2SO_4$. Concentration in vacuo gave the desired product as a light brown oil (0.1163 g, quantitative yield).

$^1$H NMR (CDCl$_3$) δ: 2.53 (s, 3H), 2.57 (s, 3H), 7.19 (d, 1H), 7.27 (d, 1H), 7.38 (t, 1H), 7.43 (t, 1H), 7.73 (d, 1H), 8.08 (d, 1H).

Step G

The acetylated product (0.0902, 0.35 mmoles) obtained from Step F was dissolved in $CCl_4$ (0.5 mL) and placed under a $N_2$ atmosphere. NBS (0.0817 g, 0.46 mmoles) was added followed by a crystal of AIBN. The reaction was heated to 80° C. for 23 hrs. The reaction was poured into ice/brine and extracted with EtOAc. The organic layers were washed with 5% $Na_2S_2O_3$ and brine. Concentration in vacuo gave the crude product as a yellow oil (0.2085 g). The oil was purified by plate layer chromatography with 1:1 hexane/$CH_2Cl_2$ to afford the alkyl bromide as a yellow solid (0.0895 g).

$^1$H NMR (CDCl$_3$) δ: 2.53 (s, 3H), 4.77 (s, 2H), 7.23 (d, 1H), 7.46–7.52 (m, 3H), 7.76 (d, 1H), 8.22 (dd, 1H).

Step H

The alkyl bromide (0.0895 g, 0.27 mmoles) from Step G was combined with KOAc (0.0541 g, 0.53 mmoles) in sieve-dried DMF (1 mL) and heated to 100° C. for 1 hr. The reaction was poured into ice/$H_2O$ and extracted with EtOAc. The organic layers were washed with additional $H_2O$ (2×) and brine, and dried over $Na_2SO_4$. Concentration in vacuo gave an orange/red oil (0.114 g). The oil was purified by plate layer chromatography with 3:1 $CH_2Cl_2$/hexane to give a pale yellow solid (0.0635 g).

$^1$H NMR (CDCl$_3$) δ: 2.17 (s, 3H), 2.55 (s, 3H), 5.38 (s, 2H), 7.21 (d, 1H), 7.44–7.49 (m, 3H), 7.73 (d, 1H), 8.22 (dd, 1H).

Step I

A yellow mixture of the product (0.0635 g, 0.2 mmoles) from Step H, 5 N NaOH (0.1 mL, 0.42 mmoles), and absolute EtOH (1 mL) was heated to 70° C. under $N_2$ for 15 min. The reaction was partitioned between EtOAc and ice/1 N HCl. The organic layer was washed with brine, dried over $Na_2SO_4$, and concentrated in vacuo to give an orange solid (0.0637 g). The solid was purified by plate layer chromatography with 5% EtOAc/$CH_2Cl_2$ to give the desired product as a slightly orange solid (0.0335 g).

$^1$H NMR (CDCl$_3$+CD$_3$OD) δ: 4.76 (s, 2H), 6.71 (d, 1H), 7.07 (t, 1H), 7.17 (d, 1H), 7.24–7.28 (m, 2H), 8.45 (d, 1H).

Step J

To a flask charged with the phenol (0.0335 g, 0.16 moles) from Step I was added a solution of TBSCl (0.0305 g, 0.17 mmoles) in DMF (0.5 mL) under $N_2$. The reaction was cooled to 0° C. and stirred for 10 min. before adding dropwise a solution of imidazole (0.0137 g, 0.19 mmoles) in DMF (0.25 mL). The solution was stirred at 0° C. for 1 h. The reaction was partitioned between EtOAc and ice/1 N HCl. The organic layer was washed with brine, dried over $Na_2SO_4$, and concentrated in vacuo to give a light brown oil. The oil was purified by plate layer chromatography with 3:1 $CH_2Cl_2$/hexane to afford the TBS-protected alcohol as a light yellow solid (0.0416 g).

$^1$H NMR (CDCl$_3$) δ: 0.15 (s, 3H), 0.98 (s, 6H), 4.97 (s, 2H), 6.76 (d, 1H), 7.26 (t, 1H), 7.45–7.48 (m, 3H), 8.55 (dd, 1H).

EXAMPLE 5

Preparation of Carbapenem 3

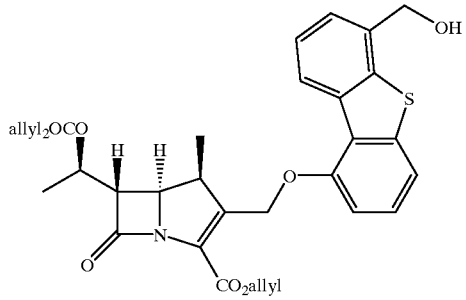

Step A

Utilizing the procedure from Example 2, 1-hydroxy-5-t-butyldimethylsilyloxymethyl dibenzothiophene was coupled with bis-allyl carbinol to afford the desired product as a yellow/orange oil after plate layer chromatography with 3:1 $CH_2Cl_2$/hexane.

$^1$H NMR (CDCl$_3$) δ: 0.15 (s, 3H), 0.98 (s, 6H), 1.27 (d, 3H), 1.41 (d, 3H), 3.41–3.44 (m, 2H), 4.14 (dd, 1H), 4.56–4.58 (m, 2H), 4.75–4.85 (m, 2H), 4.96 (s, 2H), 4.98 (d, 1H), 5.08–5.12 (m, 1H), 5.21–5.48 (m, 4H), 5.80–6.03 (m, 3H), 6.86 (d, 1H), 7.32 (t, 1H), 7.46–7.49 (m, 3H), 8.51 (dd, 1H).

Step B

To a solution of the adduct (0.0572 g, 0.083 mmoles) obtained from Step A in distilled THF (1 mL) was added HOAc (0.028 mL, 0.496 mmoles) followed by 1 M TBAF in THF (0.25 mL, 0.248 mmoles). The reaction was stirred at ambient temperature for 3 hrs. The reaction was partitioned between EtOAc and $H_2O$/brine. The organic layer was washed with sat. NaHCO$_3$ (2×) and brine, and dried over $Na_2SO_4$. After removing the solvent in vacuo, a yellow oil was obtained (0.053 g). The oil was purified by plate layer chromatography with double elution using 5% EtOAc/$CH_2Cl_2$ to afford the desired phenol as a yellow/orange oil (0.0349 g).

$^1$H NMR (CDCl$_3$) δ: 1.27 (d, 3H), 1.41 (d, 3H), 3.41–3.44 (m, 2H), 4.14 (dd, 1H), 4.56–4.58 (m, 2H), 4.75–4.85 (m, 2H), 4.96 (d, 2H), 4.98 (d, 1H), 5.08–5.12 (m, 1H), 5.21–5.48 (m, 4H), 5.80–6.03 (m, 3H), 6.86 (d, 1H), 7.32 (t, 1H), 7.46–7.49 (m, 3H), 8.51 (dd, 1H).

EXAMPLE 6

Preparation of Carbapenem 4

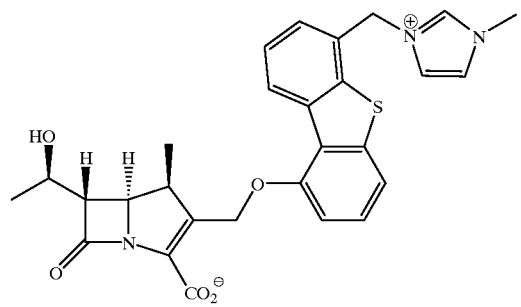

Step A

To a solution of carbapenem 3 (0.0349 g, 0.060 mmoles) in sieve-dried $CH_2Cl_2$ (1 mL) was added 1-methyl imidazole (0.011 mL, 0.13 mmoles) at −20° C. followed by Tf$_2$O (0.011 mL, 0.066 mmoles). The reaction was stirred at −20° C. for 1.5 h and then partitioned between ice/H$_2$O and CH$_2$Cl$_2$. The organic layer was washed with brine, dried over Na$_2$SO$_4$, and concentrated in vacuo to give a pale yellow oil (0.0562 g). The oil was redissolved in CH$_2$Cl$_2$ (0.5 mL) and the product was precipitated out with Et$_2$O as an oil. The mixture was centrifuged and the supernatent discarded. The oil was washed with Et$_2$O and dried in vacuo (0.0462 g, quantitative yield).

$^1$H NMR (CDCl$_3$) δ: 1.27 (d, 3H), 1.42 (d, 3H), 3.36–3.47 (m, 2H), 3.96 (s, 3H), 4.17 (dd, 1H), 4.56–4.60 (m, 2H), 4.71–4.90 (m, 2H), 4.99 (d, 1H), 5.06–5.16 (m, 1H), 5.21–5.49 (m, 4H), 5.62 (s, 2H), 5.79–6.05 (m, 3H), 6.89 (d, 1H), 7.23–7.27 (m, 2H), 7.35 (t, 1H), 7.44 (d, 1H), 7.49–7.60 (m, 2H), 8.57 (dd, 1H), 9.31 (s, 1H).

Step B

The product from Step A was deblocked using the procedures described in Example 3 to afford the final compound as a white solid after lyophilization.

$^1$H NMR (5:2 D$_2$O/CD$_3$CN) δ: 1.42–1.46 (2d, 6H), 3.57–3.62 (m, 2H), 4.07 (s, 3H), 4.33–4.43 (m, 2H), 5.23 (d, 1H), 5.88 (s, 2H), 6.02 (d, 1H), 7.37 (d, 1H), 7.67–7.91 (m, 6H), 8.98 (d, 1H).

EXAMPLE 7

Preparation of Carbapenem 5

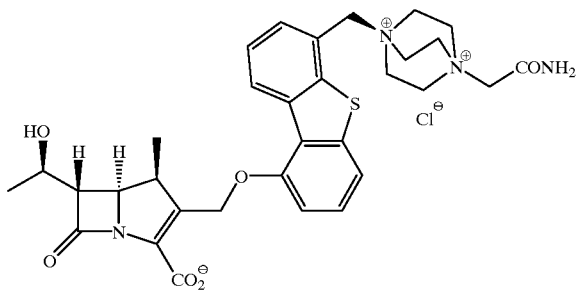

Step A

To a stirred solution of carbapenem 3 (0.0895 g, 0.16 mmoles) in sieve-dried CH$_2$Cl$_2$ (1.5 mL) was added NEt$_3$ (0.032 mL, 0.23 mmoles) at −6° C. under N$_2$ followed by dropwise addition of MsCl (0.016 mL, 0.20 mmoles). The reaction was stirred at −6° C. for 15 min., and then poured into ice/1 M HCl. The resulting mixture was extracted with EtOAc. The organic layer was washed with brine, dried over Na$_2$SO$_4$, and concentrated in vacuo to give a pale yellow oil (0.1027 g, 98% yield). The crude mesylate was dissolved in acetone (2 mL) and cooled to 0° C. NaI (0.0465 g, 0.31 mmoles) was added in one portion under N$_2$. With time the reaction became increasingly yellow. The reaction was stirred at 0° C. for 1 hr and then partitioned between ice/brine and EtOAc. The organic layer was dried over Na$_2$SO$_4$ and concentrated in vacuo to afford the alkyl iodide as a yellow oil (0.1045 g).

$^1$H NMR (CDCl$_3$) δ: 1.27 (d, 3H), 1.41 (d, 3H), 3.35–3.42 (m, 1H), 3.43 (dd, 1H), 4.14 (dd, 1H), 4.57–4.59 (m, 2H), 4.68 (s, 2H), 4.71–4.89 (m, 2H), 4.99 (d, 2H), 5.06–5.13 (m, 1H), 5.21–5.51 (m, 4H), 5.80–6.03 (m, 3H), 6.86 (d, 1H), 7.32–7.52 (m,4H), 8.49 (d, 1H).

Step B

To a solution of the alkyl iodide (0.1045 g, 0.15 mmoles) obtained from Step A in sieve-dried acetonitrile (2 mL) was added dabco acetamide triflate salt (0.0481 g, 0.15 mmoles) followed by AgOTf (0.0394 g, 0.15 mmoles) at ambient temperature under N$_2$. Upon addition of AgOTf, a yellow precipitate formed. The resulting mixture was stirred for 40 min. and filtered through a celite pad. The celite was washed well with acetonitrile and the filtrate concentrated in vacuo. The residue was dissolved in acetone (4 mL) and filtered through a cotton plug into a centrifuge tube. The solution was reconcentrated under a stream of N$_2$ to give a rose-colored oil (0.1585 g, quantitative yield).

$^1$H NMR (d$_6$-acetone) δ: 1.35–1.41 (2d, 6H), 3.56–378 (m, 2H), 3.34 (dd, 1H), 4.34 (dd, 1H), 4.52–4.88 (m, 18H), 5.01–5.57 (m, 8H), 5.80 (d, 1H), 5.87–6.05 (m, 2H), 7.18 (d, 1H), 7.20–7.25 (bs, 1H), 7.53 (t, 1H), 7.62–7.71 (m, 3H), 7.86 (d, 1H), 8.91 (d, 1H).

Step C

The product (0.0696 g, 0.068 mmoles) from Step B was deblocked using the procedure described in Example 3 with the exception of sieve-dried DMF as the solvent. The reaction became increasingly cloudy over time. After 1 hr, the reaction was cooled to 0° C. and the product was further precipitated with the addition of acetone. The crude material (0.0377 g) was collected as a hexanoate salt after washing with acetone and centrifugation. The compound was dissolved in a minimal amount of H$_2$O and purified via a reverse-phase HPLC equipped with a 10 mL column of MacroPrep ion exchange resin in conjunction with a 10 mL column of Amberchrom CG 161.

The following HPLC conditions used are listed below:

| Time [min] | Flow rate [mL/min] | Eluant |
|---|---|---|
| Macroprep column | | |
| 0–5 | 10 | water |
| 5–10 | 10 | 5% NaCl |
| 10–30 | 15 | 5% NaCl |
| Amberchrom CG 161 column [linear gradient | | |
| 0–15 | 10 | water |
| 15–20 | 10 | 100% H$_2$O to 60:40 CH$_3$CN/H$_2$O |

After lyophilization, the final compound was obtained as a white solid (0.0155 g).

$^1$H NMR (5:2 D$_2$O/CD$_3$CN) δ: 1.47 (d, 6H), 3.60–3.67 (m, 2H), 4.33–4.82 (m, 16H), 5.24–5.31 (m, 3H), 6.02 (d, 1H), 7.42 (d, 1H), 7.78–7.96 (m, 4H), 9.07 (dd, 1H).

EXAMPLE 8

Preparation of 1-hydroxy-5-t-butyldimethysilyloxypropyl dibenzothiophene

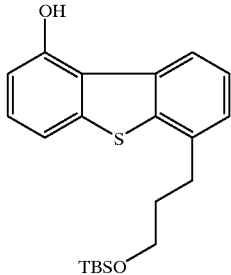

Step A

The acetylated dibenzothiophene (0.3985, 1.55 mmoles) obtained from Example 4 (Step F) was dissolved in CCl$_4$ (5 mL) and place under a N₂ atmosphere. Recrystallized NBS (0.3051 g, 1.7 mmoles) was added followed by a crystal of AIBN. The reaction was heated to 80° C. for 23 hrs. Additional NBS (0.3067 g, 1.7 mmoles) was added to the reaction and the mixture was stirred at 80° C. for another 6.5 hrs. The reaction was poured into ice/brine and extracted with EtOAc. The organic layers were washed with 5% $Na_2S_2O_3$ and brine. Concentration in vacuo gave an orange solid (0.5974 g). By ¹H NMR analysis, the crude product contained a 3:1 mixture of the desired dibrominated product to the monobrominated product or 74% yield of dibrominated product.

¹H NMR (CDCl₃) δ: 2.55 (s, 3H), 6.96 (s, 1H), 7.25 (d, 1H), 7.48–7.50 (m, 2H), 7.76 (t, 2H), 8.24 (d, 1H).

Step B

The crude alkyl bromide (0.4670 g, 1.1 mmoles) from Step A was dissolved in sieve-dried DMF (5 mL) and placed under N₂. KOAc (0.3396 g, 3.4 mmoles) was added in one portion and the reaction was heated to 100° C. After 1.5 hrs, The reaction was partitioned between EtOAc and H₂O. The organic layer was washed with water (3×) and brine, dried over $Na_2SO_4$, and concentrated in vacuo to give a brown/yellow oil (0.6382 g). The oil was purified by plate layer chromatography with 4 elutions using 3:2 $CH_2Cl_2$/hexane to give 2 major fractions: 1) the triacetate compound (0.1403 g) and 2) a mixture of the diacetate compound and the aldehyde (0.2077 g).

¹H NMR (CDCl₃) δ: 2.18 (s, 6H), 2.55 (s, 3H), 7.23 (d, 1H), 7.47 (t, 2H), 7.61 (d, 1H), 7.75 (d, 1H), 7.93 (s, 1H), 8.31 (dd, 1H).

Step C

The fraction from Step B containing the triacetate compound (0.1255 g, 0.4 mmoles) was suspended in absolute EtOH (2 mL) and 5 N NaOH (0.15 mL, 0.8 mmoles) was added under N₂. The reaction was heated to 70° C. for 20 min. then poured into ice/1 M HCl. The mixture was extracted with EtOAc. The organic layer was collected, washed with brine, dried over $Na_2SO_4$, and concentrated in vacuo to give an orange solid (0.1065 g). The solid was purified by plate layer chromatography with 5% EtOAc/$CH_2Cl_2$ to afford the clean aldehyde as a yellow solid (0.0756 g).

¹H NMR (CDCl₃+d₆-acetone) δ: 6.73 (d, 1H), 7.07 (t, 1H), 7.21 (d, 1H), 7.40 (t, 1H), 7.73 (d, 1H), 8.78 (dd, 1H), 9.00 (bs, 1 H), 10.04 (s, 1H).

Step D

The fraction from Step B containing a mixture of the diacetate compound and the aldehyde (0.2077 g, 0.77 moles) was submitted under the same reaction conditions described in Step C. The resulting mixture of aldehyde and diol was separated by plate layer chromatography with 5% EtOAc/$CH_2Cl_2$ to give 0.0895 g of clean aldehyde.

Step E

The aldehydes from Step C and Step D were combined and acetylated using the procedures described in Example 4 (Step F). The reaction was stirred at 0° C. for a total of 30 min. The desired product was isolated as tan solid.

¹H NMR (CDCl₃) δ: 2.57 (s, 3 H), 7.29 (d, 1H), 7.50 (t, 1H), 7.65 (t 1H), 7.82 (d, 1H), 7.99 (dd, 1H), 8.54 (dd, 1H), 10.29 (s, 1H).

Step F

The acetylated product (0.1572 g, 0.58 mmoles) from Step E was dissolved in $CH_2Cl_2$ (3 mL) and methyl (triphenylphosphoranylidene)-acetate (0.2141 g, 0.64 mmoles) was added under N₂. The mixture was stirred at ambient temperature for 1.5 hrs. The reaction was concentrated in vacuo to give a white/yellow solid. The solid was purified by plate layer chromatography with 5% hexane/$CH_2Cl_2$ to give the desired ester as a white solid (0.1688 g).

¹H NMR (CDCl₃) δ: 2.54 (s, 3 H), 3.86 (s, 3H), 6.67 (d, 1H), 7.24 (d, 1H), 7.48 (t 2H), 7.66 (d, 1H), 7.77 (d, 1H), 7.95 (d, 1H), 8.28 (d, 1H).

Step G

To a solution of the ester obtained from Step F (0.1688 g, 0.51 mmoles) in 1:1 EtOAc/EtOH was added 10% Pd/C (0.0186, 10% w/w). The resulting mixture was degassed with N₂ and hydrogenated under atmospheric H₂ pressure for 3 hrs. The reaction was degassed with N₂ and the catalyst removed by filtering through a celite pad. The filtrate was concentrated in vacuo to give a white/yellow solid (0.1595 g).

1H NMR (CDCl₃) δ: 2.53 (s, 3 H), 2.80 (t, 2H), 3.21 (t, 2H), 3.70 (s, 3H), 7.21 (t, 1H), 7.31 (d, 1H), 7.40–7.49 (m, 2H), 7.73 (dd, 1H), 8.12 (dd, 1H).

Step H

The alkyl ester isolated from Step G (0.1595 g, 0.49 mmoles) was dissolved in absolute EtOH (2 mL), and 5 N NaOH (0.29 mL, 1.5 mmoles) was added under N₂. The resulting yellow mixture was heated to 70° C. After 1 hr, the reaction was partitioned between ice/1 M HCl and EtOAc. The organic layer was washed with brine, dried over $Na_2SO_4$, and concentrated in vacuo to afford the desired acid as a pale yellow solid (0.1614 g, quantitative yield).

¹H NMR (CDCl₃+d₆-acetone) δ: 2.77 (t, 2H), 3.15 (t, 2H), 6.81 (d, 1H), 7.18–7.26 (m, 2H), 7.32 (t, 1H), 7.32 (d, 1H), 8.52 (d, 1H).

Step I

To a solution of the carboxylic acid generated in Step H (0.1614, 0.49 mmoles) in distilled THF (5 mL) was added dropwise a 1 M solution of BH₃.THF in THF (0.98 mL, 0.98 mmoles). Upon addition, gas evolution was observed. With time, the reaction became a cloudy green mixture. The reaction was stirred at ambient temperature for a total of 2 hrs. The reaction was quenched with dropwise addition of MeOH until no further gas evolution was observed. The reaction mixture was concentrated in vacuo and the residue was purified by plate layer chromatography with 5% EtOAc/$CH_2Cl_2$ to give the desired diol as a white solid (0.1065 g).

¹H NMR (CDCl₃+d₆-acetone) δ: 1.88 (m, 2H), 2.81 (t, 2H), 3.57 (t, 2H), 6.74 (d, 1H), 7.08 (t, 2H), 7.10 (d, 1H), 7.21–7.27 (m, 2H), 8.42 (d, 1H), 8.69 (bs, 1 H).

Step J

Utilizing the procedure described in Example 4 (Step J), the diol obtained from Step I was selectively protected at the primary alcohol position to give the desired TBS-protected product as a yellow oil after plate layer chromatography with 5% EtOAc/$CH_2Cl_2$.

¹H NMR (CDCl₃) δ: 0.07 (s, 3H), 0.92 (s, 6 H), 1.99 (m, 2H), 2.92 (t, 2H), 3.70 (t, 2H), 6.74 (d, 1H), 7.24–7.27 (m, 2H), 7.38–7.43 (m, 2H), 8.48 (d, 1H).

EXAMPLE 9

Preparation of Carbapenem 6

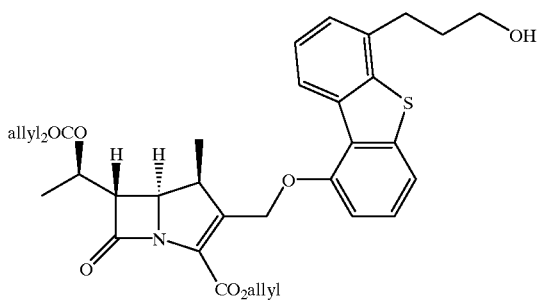

Step A

1-Hydroxy-5-t-butyldimethylsilyloxypropyl dibenzothiophene was coupled with the bis-allyl protected carbinol using the procedure described in Example 2 to give the adduct as a yellow oil after plate layer chromatography with 3:1 $CH_2Cl_2$/hexane.

$^1$H NMR ($CDCl_3$) δ: 0.09 (s, 3H), 0.94 (s, 6H), 1.29 (d, 3H), 1.43 (d, 3H), 1.98 (m, 2H), 2.93 (t, 2H), 3.35–3.48 (m, 2 H), 3.70 (t, 2H), 4.17 (dd, 1H), 4.58–4.63 (m, 2H), 4.74–4.93 (m, 2H), 5.00 (d, 1H), 5.09–5.18 (m, 1H), 5.22–5.52 (m, 4H), 5.84–6.07 (m, 3H), 6.87 (d, 1H), 7.26–7.51 (m, 4H), 8.43 (dd, 1H).

Step B

The adduct from Step A was desilylated following the procedures presented in Example 5 (Step B) with the exception that the reaction was stirred for 4.5 hrs. The desired alcohol was isolated.

$^1$H NMR ($CDCl_3$) δ: 1.29 (d, 3H), 1.43 (d, 3H), 1.98 (m, 2H), 2.93 (t, 2H), 3.35–3.48 (m, 2 H), 3.70 (m, 2H), 4.17 (dd, 1H), 4.58–4.63 (m, 2H), 4.74–4.93 (m, 2H), 5.00 (d, 1H), 5.09–5.18 (m, 1H), 5.22–5.52 (m, 4H), 5.84–6.07 (m, 3H), 6.87 (d, 1H), 7.26–7.51 (m, 4H), 8.43 (dd, 1H).

EXAMPLE 10

Preparation of Carbapenem 7

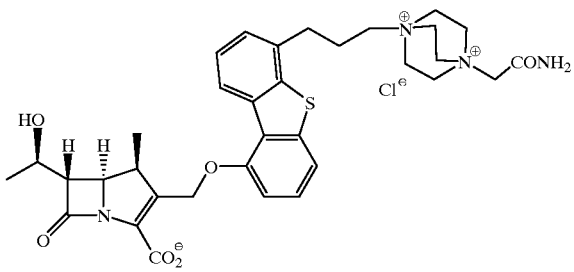

Step A

To a solution of carbapenem 6 (0.0561 g, 0.093 mmoles) in sieve-dried $CH_2Cl_2$ (1 mL) at −8° C. was added 2,6-lutidine (0.016 mL, 0.14 mmoles) under $N_2$ followed by $Tf_2O$ (0.017 mL, 0.10 mmoles). After 25 min., additional $Tf_2O$ (1.1x) and 2,6lutidine (1.5x) was added to the reaction. The reaction was stirred for another 10 min before partitioning the reaction between EtOAc and ice/1 M HCl. The organic layer was washed with brine, dried over $Na_2SO_4$, and concentrated in vacuo to give the crude triflate as a yellow oil (0.0778 g, quantitative yield).

$^1$H NMR ($CDCl_3$) δ: 1.29 (d, 3H), 1.43 (d, 3H), 2.31 (m, 2H), 3.02 (t, 2H), 3.35–3.48 (m, 2 1H), 4.17 (dd, 1H), 4.58–4.63 (m, 4H), 4.74–4.93 (m, 2H), 5.00 (d, 1H), 5.09–5.18 (m, 1H), 5.22–5.52 (m, 4H), 5.84–6.07 (m, 3H), 6.89 (d, 1H), 7.26–7.52 (m, 4H), 8.44 (dd, 1H).

Step B

To a solution of the triflate obtained from Step A (0.0778 g, 0.093 mmoles) in sieve-dried $CH_3CN$ was added dabco acetamide triflate salt (0.0298 g, 0.093 mmoles) under $N_2$. The reaction was stirred at ambient temperature for 1 hr and 20 min. The reaction was concentrated in vacuo to give a rose-colored oil (0.106 g). The oil was dissolved in acetone (2.5 mL) and the product was precipitated out of solution with the addition of $Et_2O$ (8 mL). The solid was isolated by centrifugation and rewashed with $Et_2O$ to give the desired product (0.0788 g).

$^1$H NMR ($d_6$-acetone) δ: 1.38 (d, 6H), 2.51 (m, 2H), 3.05 (t, 2H), 3.54 (m, 1H), 3.69–3.77 (m, 2H), 4.00 (m, 2H), 4.32–4.88 (m, 19H), 5.10–5.51 (m, 6H), 5.78 (d, 1H), 5.87–6.06 (m, 2H), 7.09 (d, 1H), 7.23 (bs, 1H), 7.43–7.51 (m, 3H), 7.57 (d, 1H), 7.68 (bs, 1H), 8.59 (dd, 1H).

Step C

The dabco quat from Step B was deallylated following the procedures described in Examples 7 (Step C) to afford the desired product as a white solid.

$^1$H NMR (5:2 $D_2O/CD_3CN$) δ: 1.40 (d, 6H), 2.44 (m, 2H), 3.16 (t, 2H), 3.60–3.69 (m, 2H), 3.78 (m, 2H), 4.09–4.82 (m, 16H), 5.28 (d, 1H), 5.97 (d, 1H), 7.31 (d, 1H), 7.59 (d, 1H), 7.67–7.79 (m, 3H), 8.78 (d, 1H).

EXAMPLE 11

Preparation of Carbapenem 8

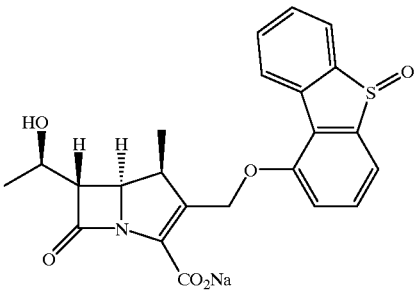

Step A

A solution of carbapenem 1 (0.099 g, 0.18 mmoles) in $CH_2Cl_2$ (2 mL) was cooled to 0° C. and a solution of 85 wt % MCPBA (0.0436 g, 0.20 mmoles) in $CH_2Cl_2$ (2 mL) was added over 10 min. via a dropping funnel. The reaction was allowed to stir at 0° C. for 30 min. The reaction was quenched with 5% $Na_2S_2O_3$ and extracted with EtOAc. The organic layer was washed with 5% $Na_2S_2O_3$ and brine, dried over $Na_2SO_4$, and concentrated in vacuo to give a yellow oil (0.093 g). The oil was purified by plate layer chromatography with 10% EtOAc/$CH_2Cl_2$ to afford the sulfoxide as a mixture of diastereomers (0.0496 g).

$^1$H NMR ($CDCl_3$) δ: 1.26 (d, 3H), 1.41 (dd, 3H), 3.25–3.49 (m, 2H), 4.17 (m, 1H), 4.57 (m, 2H), 4.71–5.51 (m, 8H), 5.76–6.05 (m, 3H), 7.06 (t, 1H), 7.40–7.64 (m, 4H), 7.97 (d, 1H), 8.16 (dd, 1H).

Step B

The final compound was isolated in 60% yield after submitting the sulfoxide obtained in Step A to the conditions described in Example 3.

$^1$H NMR (5:2 $D_2O/CD_3CN$) δ: 1.45 (d, 6H), 3.52–3.63 (m, 2H), 4.36–4.44 (m, 2 H), 5.20 (dd, 1H), 6.03 (dd, 1H), 7.63 (d, 1H), 7.81–7.93 (m, 3H), 7.98 (t, 1H), 8.28 (d, 1H), 8.60 (d, 1H).

EXAMPLE 12

Preparation of Carbapenem 9

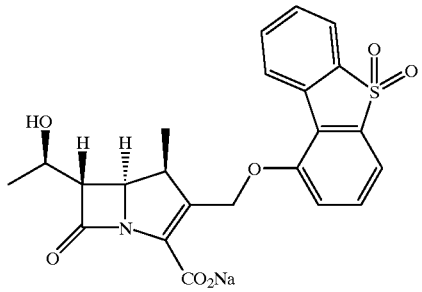

The sulfone was prepared in an analogous manner to Example 11 using 3 equivalents of MCPBA in the oxidation step (Example 11, Step A). The final compound was isolated as a white solid.

$^1$H NMR (5:2 D$_2$O/CD$_3$CN) δ: 1.50 (2d, 6H), 3.59 (m, 1H), 3.67 (dd, 1H), 4.43 (dd, 1H), 4.45 (m, 1H), 5.30 (d, 1H), 6.11 (d, 1H), 7.77 (d, 1H), 7.80 (d, 1H), 7.92 (t, 2H), 8.10 (t, 1H), 8.21 (d, 1H), 8.69 (d, 1H).

EXAMPLE 13

Preparation of Carbapenem 10

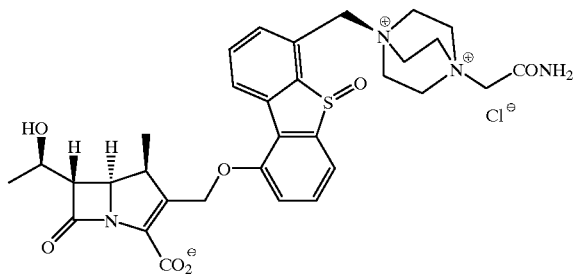

To a solution of carbapenem 5 (0.0100 g, 0.016 mmoles) in 1:1 acetone/H$_2$O (1 mL) was added 0.44 mL of a stock solution (0.024 g/mL) of dimethyl dioxirane in acetone at 0° C. under N$_2$. The reaction was followed by reverse-phase HPLC. After 50 min., an additional 0.040 mL of dimethyl dioxirane was added to the reaction. The reaction was stirred for another 20 min., then concentrated in vacuo. The aqueous residue was lyophilized to give the sulfoxide in 54% purity by $^1$H NMR and UV as a white solid (0.0071 g).

$^1$H NMR (5:2 D$_2$O/CD$_3$CN) δ: 1.45 (m, 6H), 3.27–3.61 (m, 2H), 4.28–4.82 (m, 16 H), 5.04–5.46 (m, 3H), 5.73–5.93 (m, 1H), 7.53–8.15 (m, 5H), 8.62–8.71 (m, 1H).

EXAMPLE 14

Preparation of Carbapenem 11

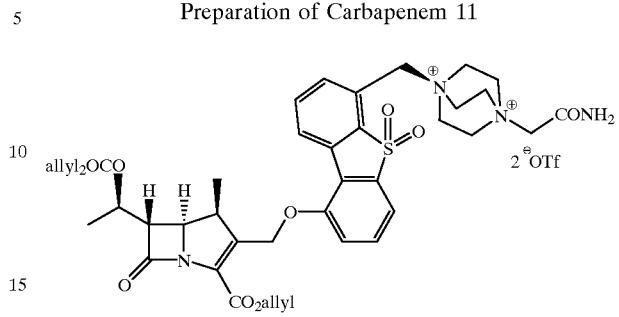

Step A

Carbapenem 3 was treated with 3 equivalents of a 0.057 M solution of dimethyl dioxirane in acetone in the same manner described in Example 13 with the exception that the reaction was complete within 20 min. Purification of the crude material by plate layer chromatography with 15% EtOAc/CH$_2$Cl$_2$ gave the desired sulfone in quantitative yield.

$^1$H NMR (CDCl$_3$) δ: 1.23 (d, 3H), 1.43 (d, 3H), 3.27 (m, 1H), 3.45 (dd, 1H), 4.19 (dd, 1H), 4.58–4.91 (m, 4H), 4.94 (d, 1H), 5.08–5.51 (m, 7H), 5.78 (d, 1H), 5.83–6.05 (m, 2H), 7.11 (dd, 1H), 7.44–7.66 (m, 4H), 8.12 (d, 1H).

Step B

The sulfone generated in Step A was converted to the alkyl iodide following the procedures described in Example 7 (Step A) with the exception that initial mesylation was complete after 35 min. and 5 equivalents of NaI at ambient temperature for 4.5 hrs was necessary to drive the reaction to completion. The iodide was isolated in quantitative yield as a red/orange oil.

$^1$H NMR (CDCl$_3$) δ: 1.23 (d, 3H), 1.41 (d, 3H), 3.24 (m, 1H), 3.45 (dd, 1H), 4.19 (dd, 1H), 4.58–4.90 (m, 4H), 4.78 (s, 2H), 4.93 (d, 1H), 5.07–5.51 (m, 5H), 5.78 (d, 1H), 5.83–6.05 (m, 2H), 7.11 (m, 1H), 7.44–7.59 (m, 4H), 8.06 (d, 1H).

Step C

Utilizing the procedure from Example 7 (Step B) with the exception that the reaction was stirred at ambient temperature for 19 hrs, the dabco quaternized carbapenem was prepared by reacting the alkyl iodide isolated from Step B with the dabco acetamide triflate salt.

$^1$H NMR (d$_6$-acetone) δ: 1.35 (d, 6H), 3.50 (m, 1H), 3.72 (dd, 1H), 4.34 (dd, 1H), 4.58–4.87 (m, 18H), 5.09–5.50 (m, 8H), 5.77 (d, 1H), 5.89–6.05 (m, 2H), 7.22 (bs, 1H), 7.52 (t, 2H), 7.66–7.76 (m, 3H), 7.93–8.02 (m, 2H), 8.69 (dd, 1H).

EXAMPLE 15

Preparation of Carbapenem 12

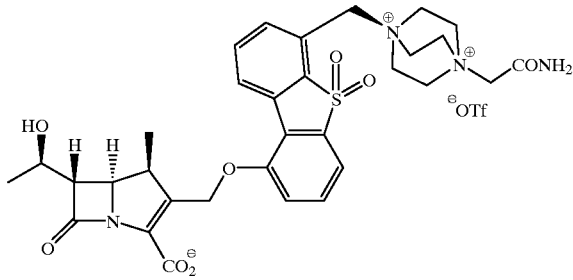

A mixture of carbapenem 11 (0.0761 g, 0.072 mmoles), triphenylphosphine (0.028 g, 0.011 mmoles), Pd(PPh$_3$)$_4$ (0.0047 g, 0.036 mmoles), and dimedone (0.0302 g, 0.20 mmoles) in sieve-dried DMF (1 mL) was sparged with N$_2$. iPr$_2$NEt (0.037 mL, 0.20 mmoles) was then added. The reaction was stirred at ambient temperature for 1 hr. The product was precipitated out of solution with Et$_2$O (6 mL). The mixture was centrifuged and the supernatent was discarded. The solid pellet was washed with Et$_2$O and recentrifuged. The pellet was collected and dried in vacuo to give an off-white solid (0.050 g). 0.012 g of the crude material was purified on reverse phase HPLC by eluting the compound through a 10 mL column of Amberchrom CG 161 with a linear gradient (100% water to 40:60 CH$_3$CN/H$_2$O over 35 min). The aqueous fractions were lyophilized to give the desired product in 82% purity (0.0082 g).

$^1$H NMR (5:2 D$_2$O/CD$_3$CN) δ: 1.44 (t, 6H), 3.52–3.61 (m, 1H), 3.66 (dd, 1H), 4.49–4.86 (m, 16H), 5.29–5.40 (m, 3H), 6.03 (d, 1H), 7.79–7.84 (2d, 2H), 7.95–8.03 (m, 2H), 8.21 (t, 1H), 8.90 (d, 1H).

EXAMPLE 16

Preparation of 1-hydroxy-5-t-butyldimethylsilyloxymethyl dibenzofuran

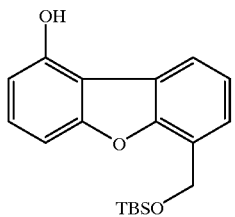

Step A

To a mixture of 2,6-difluoronitrobenzene (1.0 g, 6.3 mmoles) in MeOH (10 mL) was added a 4.4 M solution of NaOMe in MeOH (1.57 mL, 6.9 mmoles). The mixture was heated to 70° C. for 20 min. The resulting orange reaction mixture was concentrated in vacuo. The residue was dissolved in EtOAc and washed with H$_2$O and brine. The organic layer was dried over Na$_2$SO$_4$ and concentrated in vacuo to give a pale yellow solid. The solid was purified by plate layer chromatography with 1:1 hexane/CH$_2$Cl$_2$ to give clean product as a pale yellow solid (1.0559 g).

$^1$H NMR (CDCl$_3$) δ: 3.89 (s, 3H), 6.77–6.85 (m, 2H), 7.36–7.41 (m, 1H).

Step B

The methoxy nitrobenzene isolated from Step A was coupled with o-cresol (0.64 mL, 6.2 mmoles) using the procedures described in Example 1 (Step A) with the exception that the reaction time was 3 hrs. After purification by plate layer chromatography with 1:1 hexane/CH$_2$Cl$_2$, the desired adduct was obtained as a pale yellow solid.

$^1$H NMR (CDCl$_3$) δ: 2.18 (s, 3H), 3.91 (s, 3H), 6.27 (d, 1H), 6.66 (d, 1H), 6.98 (d, 1H), 7.10–7.27 (m, 4H).

Step C

The adduct from Step B (1.3924 g, 5.4 mmoles) was hydrogenated under 40–46 psi of H$_2$ in a Parr Shaker for 5 days using 10% Pd/C (0.139 g, 10 w/w) in 1:1 EtOH/EtOAc. The catalyst was filtered off through a celite pad and the filtrate was concentrated in vacuo. The product was obtained as a yellow oil (1.2833 g, quantitative yield).

$^1$H NMR (CDCl$^3$) δ: 2.30 (s, 3H), 3.88 (s, 3H), 6.36 (m, 1H), 6.60 (m, 2H), 6.79 (d, 1H), 6.97 (t, 1H), 7.08 (t, 1H), 7.21 (d, 1H).

Step D

The amine from Step C was converted to its KPF$_6$ diazonium salt using the procedures described in Example 1 (Step C). The product was isolated as a yellow solid.

$^1$H NMR (d$_6$-acetone) δ: 2.26 (s, 3H), 4.36 (s, 3H), 6.57 (d, 1H), 7.25 (d, 1H), 7.32 (d, 1H), 7.38 (t, 2H), 7.46 (dd, 1H), 8.17 (t, 1H).

Step E

A mixture of 0.438 g (0.48 mmoles) of Pd$_2$(dba)$_3$ in anhydrous DMSO (30 mL) was heated to 100° C. under N$_2$ and the diazonium salt from Step D (1.8489 g, 4.8 mmoles) was added in one portion, resulting in significant gas evolution. The reaction was stirred at 100° C. for 40 min and then filtered through celite. The filtrate was partitioned between EtOAc and water. The organic layer was washed well with H$_2$O (2x) followed by brine. The organic layer was dried over Na$_2$SO$_4$ and concentrated in vacuo to give a black solid. The solid was purified by plate layer chromatography with 2:1 hexane/CH$_2$Cl$_2$ to give the desired product as a white solid (0.4335 g).

$^1$H NMR (CDCl$_3$) δ: 2.59 (s, 3H), 4.05 (s, 3H), 6.77 (d, 1H), 7.20–7.27 (m, 3H), 7.35 (t, 1H), 7.95 (dd, 1H).

Step F

The dibenzofuran from Step E was demethylated and acetylated using the procedures described in Example 1 (Step E) and Example 4 (Step F) respectively. The desired product was obtained as a white solid over the 2 steps.

$^1$H NMR (CDCl$_3$) δ: 2.50 (s, 3H), 2.58 (s, 3H), 7.11 (dd, 1H), 7.21–7.30 (m, 2H), 7.41–7.50 (m, 2H), 7.64 (dd, 1H).

Step G 0.1126 g (0.49 mmoles) of acetylated dibenzofuran from Step F, recrystallized NBS (0.0970 g, 0.54 mmoles), benzoyl peroxide (0.0271 g, 0.099 mmoles), and CCl$_4$ (3 mL) were combined under N$_2$ and heated to 100° C. In addition to heating, the reaction was illuminated with a sun lamp. Within 30 min., the reaction became dark purple. After 2 hrs, another 0.3 equivalents of NBS and 0.0312 g of benzoyl peroxide were added. The reaction was heated for another 2 hrs, and then partitioned between EtOAc and 5% Na$_2$S$_2$O$_3$. The organic layer was washed with H$_2$O and brine, dried over Na$_2$SO$_4$, and concentrated in vacuo to give a dark purple solid. The solid was purified by plate layer chromatography with 2:1 CH$_2$Cl$_2$/hexane to afford the desired alkyl bromide as an off-white solid (0.081 g).

$^1$H NMR (CDCl$_3$) δ: 2.50 (s, 3H), 4.84 (s, 2H), 7.16 (dd, 1H), 7.30 (t, 1H), 7.47–7.55 (m, 3H), 7.77 (dd, 1H).

Step H

The diacetate was prepared after plate layer chromatography with 2:1 CH$_2$Cl$_2$/hexane, from the alkyl bromide of Step G using the procedures described in Example 4 (Step H).

$^1$H NMR (CDCl$_3$) δ: 2.14 (s, 3H), 2.51 (s, 3H), 5.49 (s, 2H), 7.15 (dd, 1H), 7.32 (t, 1H), 7.44–7.52 (m, 3H), 7.80 (dd, 1H).

Step I

The diacetate from Step H was treated under the same conditions as Example 4 (Step I) to give the crude diol.

$^1$H NMR (CDCl$_3$+CD$_3$OD) δ: 5.00 (s, 2H), 6.67 (d, 1H), 7.03 (d, 1H), 7.19–7.30 (m, 2H), 7.38 (dd, 1H), 8.02 (dd, 1H).

Step J

The diol from Step I was selectively protected at the primary position using the procedures described in Example 4 (Step J) to give the desired product as a white solid after plate layer chromatography with 2:1 CH$_2$Cl$_2$/hexane.

$^1$H NMR (CDCl$_3$) δ: 0.15 (s, 3H), 0.97 (s, 6H), 5.15 (s, 2H), 6.68 (d, 1H), 7.15 (d, 1H), 7.25 (t, 1H), 7.33 (t, 1H), 7.53 (d, 1H), 7.98 (d, 1H).

EXAMPLE 17

Preparation of Carbapenem 13

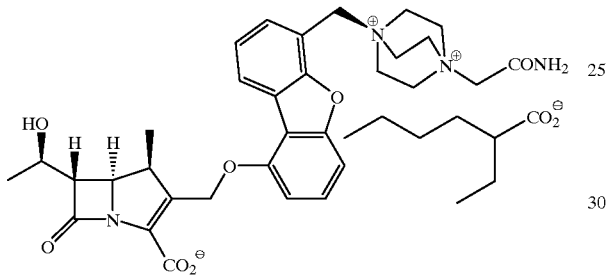

Step A

The carbapenem adduct was prepared by coupling 1-hydroxy-5-t-butyldimethylsilylmethyl dibenzofuran with bis-allyl protected carbinol in an analogous manner to Example 2 to give the desired product as a light purple oil.

$^1$H NMR (CDCl$_3$) δ: 0.15 (s, 3H), 0.97 (s, 6H), 1.30 (d, 3H), 1.44 (d, 3H), 3.46 (dd, 1H), 3.49 (m,1H), 4.20 (dd, 1H), 4.60 (dd, 2H), 4.72–4.91 (m, 2H), 4.96 (d, 1H), 5.09–5.51 (m, 5H), 5.13 (s, 2H), 5.73 (d, 1H), 5.85–6.07 (m, 2H), 6.77 (d, 1H), 7.21 (t, 1H), 7.31–7.40 (m, 2H), 7.52 (t, 1H), 7.92 (d, 1H).

Step B

Desilylation of the carbapenem from Step A was accomplished using the procedures described in Example 5 (Step B) to give the desired alcohol as a yellow oil.

$^1$H NMR (CDCl$_3$) δ: 1.30 (d, 3H), 1.44 (d, 3H), 3.46 (dd, 1H), 3.49 (m, 1H), 4.20 (dd, 1H), 4.60 (dd, 2H), 4.72–4.91 (m, 2H), 4.96 (d, 1H), 5.08 (s, 2H), 5.10 (m, 1H), 5.24–5.51 (m, 4H), 5.73 (d, 1H), 5.85–6.07 (m, 2H), 6.70 (d, 1H), 7.23–7.50 (m, 4H), 8.03 (dd, 1H).

Step C

The alcohol from Step B was converted to its corresponding alkyl iodide following procedures presented in Example 7 (Step A).

$^1$H NMR (CDCl$_3$) δ: 1.30 (d, 3H), 1.44 (d, 3H), 3.46 (dd, 1H), 3.49 (m, 1H), 4.20 (dd, 1H), 4.60 (m, 2H), 4.71–4.89 (m, 2H), 4.75 (s, 2H), 4.95 (d, 1H), 5.09–5.49 (m, 5H), 5.73 (d, 1H), 5.85–6.07 (m, 2H), 6.77 (d, 1H), 7.23–7.48 (m, 4H), 7.92 (d, 1H).

Step D

Utilizing the procedures presented in Example 7 (Steps B and C), the alkyl iodide from Step C was displaced by dabco acetamide triflate salt and deallylated to afford the final compound. Purification of the crude product was achieved on reverse-phase HPLC by eluting the compound through a 10 mL column of Amberchrom CG 161 with a linear gradient (100% water to 40:60 CH$_3$CN/H$_2$O over 45 min).

$^1$H NMR (5:2 D$_2$O/CD$_3$CN) δ: 1.41 (d, 6H), 3.59–3.70 (m, 2H), 4.23–4.82 (m, 16H), 5.16 (d, 1H), 5.29 (s, 2H), 5.89 (d, 1H), 7.24 (d, 1H), 7.53 (d, 1H), 7.73–7.89 (m, 3H), 8.51 (d, 1H).

EXAMPLE 18

Preparation of Carbapenem 14

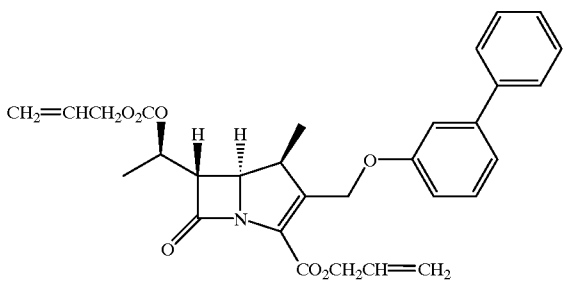

Step A

Preparation of 3-hydroxybiphenyl

A stirred mixture of 660 mg (3 mmol) of 3-iodophenol, 439 mg (3.6 mmol) phenylboronic acid, and 173 mg (0.15 mmol) tetrakistriphenylphosphine in 10 mL of toluene, 5 mL ethanol, and 6 mL 2M sodium carbonate (aqueous) was heated at 100° C. in an inert atmosphere of nitrogen for 15 minutes. The cooled mixture was partitioned between EtOAc, ice, and brine and the organic phase was separated, washed with brine, dried over anhydrous Na$_2$SO$_4$, filtered and evaporated. The residue was purified by plate layer chromatography (PLC) using CH$_2$Cl$_2$ as the eluant to give 430 mg of the title product.

Step B

Following the procedure outlined in Example 2 and using 28.2 mg (0.165 mmol) of 3-hydroxybiphenyl there was obtained after plate layer chromatography using methylene chloride as the eluant, 58.9 mg of carbapenem 14, containing some 3-hydroxybiphenyl, which was used without further purification.

$^1$H NMR (CDCl$_3$) δ: 1.26 (d, J=7.3 Hz,3H), 1.47 (d, J=6.3 Hz, 3H), 3.47 (dd, J=3.0, 11 Hz, 1H-6), 3.50 (m, 1H-1), and 4.2 (dd, J=3.0, 10 Hz, 1H-5).

EXAMPLE 19

Preparation of Carbapenem 15

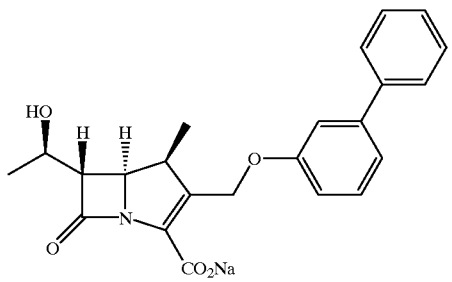

Following the procedure outlined in Example 3 and using the carbapenem derivative prepared in Example 18, 9.4 mg of carbapenem 15 was obtained after purification by reverse phase plate layer chromatography using water-acetonitrile (7:3) as eluant and lyophilization.

IR (nujol): 1750 and 1596 cm$^{-1}$;

$^1$H NMR (D$_2$O—CD$_3$CN,5:2) δ: 1.43 (d, J=7.3 Hz, 3H), 1.5 (d, J=6.3 Hz, 3H), 3.56 (m, 1H-1), 3.62 (dd, J=2.8, 5.7 Hz, 1H-6), 4.36 (dd, J=2.6, 9.9 Hz, 1H-5), 4.45 (m, 1H-8), 5.06 (d, J=13.8 Hz), 1H), 5.85 (d, J=13.8 Hz, 1H), 7.28–7.96 (m, 9 ArH);

UV: λ$_{max}$ 252 nm(H$_2$O).

EXAMPLE 20

Preparation of Carbapenem 16

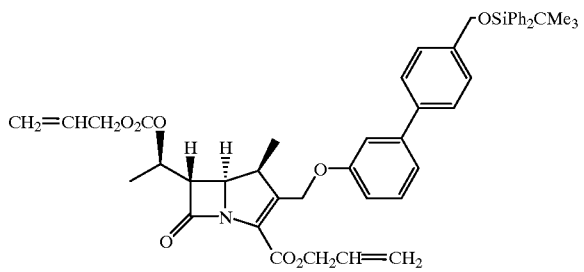

Step A

Preparation of 4'-t-butyldiphenylsilyloxymethyl-3-hydroxybiphenyl

As described in Example 18, step A, 391 mg (1 mmol) of 4-t-butyldiphenylsilyloxymethylboronic acid (prepared as exemplified in U.S. Pat. No. 5,192,758) and 220 mg (1 mmol) of 3-iodophenol gave 354.3 mg of the title compound.

Step B

Following the procedure of Example 2, 153.5 mg (0.35 mmol) of 4'-t-butyldiphenylsilyloxymethyl-3-hydroxybiphenyl was utilized to prepare 89.2 mg of carbapenem 16 containing some of the latter which was used without further purification.

EXAMPLE 21

Preparation of Carbapenem 17

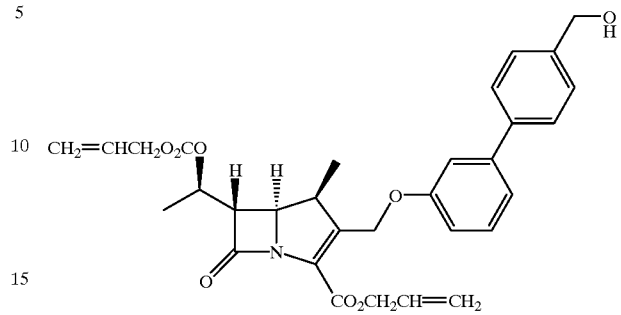

To a stirred solution of carbapenem 16, prepared in Example 20, in 1 mL of THF at 0° C. was added sequentially 19.5 mL (0.34 mmol) of acetic acid and 227 mL (0.23 mmol) of a 1.0 M solution of tetrabutylammonium fluoride in THF. The resulting mixture was stirred with the ice-water bath removed for six hours. The mixture was partitioned between ether, ice-water, and saturated NaHCO$_3$ solution and the organic phase separated, washed with brine, dried over Na$_2$SO$_4$, filtered, and evaporated. Purification by plate layer chromatography using CH$_2$Cl$_2$-EtOAc(10:1) as eluant provided 19.7 mg of carbapenem alcohol.

IR (CH$_2$Cl$_2$): 3604,1779, 1746, and 1719 cm$^{-1}$;

$^1$H NMR (CDCl$_3$) δ: 1.26 (d, J=7.2 Hz,3H), 1.46 (d, J=6.3 Hz, 3H), 1.72 (t, J=5.7 Hz, 1-OH), 3.45 (dd, J=3.0, 8.1 Hz, 1H-6), 3.50 (m, 1H-1), 4.19 (dd, J=3.0, 10 Hz, 1H-5), 5.13 (m, 1H-8) 4.75 (d, J=5.7 Hz, 2H), 6.86–7.6 (m, 8 ArH).

EXAMPLE 22

Preparation of Carbapenem 18

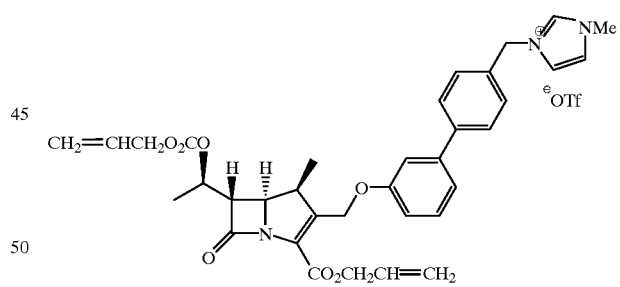

To a stirred solution of 19.7 mg (0.036 mmol) of the carbapenem 17 from Example 21 and 6.3 mL (0.079 mmol) of N-methylimidazole in 1 mL of sieve dried CH$_2$Cl$_2$ at −23° C. in an inert atmosphere of nitrogen was added 6.7 mL (0.0396 mmol) of neat triflic anhydride. The resulting mixture was stirred at −23° C. for 70 minutes and then partitioned between water and CH$_2$Cl$_2$ and the organic phase was separated, dried over Na$_2$SO$_4$, filtered, and evaporated to give 26.3 mg of a colorless foam.

$^1$H NMR (CDCl$_3$) δ: 1.25 (d, J=7.4 Hz,3H), 1.45 (d, J=6.2 Hz, 3H), 3.45 (dd, J=3.0, 8.1 Hz, 1H-6), 3.50 (m, 1H-1), 3.97 (s, N—CH$_3$), 4.19 (dd, J=3.1, 10 Hz, 1H-5), 5.13 (m, 1H-8), 5.4 (s, 2H), 6.88–7.66 (m, 10 ArH), 9.32 (bs, 1H).

EXAMPLE 23

Preparation of Carbapenem 19

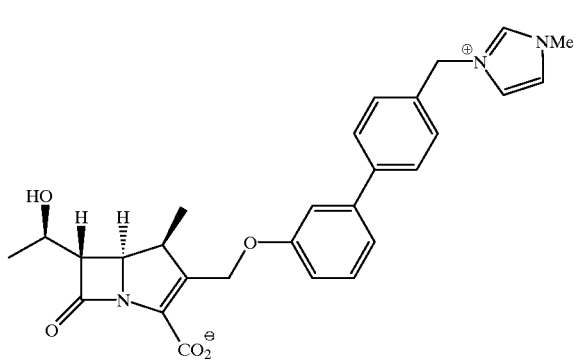

Following the procedure outlined in Example 3, the carbapenem 18 prepared in Example 22 was deallylated to provide 9.5 mg of 19 after purification by reverse phase chromatography (RP-PLC) using water-acetonitrile (7:3) as eluant and lyophilization.

IR (nujol): 1754, 1589 cm$^{-1}$;

$^1$H NMR (D$_2$O—CD$_3$CN,5:2) δ: 1.44 (d, J=7.3 Hz, 3H), 1.5 (d, J=6.5 Hz, 3H), 3.54 (m, 1H-1), 3.62 (dd, J=2.9, 5.7 Hz, 1H-6), 4.14 (s, N—CH$_3$), 4.33 (dd, J=2.6, 9.97 Hz, 1H-5), 4.45 (m, 1H-8), 5.07 (d, J=14.3 Hz), 1H), 5.68 (s, 2H), 5.88 (d, J=14.3 Hz, 1H), 7.3–8.02 (m, 10 ArH);

UV: λ$_{max}$ 258 nm(H$_2$O).

EXAMPLE 24

Preparation of Carbapenem 20

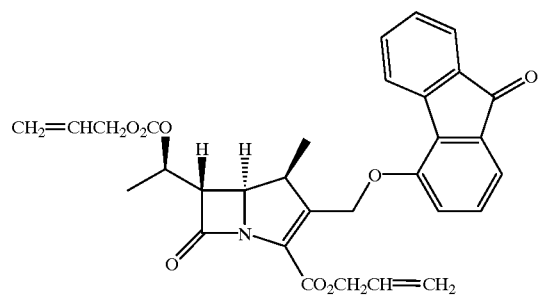

As previously described in Example 2, 33.1 mg (0.168 mmol) of commercially available 4-hydroxyfluoren-9-one gave 44.2 mg of carbapenem 20 containing some of the latter which was used without further purification.

EXAMPLE 25

Preparation of Carbapenem 21

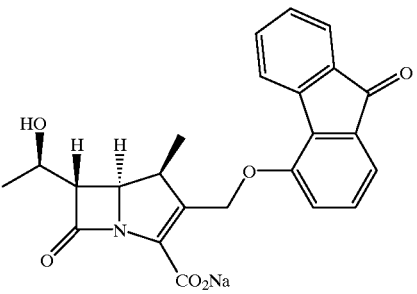

Using the procedure described in Example 3, carbapenem 20 prepared in Example 24 was deallylated to provide 12.5 mg of carbapenem 21 after RP-PLC and lyophilization.

IR (nujol): 1754, 1712, 1593 cm$^{-1}$;

$^1$H NMR (D$_2$O—CD$_3$CN,5:2) δ: 1.48 (d, J=7.3 Hz, 3H), 1.49 (d, J=7.7 Hz, 3H), 3.62 (m, 1H-1), 3.65 (m, 1H-6), 4.42 (m, 1H-5), 4.47 (m, 1H-8), 5.15 (d, J=13.5 Hz), 1H), 5.95 (d, J=13.5 Hz, 1H), 7.5–8.08 (m, 7 ArH);

UV: λ$_{max}$ 253 nm(H$_2$O).

EXAMPLE 26

Preparation of Carbapenem 22

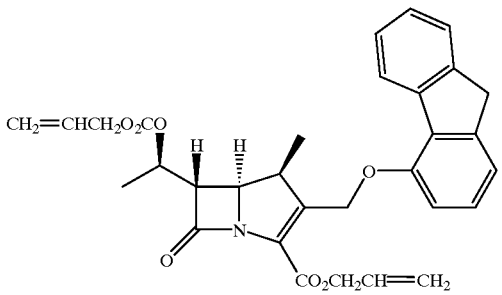

Step A

Preparation of 4-hydroxy-fluorene

A partial solution of 196.2 mg (1 mmol) of 4-hydroxy-fluoren-9-one in 2 mL EtOAc and 3 mL EtOH with 40 mg 10% Pd/C was stirred under a balloon of hydrogen for 27.5 hours. The catalyst was removed by filtration through celite, washed well with EtOAc, and the filtrate evaporated. The residue was purified by plate layer chromatography with CH$_2$Cl$_2$-EtOAc(50:1) to give 102.7 mg of the title substance.

$^1$H NMR (d$_6$-acetone) δ: 3.88 (s, CH$_2$).

Step B

Using the procedure outlined in Example 2, 29.7 mg (0.16 mmol) of 4-hydroxyfluorene, prepared above, provided 57.2 mg of carbapenem 22, which contained a small amount of the latter, and was used without further purification.

$^1$H NMR (CDCl$_3$) δ: 1.28 (d, J=7.3 Hz,3H), 1.43 (d, J=6.3 Hz, 3H), 3.43 (dd, J=3.0, 7.9 Hz, 1H-6), 3.50 (m, 1H-1), 3.91 (s, 2H), 4.17 (dd, J=3.0, 10 Hz, 1H-5), 5.13 (m, 1H-8), 4.91 (d, J=14.1 Hz, 1H), 5.74 (d, J=14.1 Hz), 6.83–8.05 (m, 7ArH).

EXAMPLE 27

Preparation of Carbapenem 23

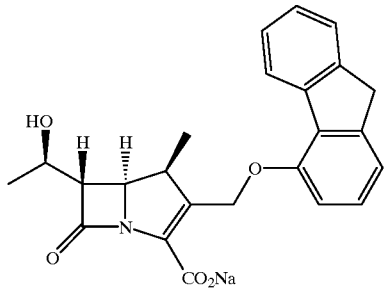

Using the deallylation procedure described in Example 3 and the material prepared in the above example, 19 mg of carbapenem 23 was produced after purification and lyophilization.

IR (nujol): 1753, 1582 cm$^{-1}$;

$^1$H NMR (D$_2$O—CD$_3$CN,5:2) δ: 1.44 (app. d, 6H), 3.61 (m, 1H-1 & 1H-6), 4.17 (s, 2H), 4.33 (m, 1H-5), 4.42 (m, 1H-8), 5.16 (d, J=13.8 Hz), 1H), 5.99(d, J=13.8 Hz, 1H), 7.27–8.42 (m, 7 ArH);

UV: λ$_{max}$ 269 nm(H$_2$O).

EXAMPLE 28

Preparation of Carbapenem 24

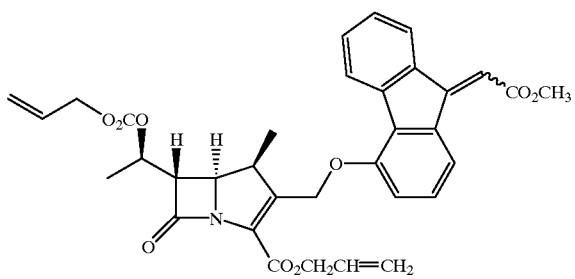

Step A

Preparation of 4-hydroxy-9-carbomethoxy-fluorylidene

A stirred mixture of 401 mg (2 mmol) of 4-hydroxyfluoren-9-one and 1.37 g (4.1 mmol) of methyl-(triphenylphosphoranylidene)-acetate in 10 mL of toluene was refluxed under an atmosphere of nitrogen for 65.5 hours. The cooled reaction mixture was evaporated and the residue purified by plate layer chromatography using CH$_2$Cl$_2$-EtOAc (50:1) as eluant to give 433 mg of the title compound as a mixture of isomers.

$^1$H NMR (CDCl$_3$) δ: 3.87 (s, 3H), 3.88 (s, 3H), 6.74–8.89 (m, 8H).

Step B

As previously described in Example 2, 39.2 mg (0.156 mmol) of fluorylidene prepared in Step A was converted into 75.7 mg of carbapenem 24 as a mixture of isomers and containing some of the latter, which was used without further purification.

$^1$H NMR (CDCl$_3$) δ: 1.25 (m, 3H), 1.42 (d, J=6.3 Hz, 3H), 3.40 (m, 1H-1), 3.43 (m, 1H-6), 3.85 (s, 3H), 3.86 (s, 3H), 4.18 (m, 1H-5), 5.11 (m, 1H-8), 6.7–8.88 (m, 8H).

EXAMPLE 29

Preparation of Carbapenem 25

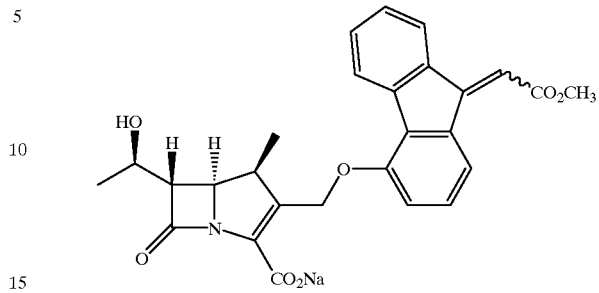

Using the procedure described in Example 3 and the material prepared in Example 28, 15.4 mg of carbapenem 25 was produced as a mixture of geometric isomers.

IR (nujol): 1751, 1717, 1630, 1586 cm$^{-1}$;

$^1$H NMR (D$_2$O—CD$_3$CN,5:2) δ: 1.48 (app. t, 6H), 3.63 (m, 1H-1 & 1H-6), 4.13 (s, 3H), 4.4(m, 1H-5), 4.46 (m, 1H-8), 5.16 (d, J=13.9 Hz), 1H), 5.97(d, J=13.9 Hz, 1H), 7.08–8.88 (m, 8H);

UV:λ$_{max}$ 330, 263 nm(H$_2$O).

EXAMPLE 30

Preparation of Carbapenem 26

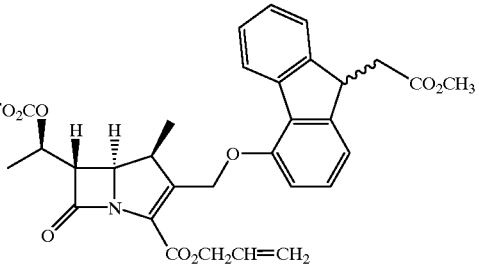

Step A

Preparation of 4-hydroxy-9carbomethoxymethyl-fluorene

A stirred mixture of 348 mg (1.38 mmol) of the fluorylidene derivative prepared in Example 28, Step A, and 50 mg of 10% Pd/C in 10 mL of EtOAc-EtOH (1:1) was hydrogenated under balloon pressure at ambient temperature for 2.5 hours. The catalyst was removed by filtration through celite, washed well with EtOAc, and the filtrate evaporated and dried in vacuo to give 348.5 mg of the title product.

$^1$H NMR (CDCl$_3$) δ: 2.77 (d, J=7.3 Hz, 2H), 3.79 (s, 3H), 4.42 (t, J=7.3 Hz,1H), 5.6 (s, OH), 6.72–8.09 (m, 7ArH).

Step B

As previously described in Example 2, 53 mg (0.208 mmol) of the fluorene derivative prepared above provided after purification by PLC eluting with CH$_2$Cl$_2$-EtOAc (50:1), 88 mg of carbapenem 26, as an equimixture of diastereomers, and containing a little phenolic starting material, which was used without further purification.

$^1$H NMR (CDCl$_3$) δ: 1.28 (d, J=7.3 Hz, 3H), 1.44 (2d's, 3H), 2.75 (2d's, 2H), 3.43 (m, 1H-1 & 1H-6), 3.85 (s, 3H), 3.78 (2s's, 3H), 4.18 (2dd's, 1H-5), 4.41 (t, J=7.3 Hz, 1H), 5.11 (m, 1H-8), 6.84–8.04 (m, 7ArH).

EXAMPLE 31

Preparation of Carbapenem 27

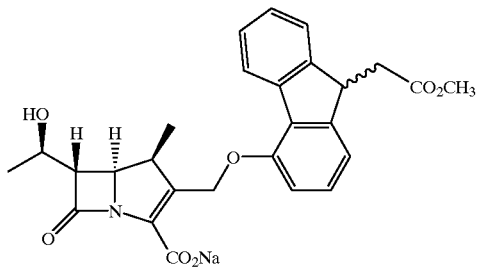

Using the procedure described in Example 3 and the material prepared in the previous example, 28.3 mg of carbapenem 27 was produced after RP-PLC purification and lyophilization.

IR(nujol): 1754, 1737, 1603, 1584 cm$^{-1}$;

$^1$H NMR (D$_2$O—CD$_3$CN,5:2) δ: 1.48 (app. d, 6H), 3.14 (d, J=6.9 Hz, 2H), 3.65 (m, 1H-1 & 1H-6), 3.97 (s, 3H), 4.4 (m, 1H-5), 4.46 (m, 1H-8), 4.63 (t, J=6.9 Hz, 1H), 5.18 (d, J=13.9 Hz), 1H), 5.99(d, J=13.9 Hz, 1H), 7.33–8.42 (m, 7ArH);

UV:λ$_{max}$ 270 nm(H$_2$O).

EXAMPLE 32

Preparation of Carbapenem 28

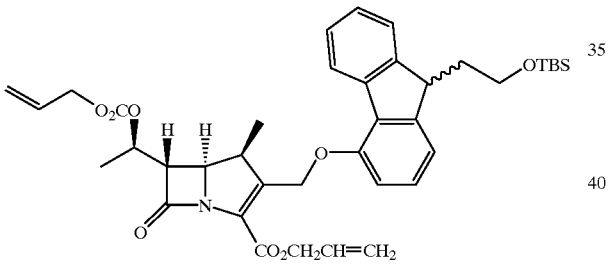

Step A

Preparation of 4-hydroxy-9-hydroxyethyl-fluorene

To a stirred solution of 277.5 mg (1.09 mmol) of the ester prepared in Step A of Example 30 in 5 mL of anhydrous THF at 0° C. was added dropwise 1.1 mL (1.1 mmol) of a 1M solution of lithium aluminum hydride in ether. The resulting mixture was stirred at 0° C. under nitrogen for 1.5 hours and then carefully quenched with Glaubers salt. The mixture was partitioned between EtOAc, ice, 2N HCl, and brine and the organic phase was separated, washed with brine, dried over Na$_2$SO$_4$, filtered, and evaporated. The residue was purified by PLC with CH$_2$Cl$_2$-EtOAc (10:1) to give 236.8 mg of the title compound.

$^1$H NMR (CDCl$_3$) δ: 2.33 (q, J=6.8 Hz, 2H), 3.57 (t, J=6.8 Hz, 2H), 4.13 (t, J=6.8 Hz), 6.08 (s, OH), 6.68–8.13 (m, 7ArH).

Step B

Preparation of 4-hydroxy-9-silyoxyethyl-fluorene

A mixture of 236.8 mg (1.05 mmol) of carbinol, prepared in the previous example, 173.5 mg (1.15 mmol) of t-butyldimethylchlorosilane, and 85.5 mg (1.26 mmol) of imidazole in 5 mL of sieve-dried DMF was stirred at 0° C. under nitrogen for 40 minutes. The mixture was partitioned between EtOAc, ice, 2N HCl, and the organic phase was separated, washed twice with ice-water and then with brine, dried over Na$_2$SO$_4$, filtered, and evaporated. The residue was purified by PLC with CH$_2$Cl$_2$-EtOAc (50:1) to give 325.1 mg of the title compound.

$^1$H NMR (CDCl$_3$) δ: 0.03 (s, 6H), 0.88 (s, 9H), 2.19(m, 2H), 3.67 (t, J=6.8 Hz, 2H), 4.13 (t, J=6.4 Hz), 5.12 (s, OH), 6.71–8.10 (m, 7ArH).

Step C

Using the procedure described in Example 2 and the material prepared in the above example, 478.1 mg of carbapenem 28 was produced as an equimixture of diastereomers after PLC using CH$_2$Cl$_2$-EtOAc (50:1) as eluant.

$^1$H NMR (CDCl$_3$) δ: 0.05 (s, 6H), 0.86 (s, 9H), 1.28 (d, J=7.3 Hz, 3H), 1.44 (d, 3H), 2.14 (m, 2H), 3.44 (m, 1H-1 & 1H-6), 3.65 (m, 2H), 4.11 (m, 1H), 4.20 (2dd's, 1H-5), 5.12 (m, 1H-8), 6.81–8.05 (m, 7ArH).

EXAMPLE 33

Preparation of Carbapenem 29

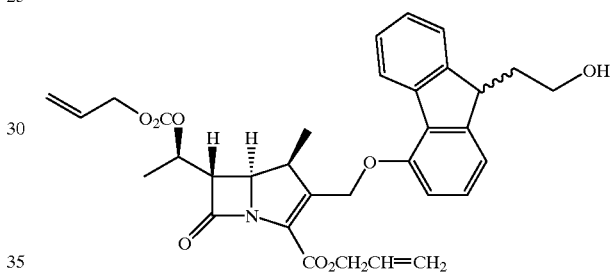

Using the procedure outlined in Step B of Example 5 and the material prepared in the above example, 220.9 mg of the title carbapenem was produced after purification by PLC using CH$_2$Cl$_2$-EtOAc(10:1) as eluant.

$^1$H NMR (CDCl$_3$) δ: 1.28 (2dd's, J=7.3 Hz, 3H), 1.44 (app. t, 3H), 2.29 (m, 2H), 3.46 (m, 1H-1 & 1H-6), 3.56 (m, 2H), 4.12 (m, 1H), 4.20 (2dd's, 1H-5), 5.12 (m, 1H-8), 6.82–8.04 (m, 7ArH).

EXAMPLE 34

Preparation of Carbapenem 30

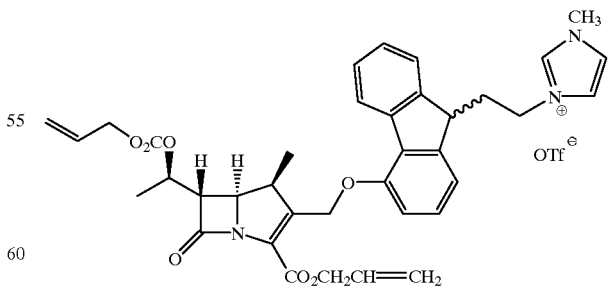

To a stirred mixture of 51.5 mg (0.09 mmol) of carbinol 29, prepared in the previous example, and 16.2 mg (0.2 mmol) of N-methyl-imidazole in 1 mL of sieve-dried CH$_2$Cl$_2$ at 0° C. was added dropwise 27.9 mg (0.99 mmol)

of neat triflic anhydride. The mixture was stirred at 0° C. for 20 minutes and then with the ice-water bath removed for 3 hours. The mixture was partitioned between H₂O and CH₂Cl₂ and the organic phase was separated, dried over Na₂SO₄, filtered, evaporated, and dried in vacuo. The residue was taken up in a minimum amount of CH₂Cl₂ and carbapenem 30 was precipitated by the addition of Et₂O. After decantation of the supernatant and drying in vacuo, 49.7 mg of imidazolium salt 30 was obtained.

$^1$H NMR (CDCl$_3$) δ: 1.26 & 1.30 (2d's, J=7.3 Hz, 3H), 1.42 & 1.45 (2d's, J=6.4 Hz, 3H), 2.87 (m, 2H), 3.34 & 3.60 (2m's, 1H-1), 3.45 (2dd's, 1H-6), 3.72 & 3.73 (2s's, N—CH$_3$), 3.76 (m, 2H), 4.15 & 4.31 (2dd's, 1H-5), 4.2 (m, 1H), 5.12 (m, 1H-8), 6.54–7.99 (m, 9H), 8.6 & 8.66 (2s's, 1H).

EXAMPLE 35

Preparation of Carbapenem 31

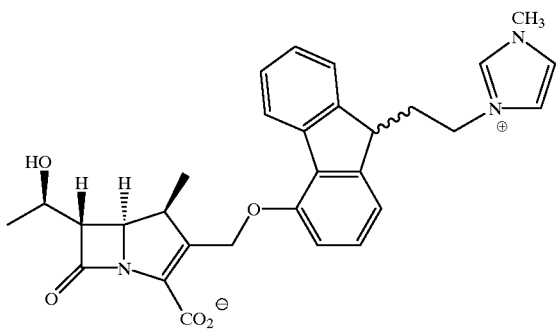

Using the procedure described in Example 3 and the carbapenem prepared in the above example, 14.8 mg of carbapenem 31 was produced.

IR (nujol): 1756, 1595, 1583 cm$^{-1}$;

$^1$H NMR (D$_2$O—CD$_3$CN,5:2) δ: 1.5 (m, 6H), 3.1 (m, 2H), 3.6 (m, 1H-1), 3.7 (2dd's, 1H-6), 3.8(2s's, 3H),4.05 (m, 2H), 4.35–4.45 (m, 3H), 5.18 & 5.25 (2d's, 1H), 5.98 (app. t, 1H), 7.2–8.42 (m, 7ArH);

UV: λ$_{max}$ 271 nm(H$_2$O ).

EXAMPLE 36

Preparation of Carbapenem 32

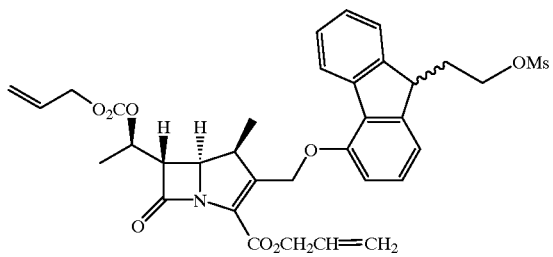

To a stirred solution of 220.9 mg (0.39 mmol) of carbapenem carbinol 29, prepared in Example 33, in 3 mL of sieve dried CH₂Cl₂ at 0° C. was added sequentially 58.5 mg (0.58 mmol) of triethylamine and 57.4 mg (0.5 mmol) of mesyl chloride. The mixture was stirred further for 11 minutes, and the mixture was partitioned between EtOAc, ice, 2N HCl, and brine and the organic phase was separated, washed with brine, dried over Na₂SO₄, filtered, evaporated, and dried in vacuo to give 249.3 mg of carbapenem 32 which was used without further purification.

$^1$NMR (CDCl$_3$) δ: 2.760 & 2.765 (2s's, OSO$_2$CH$_3$).

EXAMPLE 37

Preparation of Carbapenem 33

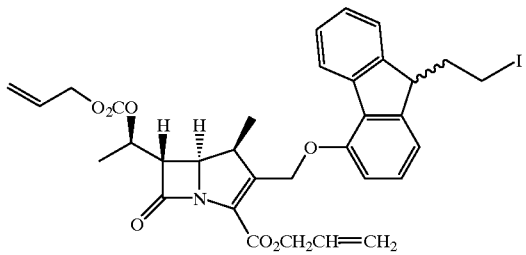

A mixture of 240.8 mg (0.37 mmol) of carbapenem 32, prepared in the previous example, and 249.6 mg (1.6 mmol) of sodium iodide in 3 mL acetone was stirred at a ambient temperature for 55 hours. The mixture was partitioned between EtOAc, ice, 5% aqueous sodium thiosulfate, and brine and the organic phase was separated, washed with brine, dried over Na₂SO₄, filtered, evaporated, and dried in vacuo to give 244.2 mg of carbapenem 33 which was used without further purification.

$^1$H NMR (CDCl$_3$) δ: 2.53 (m, 2H), 3.0 (m, 2H).

EXAMPLE 38

Preparation of Carbapenem 34

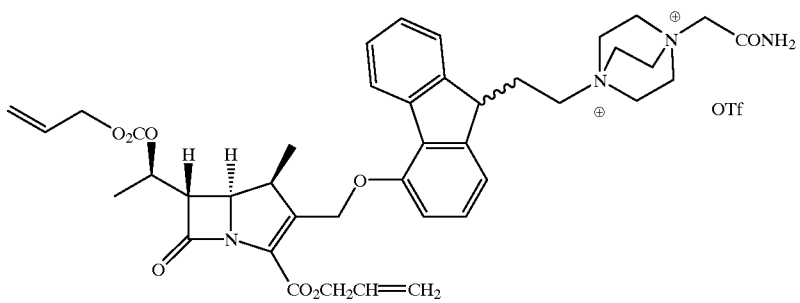

A mixture of 136.6 mg (0.2 mmol) of carbapenem 33, 63.9 mg (0.2 mmol) of N-acetamidodiazoniabicyclooctane triflate, and 51.3 mg (0.2 mmol) of silver triflate in 1.5 mL of acetonitrile was stirred at ambient temperature for 25 hours. The insoluble AgI was removed by filtration through celite, and the filtrate evaporated and dried in vacuo. The residue was taken up in acetone, refiltered, and the filtrate concentrated. Upon the addition of $Et_2O$, the title compound separated, and it was again reprecipitated from acetone, and dried in vacuo to give 150.2 mg of 34, containing some of the starting salt, which was used without further purification.

$^1$H NMR ($d_6$-acetone) δ: 4.27 (m, 6H), 4.49 (m, 6H), 4.61 (m, 2H).

EXAMPLE 39

Preparation of Carbapenem 35

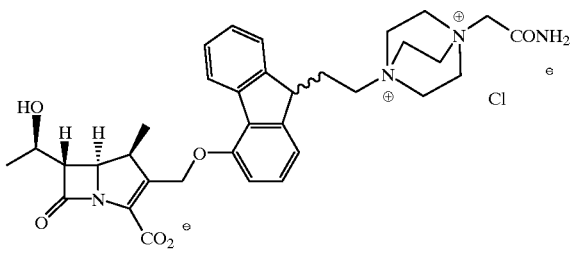

Using the procedure described in Example 3 and carbapenem 34, prepared in the foregoing example, 15.7 mg of carbapenem 35 was produced after purification on macroprep and amberchrom 161 resins.

IR (nujol): 1749, 1695, 1583 cm$^{-1}$;

$^1$H NMR ($D_2O$—$CD_3CN$,5:2) δ: 1.44 (m, 6H), 2.92 (m, 2H), 3.18 (m,2H), 3.5–3.75 (m, 1H-1 & 1H-6), 4.0(m, 6H), 4.35 (m, 6H), 5.07–5.18 (2d's, 1H), 5.88–5.96 (2d's, 1H), 7.28–8.37 (m, 7ArH);

UV: $\lambda_{max}$ 271 nm($H_2O$ ).

EXAMPLE 40

Preparation of Carbapenem 36

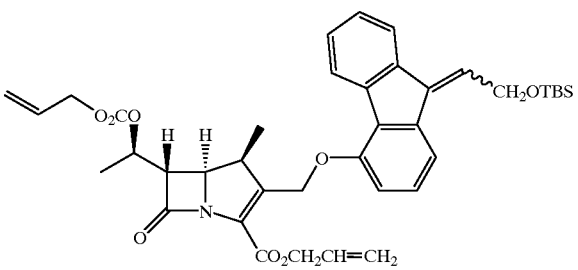

Step A

Preparation of 4-acetoxy-9-(2-t-butyldimethylsilyloxyethyl)-fluorene

To a stirred solution of a mixture of 1.91 g (5.6 mmol) of the phenol, prepared in Step B of Example 32, and 736.6 mg (7.28 mmol) of triethylamine in 20 mL of $CH_2Cl_2$ at 0° C. was added 527.5 mg (6.72 mmol) of neat acetyl chloride and the mixture was stirred further for 0.5 hour. The mixture was partitioned between EtOAc, ice, 1N HCl, and brine and the organic phase was separated, washed with brine, dried over $Na_2SO_4$, filtered, evaporated, and dried in vacuo to give 2.14 g of crude product which was used without further purification.

$^1$H NMR ($CDCl_3$) δ: 0.86 (s, 9H), 2.47 (s, 3H).

Step B

Preparation of 4-acetoxy-9-bromo-9-(2-t-butyldimethylsilyloxyethyl)-fluorene

A mixture of 2.14 g (5.6 mmol) of material prepared in the previous step, 1.2 g (6.72 mmol) of N-bromosuccinimide, and a pinch of AIBN in 20 mL of carbon tetrachloride was refluxed under nitrogen for 1.5 hours. The cooled mixture was partitioned between EtOAc, ice, 5% aqueous sodium thiosulfate, and brine and the organic phase was separated, washed with brine, dried over $Na_2SO_4$, filtered, evaporated, and dried in vacuo to give the crude, title product which was used without further purification.

$^1$H NMR ($CDCl_3$) δ: 0.73 (s, 9H), 2.47 (s, 3H), 2.91 (m, 2H), 3.20 (m, 2H).

Step C

Preparation of 4-acetoxy-9-E,Z-t-butyldimethylsilyloxyethenyl-fluorene

A mixture of the crude product from the previous step, 913 mg (10.9 mmol) of $NaHCO_3$, and 1.54 g (5.98 mmol) of silver triflate in 25 mL DMSO was stirred at room temperature for 15 minutes. The mixture was diluted with EtOAc, filtered through celite to remove the insoluble materials, and washed thoroughly with EtOAc. The filtrate was partitioned between EtOAc, ice, and brine and the organic phase was separated, washed twice with ice-water, and then with brine, dried over $Na_2SO_4$, filtered, evaporated, and dried in vacuo. Purification by PLC eluted with $CH_2Cl_2$-hexanes (1:1) gave 1.22 g of product, as a mixture of geometric isomers.

$^1$H NMR ($CDCl_3$) δ: 0.17 (s, 6H), 0.98 (s, 9H), 2.48 (s, 3H), 5.02 (m, 2H).

Step D

Preparation of 4-hydroxy-9-E,Z-t-butyldimethylsilyloxyethenyl-fluorene

To a stirred, warm solution of 1.19 g (3.13 mmol) of acetate, prepared in the previous step, in 20 mL EtOH was added dropwise 0.77 mL (3.85 mmol) of a 5N solution of sodium hydroxide in water. The resulting dark solution was stirred further for 5 minutes and then partitioned between EtOAc, ice, 1N HCl, and brine. The organic phase was separated, washed with brine, dried over $Na_2SO_4$, filtered, evaporated, and dried in vacuo. Purification by PLC eluted with $CH_2Cl_2$ gave 890.0 mg of product, as a mixture of geometric isomers.

$^1$H NMR ($CDCl_3$) δ: 0.15 (s, 6H), 0.96 (s, 9H), 4.98 (m, 2H), 5.18 & 5.22 (2s's, 1-OH), 6.68–8.1 (m, 8H).

Step E

Using the procedure outlined in Example 2 and 423.7 mg (1.25 mmol) of the mixture of phenols prepared in the previous step, 555 mg of carbapenem 36 was produced which contained a little of the starting phenol and was used without further purification.

$^1$H NMR ($CDCl_3$) δ: 0.15 (s, 6H), 0.95 (s, 9H), 1.27 (d, J=7.3 Hz), 1.43 (d, 6.3 Hz), 3.44 (m, 1H-1 & 1H-6), 4.17 (m, 1H-5), 5.12 (m, 1H-8), 6.77–8.1 (m, 8H).

EXAMPLE 41

Preparation of Carbapenem 37

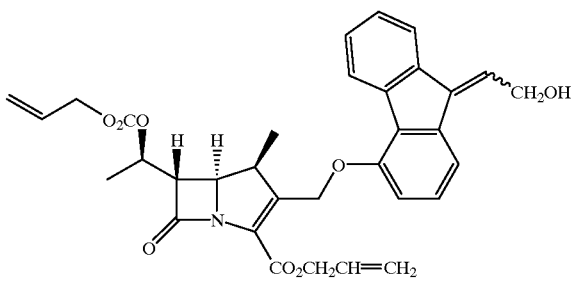

To a stirred solution of a mixture of carbapenem 36, prepared in the prior example, and 292 mg (4.86 mmol) of acetic acid in 10 mL of THF was added 2.43 mL (2.43 mmol) of a 1M solution of tetrabutylammonium fluoride in THF. The mixture was stirred further for 1.25 hour, and then partitioned between EtOAc, ice, saturated $NaHCO_3$ solution, and brine. The organic phase was separated, washed with brine, dried over $Na_2SO_4$, filtered, evaporated, and dried in vacuo. Purification by PLC eluted with $CH_2Cl_2$-EtOAc (10:1) gave 306 mg of product 37, as a mixture of geometric isomers.

$^1$H NMR (CDCl$_3$) δ: 1.27 (d, J=7.3 Hz), 1.43 (d, J=6.3 Hz), 3.44 (m, 1H-1 & 1H-6), 4.18 (m, 1H-5), 5.12 (m, 1H-8), 6.81–8.04 (m, 8H).

EXAMPLE 42

Preparation of Carbapenem 38

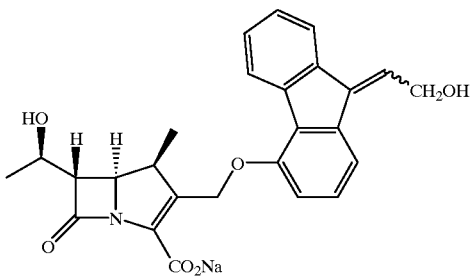

Using the procedure described in Example 3, 27.6 mg (0.048 mmol) of carbapenem 37 in 1 mL of $CH_2Cl_2$-DMF provided 16.2 mg of carbapenem 38 after RP-PLC developed with water-acetonitrile (3:1).

IR (nujol): 1747, 1599 cm$^{-1}$;

$^1$H NMR (D$_2$O—CD$_3$CN,5:2) δ: 1.49 (m, 6H), 3.65 (m, 1H-1 & 1H-6), 4.4 (m, 1H)-5, 4.48 (m, 1H-8), 5.22(m, 3H), 6.03 (m, 1H), 7.17–8.43 (m, 8H);

UV: $\lambda_{max}$ 261 nm(H$_2$O ).

EXAMPLE 43

Preparation of Carbapenem 39

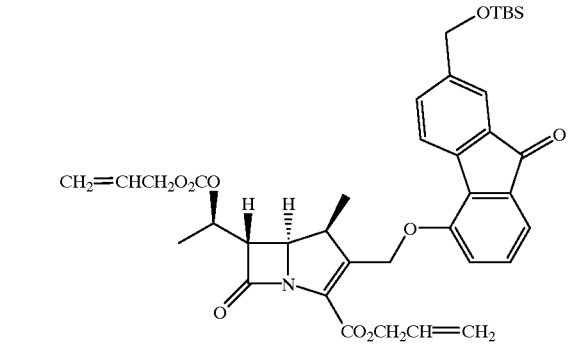

Step A

Preparation of 2-methoxy-6-carbomethoxy-4'-t-butyl-diphenylsilyloxymethylbiphenyl Using the procedure described in Step A of Example 18, 10.0 g (34.2 mmol) of methyl-2-iodo-3-methoxybenzoate (prepared as outlined by W. M. Stanley, E. McMahon, and R. Adams, *J. Amer. Chem. Soc.* 1933, 55, 706) was refluxed for 5 hours to give after chromatography on silica gel with $CH_2Cl_2$-hexanes (2:1) 12.1 g of the title compound.

$^1$H NMR (CDCl$_3$) δ: 1.14 (s, 9H), 3.57 (s, 3H), 3.78 (s, 3H), 7.1–7.77 (m, ArH).

Step B

Preparation of 2-methoxy-4'-hydroxymethylbiphenyl-6-carboxylic acid

A stirred mixture of 6.0 g (11.7 mmol) of biphenyl derivative prepared in Step A and 4.7 mL of 5N NaOH in 100 mL of EtOH was refluxed in an inert atmosphere of nitrogen for 4 hours. The mixture was partitioned between EtOAc, ice, 2N HCl, and the organic phase was separated, washed with brine, dried over $Na_2SO_4$, filtered, evaporated, and dried in vacuo. Upon addition of a little $CH_2Cl_2$ the product crystallized and after the addition of some hexanes 1.95 g of the product was collected by filtration and dried in vacuo.

$^1$H NMR (d$_6$-acetone) δ: 3.74 (s, 3H), 4.64 (s, 2H), 7.17–7.44 (m, 7ArH).

Step C

Preparation of 4-methoxy-7-chloromethyl-fluoren-9-one

To a stirred suspension of 2.0 g (7.74 mmol) of acid prepared in Step B in 40 mL of sieve-dried $CH_2Cl_2$ at 0° C. was added all at once 3.55 g (17.0 mmol) of phosphorous pentachloride and the mixture was stirred further for 5 minutes, and then for 1 hour with the ice-water bath removed. The homogenous solution was recooled to 0° C., and 1.55 g (11.6 mmol) of AlCl$_3$ was added all at once. The resulting mixture was stirred further for 0.5 hour and then partitioned between EtOAc, ice, and brine. The organic phase was separated, washed with brine and saturated NaHCO$_3$, dried over Na$_2$SO$_4$, filtered, evaporated, and dried in vacuo to give 2.04 g of the title material as a yellow solid, which was used without further purification.

IR ($CH_2Cl_2$): 1717.5 cm$^{-1}$;

$^1$H NMR (CDCl$_3$) δ: 3.90 (s, 3H), 4.53 (s, 2H), 6.94–7.68 (m, 6ArH).

Step D

Preparation of 4-methoxy-7-acetoxymethyl-fluoren-9-one

A mixture of 2.0 g (7.7 mmol) of material prepared in Step C and 1.52 g (15.5 mmol) of potassium acetate in 30 mL of DMF was stirred at 100° C. under nitrogen for 36 minutes. The cooled mixture was partitioned between EtOAc and ice-water and the organic phase was separated, washed twice with ice-water, and then with brine, dried over $Na_2SO_4$, filtered, evaporated, and dried in vacuo to give 2.17 g of the title material as a yellow solid, which was used without further purification.

IR ($CH_2Cl_2$): 1742, 1718 cm$^{31\ 1}$;

$^1$H NMR (CDCl$_3$) δ: 2.12 (s, 3H), 3.99 (s, 3H), 5.10 (s, 2H), 7.04–7.81 (m, 6ArH).

Step E

Preparation of 4-methoxy-7-hydroxymethyl-fluoren-9-one

A stirred mixture of the acetate prepared above and 3.07 mL (15.4 mmol) of 5N NaOH in 100° mL of EtOH was refluxed under nitrogen for 10 minutes. The cooled mixture was partitioned between EtOAc, ice-water and 2N HCl, and the organic phase was separated, washed with brine, dried over $Na_2SO_4$, filtered, evaporated, and dried in vacuo to give 2.07 g of the title material as a yellow solid, which was used without further purification.

$^1$H NMR (CDCl$_3$) δ: 3.96 (s, 3H), 4.68 (s, 2H), 7.01–7.77 (m, 6ArH).

Step F

Preparation of 4-methoxy-7-formyl-fluoren-9-one

To a stirred suspension of 1.85 g (7.69 mmol) of carbinol from Step E in 50 mL $CH_2Cl_2$ was added 270.1 mg (0.769 mmol) of tetrapropylammonium perruthenate. After stirring for 5 minutes, 1.35 g (11.5 mmol) of solid N-methyl-morpholine-N-oxide was added all at once, and the resulting mixture stirred further for 5 minutes. The dark solution was passed over a column of florisil eluted with $CH_2Cl_2$-EtOAc (10:1) to give 1.42 g of the title aldehyde as a yellow solid.

IR ($CH_2Cl_2$): 1720, 1698 cm$^{-1}$;

$^1$H NMR (CDCl$_3$) δ: 4.02 (s, 3H), 7.09–8.1 (m, 6ArH), 10.0 (s, 1H).

Step G

Preparation of 4-hydroxy-7-formyl-fluoren-9-one

A stirred mixture of the methylether from the previous step and 30 mL of 48% HBr in 15 mL of acetic acid was heated at 130° C. under nitrogen for 7 hours. The cooled mixture was poured onto ice-water and the separated product collected by suction filtration, washed well with water, and dried in vacuo to give 0.94 g of the title compound.

$^1$H NMR (d$_6$-acetone) δ: 7.18–8.15 (m, 6ArH), 9.8 (s, 1-OH), 10.07 (s,1-CHO).

Step H

Preparation of 4-hydroxy-7-hydroxymethyl-fluoren-9-one

A stirred mixture of 405.2 mg (1.8 mmol) of aldehyde prepared in Step G and 804.3 mg (3.8 mmol) of sodium triacetoxyborohydride in 27 mL of anhydrous THF was refluxed under nitrogen for 1 hour. The cooled mixture was partitioned between EtOAc, ice-water and saturated NaHCO$_3$, and the organic phase was separated, washed with brine, dried over Na$_2$SO$_4$, filtered, evaporated, and dried in vacuo. Purification by PLC with $CH_2Cl_2$-EtOAc (2:1) yielded 303.7 mg of the crystalline, title product.

$^1$H NMR (d$_6$-acetone) δ: 4.66 (s,2H), 7.08–7.86 (m, 6ArH), 9.38 (s, 1-OH).

Step I

Preparation of 4-hydroxy-7-t-butyldimethylsilyloxymethyl-fluoren-9one

A mixture of 332.2 mg (1.47 mmol) of the diol from Step H, 243.5 mg (1.61 mmol) of t-butyldimethylchlorosilane, and 120 mg (1.76 mmol) of imidazole in 8 mL of sieve dried DMF was stirred at 100° C. for 45 minutes. The mixture was partitioned between EtOAc, ice-water and 2N HCl, and the organic phase was separated, washed twice with ice-water, and then with brine, dried over Na$_2$SO$_4$, filtered, evaporated, and dried in vacuo. Purification by PLC using $CH_2Cl_2$-EtOAc (50:1) gave 447.4 mg of the title material.

$^1$H NMR (d$_6$-acetone) δ: 0.14 (s, 6H), 0.95 (s, 9H), 4.81 (s,2H), 7.08–7.86 (m, 6ArH), 9.35 (bs, 1-OH).

Step J

Using the procedure given in Example 2, 127.1 mg (0.37 mmol) of the phenol prepared in Step I provided 99.5 mg of carbapenem derivative 39 which contained a little of the latter and some SN2' product and was used without further purification.

$^1$H NMR (CDCl$_3$) δ: 0.1 (s, 6H), 0.93 (s, 9H), 1.27 (d, J=7.3 Hz), 1.43 (d, 6.3 Hz), 3.44 (m, 1H-1 & 1H-6), 4.21 (dd, 1H-5), 5.12 (m, 1H-8), 6.86–7.76 (m, 6H).

EXAMPLE 44

Preparation of Carbapenem 40

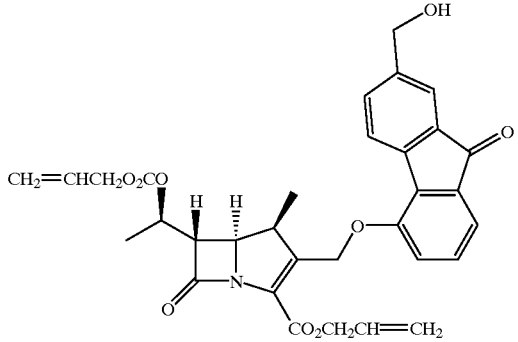

Using the procedure detailed in Example 5, Step B, the carbapenem prepared in the previous example was desilylated to provide 52.7 mg of carbapenem 40 after PLC with $CH_2Cl_2$-EtOAc (2:1).

$^1$H NMR (CDCl$_3$) δ:1.29 (d, J=7.4 Hz), 1.45 (d, 6.3 Hz), 3.44 (m, 1H-1 & 1H-6), 4.22 (dd, 1H-5), 5.13 (m, 1H-8), 7.0–7.78 (m, 6H).

EXAMPLE 45

Preparation of Carbapenem 41

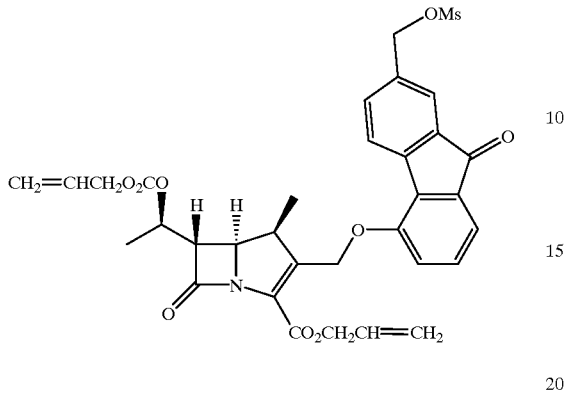

Using the procedure described in Example 36, the carbapenem prepared in Example 44 was converted into the corresponding mesylate 41 (59 mg).

$^1$H NMR (CDCl$_3$) δ:1.27 (d, J=7.4 Hz, 3H), 1.45 (d, J=6.3 Hz, 3H), 3.0 (s, 3H), 3.44 (m, 1H-1 & 1H-6), 4.22 (dd, 1H-5), 4.90 (d, J=14.8 Hz, 1H), 5.13 (m, 1H-8), 5.24 (s, 2H), 5.73 (d, J=14.8 Hz, 1H), 7.03–7.82 (m, 6H).

EXAMPLE 46

Preparation of Carbapenem 42

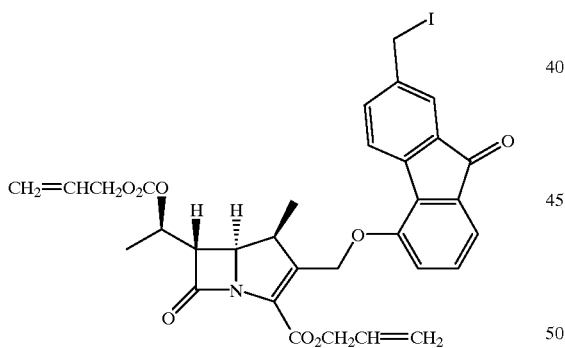

Carbapenem 41 (58.7 mg, 0.09 mmol) and 27.1 mg (0.18 mmol) of sodium iodide in 1mL of acetone was stirred at 0° C. for 1.25 hour. The mixture was partitioned between EtOAc, ice-water and brine, and the organic phase was separated, washed with brine, dried over Na$_2$SO$_4$, filtered, evaporated, and dried in vacuo to give 63.3 mg of carbapenem 42; as a yellow foam, which was used without further purification.

$^1$H NMR (CDCl$_3$) δ:1.30 (d, J=7.2 Hz, 3H), 1.45 (d, J=6.3 Hz, 3H), 3.44 (m, 1H-1 & 1H-6), 4.22 (dd, 1H-5), 4.47 (s,2H), 4.90 (d, J=14.8 Hz, 1H), 5.13 (m, 1H-8), 5.24 (s, 2H), 5.73 (d, J=14.8 Hz, 1H), 7.01–7.78 (m, 6H).

EXAMPLE 47

Preparation of Carbapenem 43

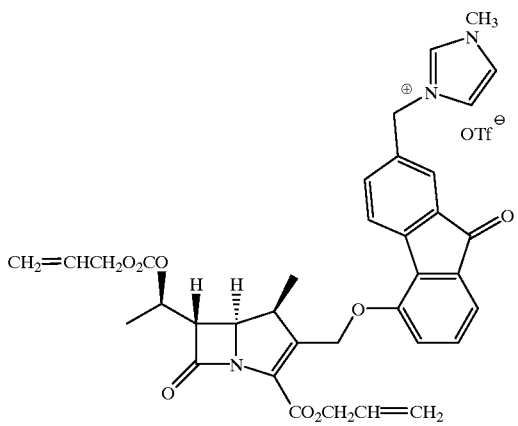

Using the procedure described in Example 22, 40.5 mg (0.07 mmol) of carbapenem 40 provided 55.5 mg of salt 43.

$^1$H NMR (CDCl$_3$) δ:1.26 (d, J=7.3 Hz, 3H), 1.41 (d, J=6.2 Hz, 3H), 3.44 (m, 1H-1 & 1H-6), 3.96 (s, N—CH$_3$), 4.2 (dd, 1H-5), 5.13 (m, 1H-8), 5.39 (s, 2H), 5.65 (d, J=14.7 Hz, 1H), 6.97–7.70 (m, 8H), 9.29 (s, 1H).

EXAMPLE 48

Preparation of Carbapenem 44

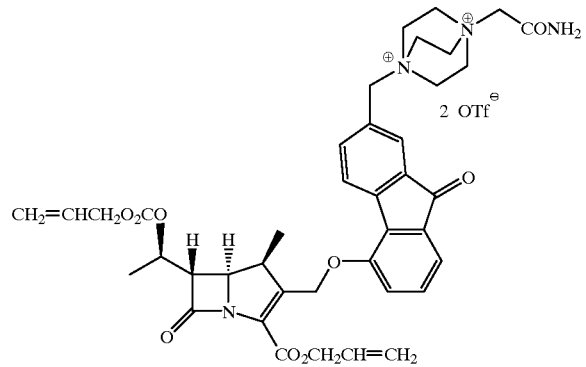

Using the procedure of Example 38, the carbapenem 38 prepared in Example 42 in 1 mL acetonitrile after 0.5 hour was converted to 88.2 mg of carbapenem 44, which contained a little of the dabco acetamide starting material and was used without further purification.

$^1$H NMR (d$_6$-acetone) δ: 1.38 (app t, 6H), 4.4 (m, 6H), 4.54 (m, 6H), 4.64 (s, 2H), 5.14 (s, 2H), 5.69 (d, J=13.8 Hz, 1H), 7.3–8.05 (m, 6H).

EXAMPLE 49

Preparation of Carbapenem 45

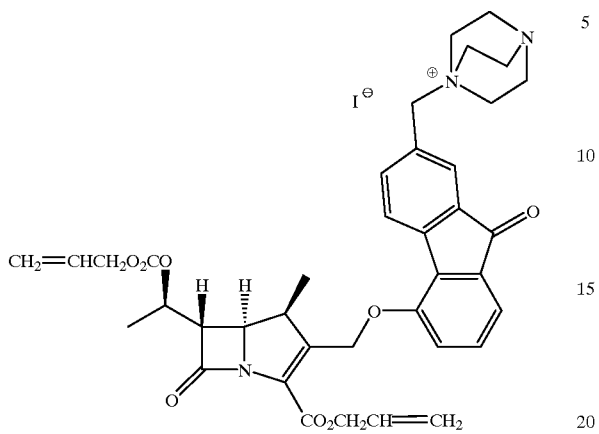

A mixture of 77.8 mg (0.114 mmol) of carbapenem iodide 42 and 12.8 mg (0.114 mmol) of dabco in 1 mL acetonitrile was stirred at room temperature for 0.5 hour and then at 0° C. for 1.25 hour. The acetonitrile was evaporated and the residue partitioned between water and methylene chloride. The methylene chloride layer was separated, dried over sodium sulfate, filtered, and evaporated to give 86.4 mg of carbapenem 45.

$^1$H NMR (CDCl$_3$) δ: 1.29 (d, J=7.3 Hz,3H), 1.44 (d, J=6.4 Hz, 3H), 3.19 (m, 6H), 3.75 (m,6H), 3.44 (m, 1H-1 & 1H-6), 4.28 (dd, 1H-5), 5.45 (d, J=14.5 Hz, 1H), 5.65 (d, J=14.5 Hz, 1H), 6.93–7.92 (m, 8H).

EXAMPLE 50

Preparation of Carbapenem 46

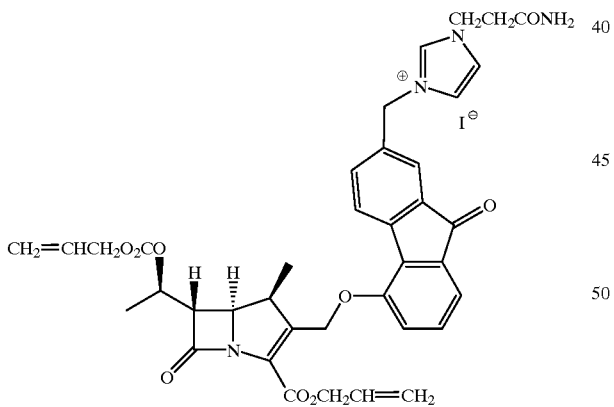

To a solution of 102.2 mg (0.15 mmol) of carbapenem iodide 42 in 1 mL of acetonitrile was added a solution of 22.9 mg (0.165 mmol) of N-2-carboxamidoethylimidazole in 0.275 mL DMF and 0.085 mL methanol and the mixture was stirred at room temperature for 19 hours. The volatiles were evaporated and the residue taken up in minimum amount of methylene chloride and the product precipitated by the addition of Et$_2$O. Repetition of this process and drying gave 116.1 mg of carbapenem 46.

$^1$H NMR (CDCl$_3$) δ: 1.28 (d, J=7.2 Hz,3H), 1.44 (d, J=6.3 Hz, 3H), 3.16 (m, 2H), 3.44 (m, 1H-1 & 1H-6), 4.27 (dd, 1H-5), 4.64 (m,2H), 5.59 (s, 2H), 6.21 (bs, 2NH), 6.93–7.8 (m, 8H), 9.82 (bs, 1H).

EXAMPLE 51

Preparation of Carbapenem 47

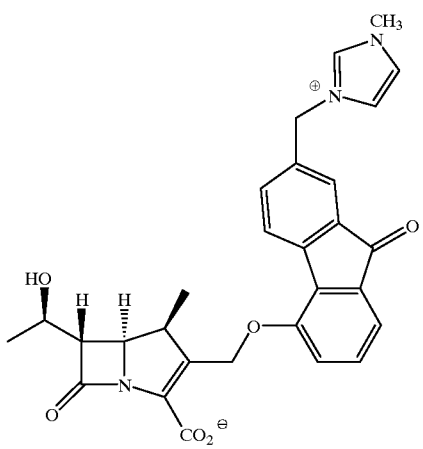

Following the procedure outlined in Example 3, the carbapenem 43 prepared in Example 47 was deallylated to provide 11.4 mg of 47 after purification by reverse phase chromatography (RP-PLC) using water-acetonitrile (7:3) as the eluant and lyophilization.

IR (nujol): 1751, 1716, 1593 cm$^{-1}$;

$^1$H NMR (D$_2$O—CD$_3$CN,5:2) δ: 1.39 (d, J=7.4 Hz, 3H), 1.45 (d, J=6.4 Hz, 3H), 3.54 (m, 1H-1), 3.59 (dd, J=2.8 5.7 Hz, 1H-6), 4.09 (s, N—CH$_3$), 4.45 (m, 1H-5 & 1H-8), 5.0 (d, J=13.6 Hz, 1H), 5.58 (s, 2H), 5.78 (d, J=13.6 Hz, 1H), 7.31–7.93 (m, 8ArH);

UV: $\lambda_{max}$ 256 nm(H$_2$O).

EXAMPLE 52

Preparation of Carbapenem 48

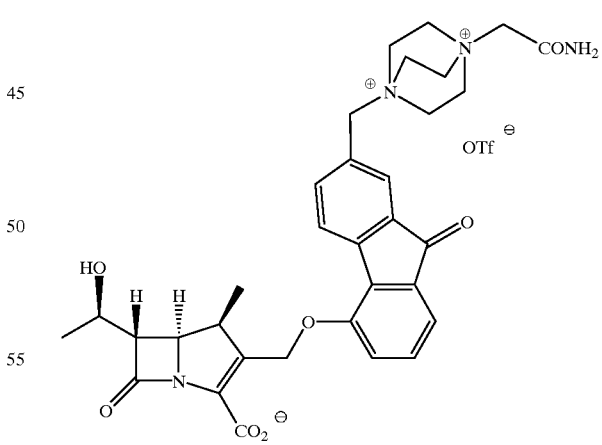

Using the procedure described in Example 7, Step C, and carbapenem 44, prepared in the Example 48, 7.6 mg of carbapenem 48 was produced with Et$_2$O precipitation and purification on amberchrom 161 resin.

IR (nujol): 1747, 1706, 1688, 1591 cm$^{-1}$;

$^1$H NMR (D$_2$O—CD$_3$CN,5:2) δ: 1.47 (d, J=7.2 Hz, 3H), 1.52 (d, J=6.3 Hz, 3H), 3.61–3.70 (m, 1H-1 & 1H-6), 4.27

(m, 6H), 4.47 (m, 6H), 5.07–5.18 (2d's, 1H), 5.88–5.96 (2d's, 1H), 7.28–8.37 (m, 7ArH);

UV: $\lambda_{max}$ 268 nm(H$_2$O).

EXAMPLE 53

Preparation of Carbapenem 49

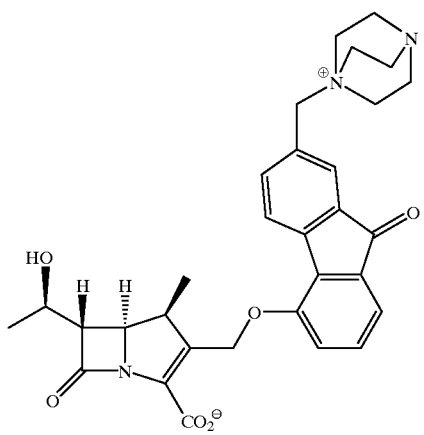

Using the procedure described in Example 3, except the solvent was DMF, and carbapenem 46, prepared in Example 50, 20 mg of carbapenem 49 was produced.

IR (nujol): 1754, 1711, 1595 cm$^{-1}$;

$^1$H NMR (D$_2$O—CD$_3$CN,5:2) δ: 1.43 (d, J=6.9 Hz, 3H), 1.48 (d, J=6.3 Hz, 3H), 3.37 (m, 6H), 3.62 (m, 6H), 4.68 (bs, 2H), 5.06 (d, J=13.4 Hz,1H), 5.83 (d, J=13.4 Hz,1H), 7.38–8.0 (m, 6ArH);

UV: $\lambda_{max}$ 257 nm(H$_2$O).

EXAMPLE 54

Preparation of Carbapenem 50

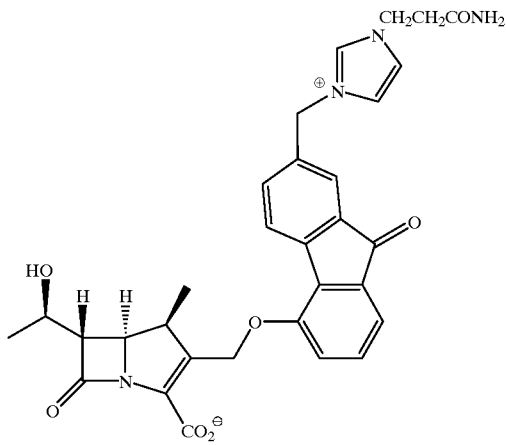

Using the procedure described in Example 3, except the solvent was DMF, and carbapenem 45, prepared in the Example 49, 34.8 mg of carbapenem 50 was produced.

IR (nujol): 1755, 1715,1688,1678,1592 cm$^{-1}$;

$^1$H NMR (D$_2$O—CD$_3$CN, 5:2) δ: 1.39 (d, J=6.2 Hz, 3H), 1.45 (d, J=6.3 Hz, 3H), 3.08 (t, J=6.5 Hz, 2H), 3.52 (m, 1H-1), 3.6 (dd, 1H-6), 4.4 (m, H-5 & H-8), 4.68 (t, J=6.5 Hz, 2H), 5.0 (d, J=13.8 Hz,1H), 5.58 (s, 2H), 5.75 (d, J=13.3 Hz,1H), 7.28–7.9(m, 8ArH);

UV: $\lambda_{max}$ 257 nm(H$_2$O).

EXAMPLE 55

Preparation of Carbapenem 51

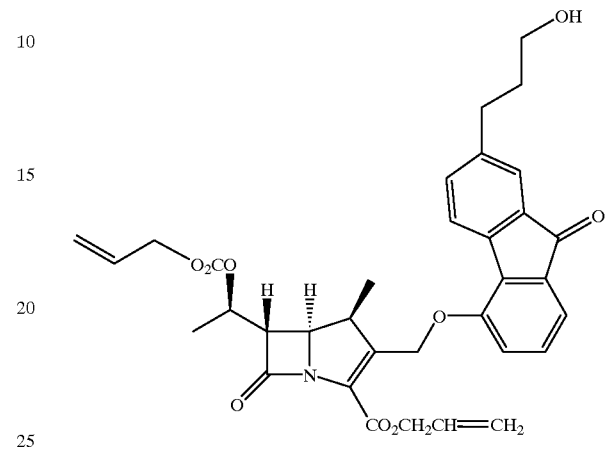

Step A

Preparation of 4-acetoxy-7-formyl-fluoren-9-one

To a stirred suspension of 1.53 g (6.83 mmol) of 4-hydroxy-7-formyl-fluoren-9-one, prepared in Step G of Example 43, in 25 mL THF at 0° C. was added 1.24 mL (8.88 mmol) of triethylamine and 0.58 mL (8.2 mmol) of acetyl chloride. The mixture was stirred further for 0.5 hour and then partitioned between EtOAc, ice, 1N HCl, and brine. The organic phase was separated, washed with brine, dried over Na$_2$SO$_4$, filtered, evaporated, and dried in vacuo. Purification by chromatography on silica gel using methylene chloride as eluant gave 1.46 g of the title compound.

IR (CH$_2$Cl$_2$): 1772, 1724, 1702, 1618,1606 cm$^{-1}$;

$^1$H NMR (CDCl$_3$) δ: 2.48 (s, 3H), 7.38–8.15 (m, 6ArH), 10.0 (s, 1H).

Step B

Preparation of 4-acetoxy-7-(E-2-carbomethoxyvinyl)-fluoren-9-one

A mixture of 1.46 g (5.49 mmol) of aldehyde, prepared in Step A, and 2.02 g (6.04 mmol) of methyl-(triphenylphosphoranylidene)-acetate in 25 mL of methylene chloride was stirred at room temperature for 1 hour, during which time product precipitation was progressive. Ether-hexanes (2:1, 20 mL) was added and the yellow solid was collected by suction filtration, washed with 60 mL of ether-hexanes (2:1), and dried in vacuo to give 1.43 g of the title material.

$^1$H NMR (CDCl$_3$) δ: 2.48 (s, 3H), 3.82 (s, 3H), 6.49 (d, J=16 Hz, 1H), 7.30–7.87 (m, 6ArH), 7.68 (d, J=16 Hz, 1H).

Step C

Preparation of 4-acetoxy-7-(2-carbomethoxyethyl)-fluoren-9-one

The material prepared above in Step B, 1.11 g (3.45 mmol) and 267 mg of 5% Rh/C in 60 mL methylene chloride and 12 mL methanol was stirred under balloon pressure of hydrogen for 5 hours. The catalyst was removed by filtration through celite, washed well with methylene chloride, and the filtrate evaporated and dried in vacuo to give 1.1 g of product which was used without further purification.

$^1$H NMR (CDCl$_3$) δ: 2.46 (s, 3H), 2.65 (t, J=7.5 Hz, 2H), 2.98 (t, J=7.5 Hz, 2H), 3.67 (s, 3H), 7.23–7.56 (m, 6ArH).

Step D

Preparation of 2-(4-hydroxy-7-fluoren-9-one) propionic acid

A stirred mixture of 1.27 g (3.92 mmol) of ester, prepared in Step C above, and 2.43 mL (12.2 mmol) of 5N NaOH in 30 mL of EtOH was refluxed under nitrogen for 70 minutes. The cooled mixture was partitioned between EtOAc, ice, 2N HCl, and brine, and the organic phase was separated, washed with brine, dried over Na$_2$SO$_4$, filtered, evaporated, and dried in vacuo to give 1.04 g of the title acid.

$^1$H NMR (d$_6$-acetone) δ: 2.67 (t, J=7.5 Hz, 2H), 2.97 (t, J=7.5 Hz, 2H), 7.08–7.80 (m, 6ArH), 9.37 (s, bs, 1H).

Step E

Preparation of 4-hydroxy-7-(3-hydroxypropyl)-fluoren-9-ol

To a stirred suspension of the acid (905.1 mg, 3.38 mmol), prepared above in Step D, in 30 mL of anhydrous THF at ambient temperature was added cautiously 10.1 mL of 1M borane-THF in THF. The resulting mixture was stirred further for 2 hours and carefully quenched with methanol. The mixture was evaporated and the residue partitioned between EtOAc, ice, saturated NaHCO$_3$, and brine, and the organic phase was separated, washed with brine, dried over Na$_2$SO$_4$, filtered, evaporated, and dried in vacuo to give 0.96 g of the title triol.

$^1$H NMR (d$_6$-acetone) δ: 1.85 (m, 2H), 2.74 (t, J=7.4 Hz, 2H), 3.60 (t, J=7.4 Hz, 2H), 5.49 (d, J=6.1 Hz, 1H), 6.83–7.91 (m, 6ArH), 8.88 (s, 1H).

Step F

Preparation of 4-hydroxy-7-(3-hydroxypropyl)-fluoren-9-one

A stirred mixture of 870 mg (3.38 mmol) of triol, prepared in Step E, and 958 mg (13.5 mmol) of manganese dioxide in 20 mL of acetone was refluxed for 17 hours. The cooled mixture was filtered through celite, washed well with acetone, and the filtrate evaporated and dried in vacuo to give 832.2 mg of the title compound, as a brick-red solid.

$^1$H NMR (d$_6$-acetone) δ: 1.85 (m, 2H), 2.74 (t, J=7.4 Hz, 2H), 3.59 (m, 2H), 7.06–7.79 (m, 6ArH), 9.30 (s,1H).

Step G

Preparation of 4-hydroxy-7-(3-t-butyldimethylsilyloxypropyl)-fluoren-9-one

A mixture of 832.2 mg (3.28 mmol) of diol, prepared in Step F above, 543.2 mg (3.6 mmol) of t-butyldimethylchlorosilane, and 267.7 mg (3.9 mmol) of imidazole in 10 mL sieve-dried DMF was stirred at 0° C. for 45 minutes. The mixture was partitioned between EtOAc, ice, and 2N HCl, and the organic phase was separated, washed twice with ice-water and then with brine, dried over Na$_2$SO$_4$, filtered, and evaporated. The residue was purified by silica gel chromatography using an elution gradient of methylene chloride-ethyl acetate (50:1 to 10:1) to give 1.05 g of the title product.

$^1$H NMR (CDCl$_3$) δ: 0.04 (s, 6H), 0.89 (s, 9H), 1.84 (m, 2H), 2.68 (t, J=6.3 Hz, 2H), 3.62 (t, J=6.3 Hz, 2H), 5.25 (bs, 1H),5.7 (d, J=15 Hz, 1H), 6.98–7.61 (m, 6ArH)

Step H

Mitsunobu Reaction

Using the general procedure described in Example 2 and 109.8 mg (0.3 mmol) of phenol, prepared in Step G, 165.4 mg of the carbapenem adduct was produced.

$^1$H NMR (CDCl$_3$) δ: 0.03 (s, 6H), 0.89 (s, 9H), 1.27 (d, J=7.3 Hz, 3H), 1.43 (d, J=6.3 Hz, 3H), 1.84 (m, 2H), 2.68 (t, J=7.6 Hz, 2H), 3.44 (m, 1H-1 & 1H-6), 3.62 (t, J=6.2 Hz, 2H), 4.21 (dd, 1H-5), 5.12 (m, 1H-8), 5.7 (d, J=15 Hz, 1H), 6.86–7.76 (m, 6H).

Step I

Desilylation

Using the general procedure outlined in Example 21, the carbapenem prepared in the previous step provided 103.4 mg of carbapenem 51.

$^1$H NMR (CDCl$_3$) δ: 1.27 (d, J=7.3 Hz, 3H), 1.43 (d, J=6.3 Hz, 3H), 1.87 (m, 2H), 2.72 (t, J=7.3 Hz, 2H), 3.44 (m, 1H-1 & 1H-6), 3.67 (t, J=6.3 Hz, 2H), 4.21 (dd, 1H-5), 5.12 (m, 1H-8), 5.7 (d, J=15 Hz, 1H), 6.97–7.62 (m, 6H).

EXAMPLE 56

Preparation of Carbapenem 52

Step A

Triflate Formation

Using the general procedure outlined in Step A of Example 10, 58.2 mg (0.097 mmol) of alcohol 51, prepared in Example 55, was converted into 70.4 mg of the corresponding triflate.

Step B

Displacement Reaction

Using the general procedure outlined in Step B of Example 10, the crude triflate from Step A was converted into 81.3 mg of crude carbapenem 52, which was used without further purification.

EXAMPLE 57

Preparation of Carbapenem 53

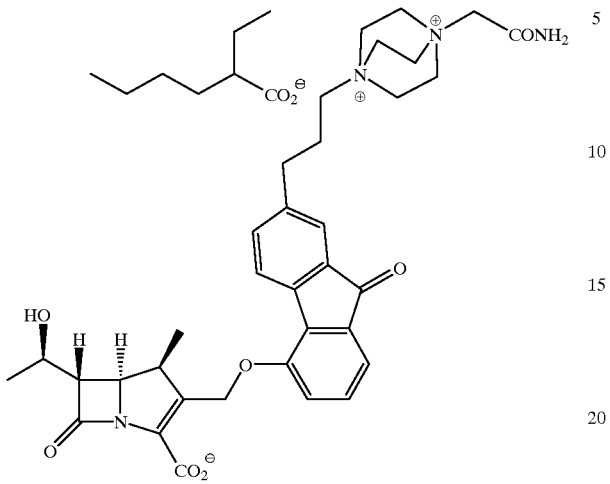

Using the general procedure outlined in Step C of Example 7, the crude carbapenem salt 52 was converted into 20.3 mg of carbapenem 53, after resin chromatography on amberchrom CG 161.

IR (nujol): 1753, 1704,1592 cm$^{-1}$;

$^1$H NMR (D$_2$O—CD$_3$CN, 5:2) δ: 1.09 (m), 1.43 (d, J=7.4 Hz, 3H), 1.48 (d, J=6.3 Hz, 3H), 1.65 (m), 2.94 (m, 2H), 3.56 (m, 1H-1), 3.63 (dd, 1H-6), 3.83 (m), 4.2 (m), 4.45 (m), 5.01 (d, J=14 Hz,1H), 5.58 (s, 2H), 5.8 (d, J=14 Hz,1H), 7.36–7.83(m, 8ArH);

UV: λ$_{max}$ 257 nm(H$_2$O ).

EXAMPLE 58

Preparation of Carbapenem 54

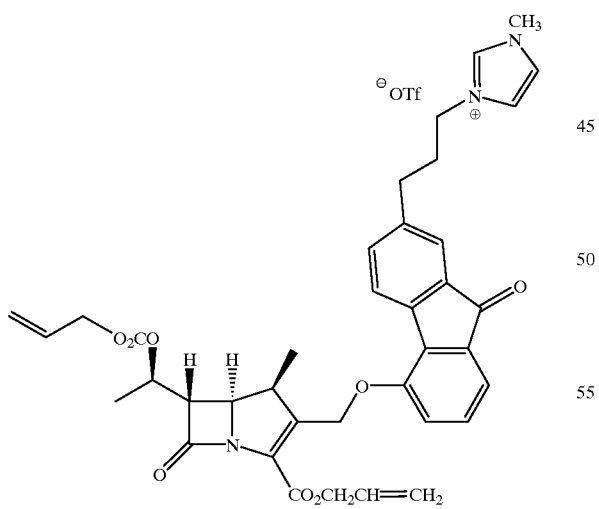

Using the procedure described in Example 22, 48.7 mg (0.08 mmol) of carbapenem 51 provided 54.3 mg of salt 54.

$^1$H NMR (CDCl$_3$) δ: 1.29 (d, J=7.4 Hz,3H), 1.44 (d, J=6.3 Hz, 3H), 2.25 (m, 2H), 2.72 (m, 2H), 3.44 (m, 1H-1 & 1H-6), 3.98 (s, N—CH$_3$), 5.13 (m, 1H-8), 5.68 (d, J=14.9 Hz, 1H), 6.99–7.65 (m, 8H), 9.2 (s, 1H).

EXAMPLE 59

Preparation of Carbapenem 55

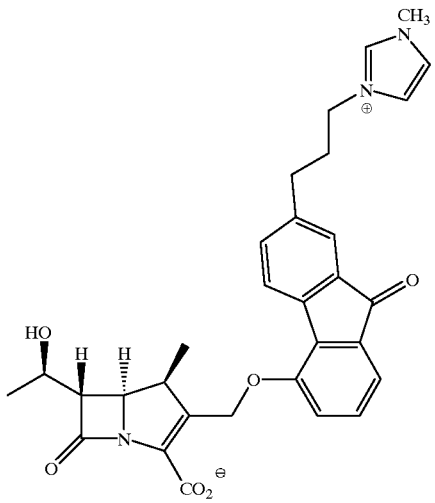

Following the procedure outlined in Example 3, the carbapenem 54 prepared in Example 58 was deallylated to provide 14 mg of 55 after purification by reverse phase chromatography (RP-PLC) using water-acetonitrile (7:3) as eluant and lyophilization.

IR (nujol): 1753, 1709, 1594 cm$^{-1}$;

$^1$H NMR (D$_2$O—CD$_3$CN,5:2) δ: 1.43 (d, J=7.4 Hz, 3H), 1.48 (d, J=6.3 Hz, 3H), 2.38 (m, 2H), 2.87 (m, 2H), 3.54 (m, 1H-1), 3.62 (dd,1H-6), 4.06 (s, N—CH$_3$), 4.45 (m, 4H), 5.05 (d, J=14.3 Hz, 1H), 5.84 (d, J=14.3 Hz, 1H), 7.36–7.81 (m, 8ArH), 8.9 (bs, 1H).

UV: λ$_{max}$ 258 nm(H$_2$O).

EXAMPLE 60

Preparation of Carbapenem 56

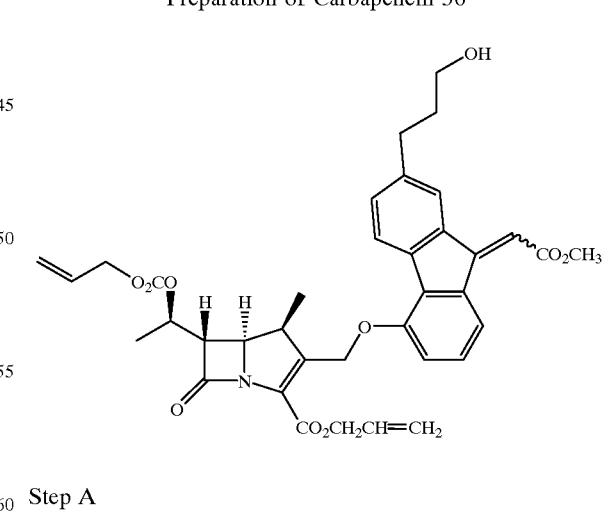

Step A

Preparation of 4-hydroxy-7-(3-t-butyldimethylsilyloxypropyl)-9-carbomethoxy-fluorylidene A stirred mixture of 110.4 mg (0.3 mmol) of fluorenone derivative prepared in Step G of Example 55 and 250.8 mg (0.75 mmol) of methyl-(triphenylphosphoranylidene)- acetate in 3 mL of p-xylene was refluxed under nitrogen for 21 hours. The cooled mixture was evaporated and the residue purified by PLC with $CH_2Cl_2$-EtOAc (50:1) to give 90 mg of the title compound as a mixture of geometric isomers.

$^1$H NMR ($CDCl_3$) δ: 0.07 (s, 6H), 0.92 (s, 9H), 1.87 (m, 2H), 2.73 (m, 2H), 3.65 (t, 2H), 3.87 (s, 3H), 6.71–8.74 (m, 7H).

Step B

Mitsunobu Reaction

Using the general procedure described in Example 2 and 180.6 mg (0.42 mmol) of phenol, prepared in Step A, 288.4 mg of the carbapenem was produced, as a mixture of geometric isomers.

$^1$H NMR ($CDCl_3$) δ: 0.04 (s, 6H), 0.89 & 0.90 (s's, 9H), 1.27 (2d's, 3H)), 1.43 (d, 6.5 Hz,3H), 1.86 (m, 2H), 2.73 (m, 2H), 3.44 (m, 1H-1 & 1H-6), 3.66 (m, 2H), 3.85 (s, 3H), 4.17 (2dd's, 1H-5), 5.12 (m, 1H-8), 5.45 (d, 1H), 5.71 (d, J=15 Hz, 1H), 6.69–8.74 (m, 7H).

Step C

Desilylation

Using the general procedure outlined in Example 21, the carbapenem (268.9 mg) prepared in the previous step provided 171.6 mg (75%) of carbapenem 56.

$^1$H NMR ($CDCl_3$) δ: 1.27 (d, J=7.3 Hz, 3H), 1.43 (d, J=6.3 Hz, 3H), 1.95 (m, 2H), 2.78 (m, 2H), 3.44 (m, 1H-1 & 1H-6), 3.67 (t, J=6.3 Hz, 2H), 3.86 (s, 3H), 4.21 (dd, 1H-5), 5.12 (m, 1H-8), 5.45 (d, 1H), 5.7 (d, 1H), 6.72–8.77 (m, 7H).

EXAMPLE 61

Preparation of Carbapenem 57

Step A

Triflate Formation

Using the general procedure outlined in Step A of Example 10, 48.4 mg (0.074 mmol) of alcohol 56, prepared in Example 60, was converted into 65.6 mg of the corresponding triflate.

Step B

Displacement Reaction

Using the general procedure outlined in Step B of Example 10, the crude triflate from Step A was converted into 78 mg of crude carbapenem 58, which was used without further purification.

EXAMPLE 62

Preparation of Carbapenem 58

Using the general procedure outlined in Step C of Example 7, the crude carbapenem salt 57 was converted into 17.9 mg of carbapenem 58, after resin chromatography on amberchrom CG 161.

IR (nujol): 1751, 1699, 1584 $cm^{-1}$;

$^1$H NMR ($D_2O$—$CD_3CN$,5:2) δ: 1.09 (m), 1.5 (m, 6H), 1.65 (m), 2.94 (m, 2H), 3.56 (m, 1H-1 & 1H-6), 3.83 (m), 4.11 (s, 3H), 4.2 (m), 4.45 (m), 5.07 (d, J=13.6 Hz,1H), 5.88 (d, J=13.6 Hz,1H), 7.3–8.69(m, 7H);

UV: $\lambda_{max}$ 330, 266 nm($H_2O$).

EXAMPLE 63

Preparation of Carbapenem 59

Using the procedure described in Example 22, 70.2 mg (0.011 mmol) of carbapenem 56 provided 68.4 mg of salt 59.

$^1$H NMR ($CDCl_3$) δ: 1.28 (m, 3H), 1.44 (m, 3H), 2.25 (m, 2H), 2.72 (m, 2H), 3.44 (m, 1H-1 & 1H-6), 3.87 (s, 3H), 3.93 (s, N—$CH_3$), 4.2 (m, 2H), 5.13 (m, 1H-8), 6.73–9.16 (m, 9H).

EXAMPLE 64

Preparation of Carbapenem 60

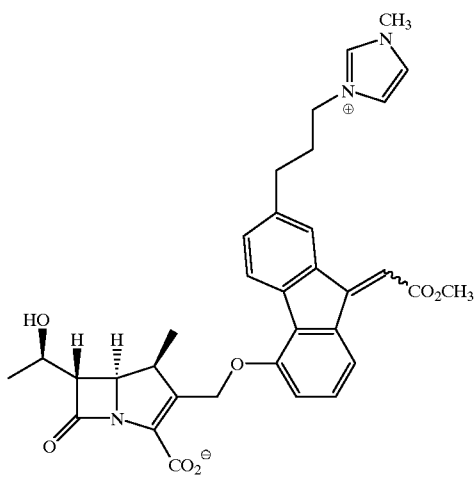

Following the procedure outlined in Example 3, the carbapenem 59 prepared in Example 64 was deallylated to provide 31.3 mg of 60 after purification by reverse phase chromatography (RP-PLC) using water-acetonitrile (7:3) as the eluant and lyophilization.

IR (nujol): 1753, 1715, 1587 cm$^{-1}$;

$^1$H NMR (D$_2$O—CD$_3$CN,5:2) δ: 1.44 (m,6H), 2.38 (m, 2H), 2.87 (m, 2H), 3.54 (m, 1H-1 & H-6), 4.00, 4.02, 4.07, 4.09 (s's, 6H), 4.45 (m, 4H), 5.09 (d, J=14 Hz, 1H), 5.88 (d, J=14 Hz, 1H), 7.28–8.84 (m, 9H).

UV: λ$_{max}$ 332, 268 nm(H$_2$O).

EXAMPLE 65

Preparation of Carbapenem 61

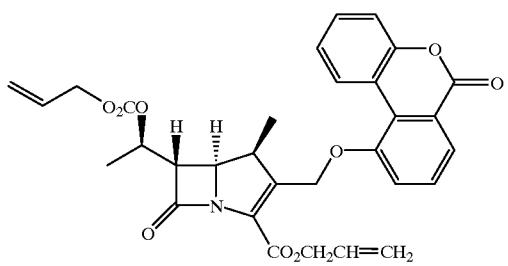

Step A

Preparation of methyl-2,2'-dimethoxy-biphenyl-6-carboxylate

Using the procedure outlined in Step A of Example 18, 201.7 mg (0.69 mmol) of methyl-2-iodo-3-methoxy-benzoate and 125.9 mg (0.82 mmol) of 2-methoxyphenylboronic acid gave after 27 hours of reflux a quantitative yield of the title substance.

$^1$H NMR (CDCl$_3$) δ: 3.56 (s, 3H), 3.71 (s, 3H), 3.73 (s, 3H), 6.95–7.47 (m, 7H).

Step B

Preparation of 2,2'-dimethoxy-biphenyl-6-carboxylic acid

A stirred mixture of 188.4 mg (0.69 mmol) of ester prepared in Step A and 0.28 mL (1.39 mmol) of 5N NaOH in 2 mL of ethanol was refluxed under nitrogen for 1.5 hours. The mixture was partitioned between EtOAc, ice, 2N HCl, and the organic phase was separated, washed with brine, dried over Na$_2$SO$_4$, filtered, evaporated, and dried in vacuo to give 171.6 mg of the title acid which was used without further purification.

$^1$H NMR (d$_6$-acetone) δ: 3.66 (s, 3H), 3.71 (s, 3H), 6.79–7.48 (m, 7H).

Step C

Preparation of 12-methoxy-3,4-benzocoumarin

To a stirred suspension of 171.6 mg (0.67 mmol) of acid prepared in Step B in 2 mL of sieve-dried CH$_2$Cl$_2$ at 0° C. was added all at once 173.1 mg (0.83 mmol) of phosphorous pentachloride and the mixture was stirred further for 5 minutes, and then for 1 hour with the ice-water bath removed. The homogeneous solution was recooled to 0° C., and 133 mg (0.99 mmol) of AlCl$_3$ was added all at once. The resulting mixture was stirred with the ice-water bath removed for 1 hour and then partitioned between EtOAc, ice, and brine. The organic phase was separated, washed with brine, dried over Na$_2$SO$_4$, filtered, evaporated, and dried in vacuo. Purification by PLC with hexanes-methylene chloride (2:1) provided 134.7 mg of the title compound.

$^1$H NMR (CDCl$_3$) δ: 3.99 (s, 3H), 7.21–8.87 (m, 7ArH).

Step D

Preparation of 12-Hydroxy-3,4-benzocoumarin

The methylether from Step C in 1 mL acetic acid and 3.4 mL 48% HBr was stirred at 130° C. for 5 hours. The cooled solution was treated with water and the insoluble product collected by filtration, washed well with water, and dried in vacuo to give 131.3 mg of the title product, which was used without further purification.

$^1$H NMR (d$_6$-acetone) δ: 7.33–9.16 (m, 7H), 9.97 (s, 1H).

Step E

Mitsunobu Reaction

Using the general procedure described in Example 2 and 53 mg (0.025 mmol) of phenol, prepared in Step D, 35.5 mg of carbapenem 61 was produced, which contained some of the C-3 isomer and was used without further purification.

EXAMPLE 66

Preparation of Carbapenem 62

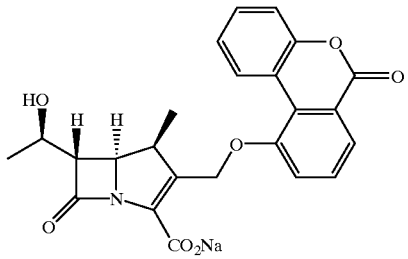

Using the procedure described in Example 3 and the material prepared in step E of the previous example, 6.6 mg of carbapenem 62 was produced after RP-PLC purification, elution with water-acetonitrile (4:1), and lyophilization.

IR (nujol): 1754, 1726, 1598 cm$^{-1}$;

$^1$H NMR (D$_2$O—CD$_3$CN,5:2) δ: 1.41 (d, J=7.2 Hz, 3H), 1.45 (d, J=6.3 Hz, 3H), 3.47 (m, 1H-1), 3.61 (dd, 1H-6), 4.34

(dd, 1H-5), 4.42 (m, 1H-8), 5.2 (d, J=13.5 Hz, 1H), 6.0 (d, J=13.5 Hz, 1H), 7.56–9.18 (m, 7ArH);

UV: $\lambda_{max}$ 332, 262 nm($H_2O$).

What is claimed is:

1. A compound represented by formula I:

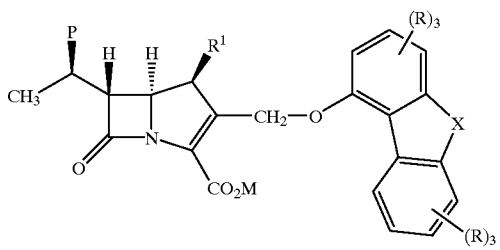

I or salt or hydrate thereof, wherein:

$R^1$ represents H or methyl;

$CO_2M$ represents a carboxylic acid, a carboxylate anion, or a pharmaceutically acceptable ester group, with the proviso that when $CO_2M$ represents a carboxylate anion, it is balanced by a positively charged R group or a positively charged $L^+$ provided that there are no more than two positively charged groups present;

P represents hydrogen, hydroxyl or F;

X is present or absent, when present, represents a members selected from the group consisting of: $CH_2$, $C(R)_2$, $C=CR_2$, O, $S(O)x$, with x equal to 0, 1 or 2; C(O); C(O)O, OC(O) and NR; and when X is absent a biphenyl group results;

each R group is independently selected from: hydrogen; halo; —CN; —$NO_2$; —$NR^aR^b$; —$OR^c$; —$SR^c$; —C(O)$NR^aR^b$; —C(O)$OR^h$; —S(O)$R^c$; —$SO_2R^c$; —$SO_2NR^aR^b$; —$NR^aSO_2R^b$; —C(O)$R^a$; —OC(O)$R^a$; —OC(O)$NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; —A—$(CH_2)_n$—Q and —$C_{3-7}$ cycloalkyl, unsubstituted or substituted with one to four $R^d$ groups;

A represents O, S or —$CH_2$—;

n represents an integer from 0–3;

each $R^a$, $R^b$ and $R^c$ independently represents hydrogen, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; $NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$ or —$NR^eC(NR^f)R^g$;

$R^e$, $R^f$ and $R^g$ represent hydrogen; —$C_{1-6}$ straight- or branched-chain alkyl unsubstituted or substituted with one to four groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$-$C_6$ cycloalkyl group or phenyl, or when two $R^h$ groups are present Q is selected from the group consisting of:

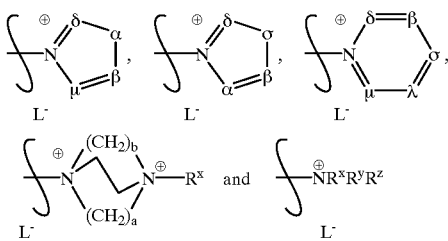

wherein:

a and b are 1, 2 or 3;

$L^-$ is one or more pharmaceutically acceptable negative counterions and can be present or absent as appropriate to maintain the appropriate charge balance;

α represents O, S or $N^+R^s$;

β, δ, λ, μ and σ represent $CR^t$, N or $N^+R^s$, provided that no more than one of β, δ, λ, μ and σ is $N^+R^s$;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR''R^v$; —$OR''$; —$SR''$; —$CONR''R^v$; —$COOR^h$; —$SOR''$; —$SO_2R''$; —$SO_2NR''R^v$; —$NR''SO_2R^v$; —$COR''$; —$NR''COR^v$; —$OCOR''$; —$OCONR''R^v$; —$NR''CO_2R^v$; —$NR''CONR^vR^w$; —$OCO_2R^v$; —$C_{1-6}$ straight- or branched-chain alkyl, unsubstituted or substituted with one to four $R^i$ groups;

$R''$ and $R^v$ represent hydrogen or —$C_{1-6}$ straight- or branched-chain alkyl, unsubstituted or substituted with one to four $R^i$ groups;

each $R^w$ independently represents hydrogen; —$C_{1-6}$ straight- or branched-chain alkyl, unsubstituted or substituted with on to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight-or branched-chain alkyl groups, said alkyl groups being unsubstituted or substituted with one to four $R^i$ groups; and $R^Y$ and $R^Z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—.

2. A compound in accordance with claim 1 wherein $R^1$ represents methyl.

3. A compound in accordance with claim 1 wherein $CO_2M$ represents a carboxylic acid or a carboxylate anion.

4. A method of treating or preventing a bacterial infection in a mammalian patient in need of such therapy, comprising administering to said patient an anti-infective amount of a compound as defined in claim 1.

5. A compound in accordance with claim 1 wherein one R group represents —A—(CH$_2$)$_n$—Q, and A, n and Q are as originally defined.

6. A compound in accordance with claim 5 wherein A represents —CH$_2$—.

7. A compound in accordance with claim 5 wherein n represents 0 or 1.

8. A compound in accordance with claim 5, wherein Q is

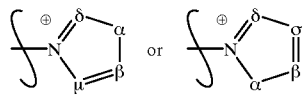

wherein:

α represents O, S or NR$^s$;

β, δ, λ, μ and σ repressent CR$^t$, N or N$^+$R$^s$, provided that no more than one of β, δ, λ, μ and σ is N$^+$R$^s$, balanced by L$^-$ or CO$_2$M, and R$^s$ is as originally defined.

9. A compound in accordance with claim 5 wherein Q is selected from the group consisting of:

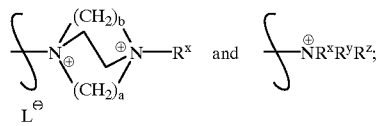

a and b are 2;

L$^-$ is a pharmaceutically acceptable counterion;

and R$^x$, R$^y$ and R$^z$ are as originally defined.

10. A compound in accordance with claim 9 wherein Q is

{N(⊕)—(CH$_2$)$_b$—N(⊕)—R$^x$, (CH$_2$)$_a$, L$^⊖$}.

11. A compound in accordance with claim 5, wherein Q is

{N(⊕)—δ═β, μ—λ—O} wherein:

β, δ, λ, μ and σ represent CR$^t$, N or N$^+$R$^s$, provide that no more than one of β, δ, λ, μ and σ is N$^+$R$^s$, balanced by L$^-$ or CO$_2$M, and all other variables are as originally defined.

12. A compound in accordance with claim 1 falling within the following table:

TABLE 1

| Cpd No. | Compound |
|---------|----------|
| 2 | allylO$_2$CO—[β-lactam structure with dibenzothiophene]—CO$_2$allyl |
| 3 | HO—[β-lactam structure with dibenzothiophene]—CO$_2^-$[M] L$^+$ |

TABLE 1-continued
| Cpd No. | Compound |
|---|---|
| 4 | 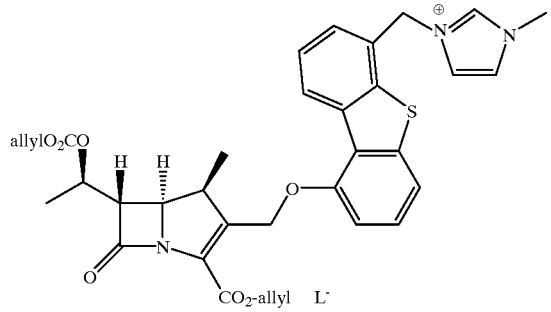 |
| 5 | 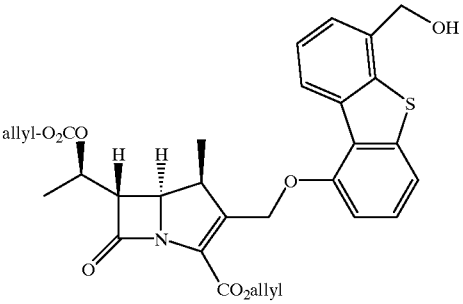 |
| 6 | 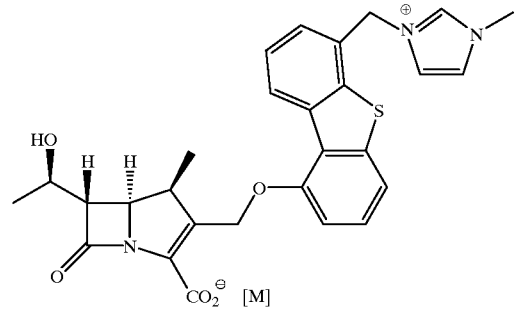 |
| 7 | 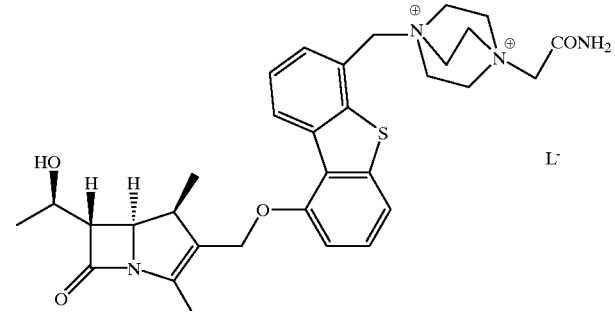 |

TABLE 1-continued

| Cpd No. | Compound |
| --- | --- |
| 8 | |
| 9 | |
| 10 | |
| 11 | |

TABLE 1-continued
| Cpd No. | Compound |
|---|---|
| 12 | 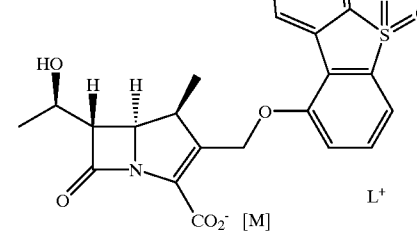 |
| 13 | 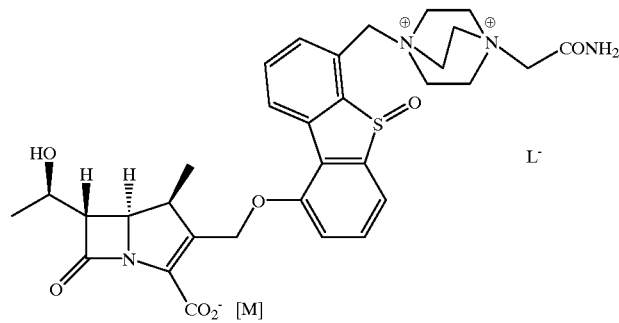 |
| 14 | 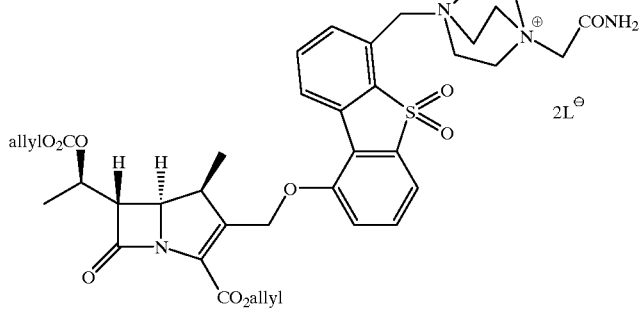 |
| 15 | 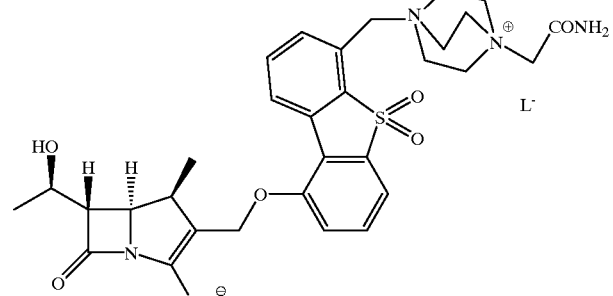 |

TABLE 1-continued
| Cpd No. | Compound |
|---|---|
| 16 | 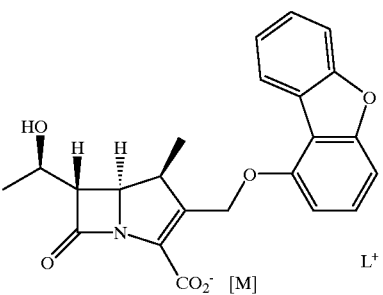 |
| 17 | 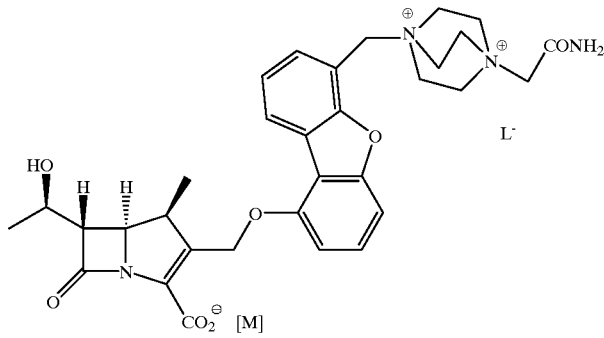 |
| 18 | 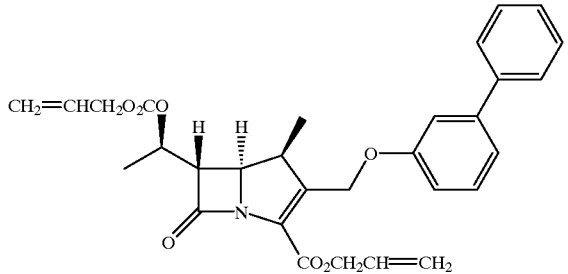 |
| 19 | 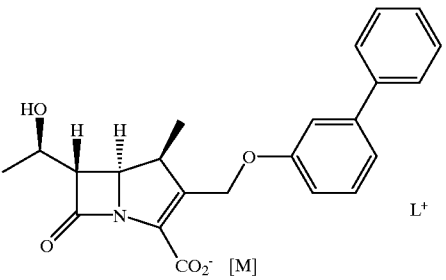 |
| 21 | 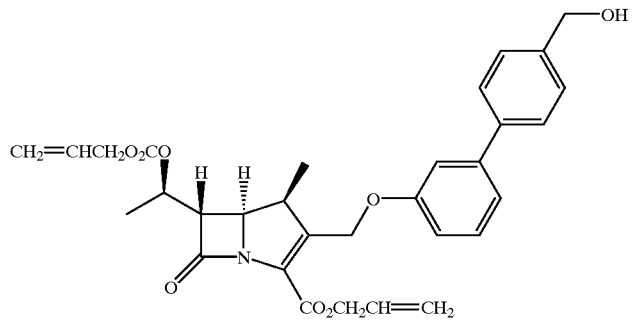 |

TABLE 1-continued

| Cpd No. | Compound |
|---------|----------|
| 22 | (carbapenem structure with 6-(1-allyloxycarbonyloxyethyl) group, 4-methyl, 3-[(3-(4-(N-methylimidazolium-1-ylmethyl)phenyl)phenoxy)methyl], allyl ester; L⁻ counterion) |
| 23 | (carbapenem structure with 6-(1-hydroxyethyl), 4-methyl, 3-[(3-(4-(3-methylimidazolium-1-yl)phenyl)phenoxy)methyl], CO₂⁻ [M]) |
| 24 | (carbapenem structure with 6-(1-allyloxycarbonyloxyethyl), 4-methyl, 3-[(9-oxofluoren-4-yloxy)methyl], allyl ester) |
| 25 | (carbapenem structure with 6-(1-hydroxyethyl), 4-methyl, 3-[(9-oxofluoren-4-yloxy)methyl], CO₂⁻ [M]; L⁺) |

TABLE 1-continued
| Cpd No. | Compound |
|---|---|
| 26 | 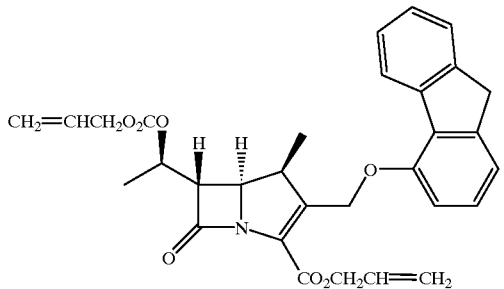 |
| 27 | 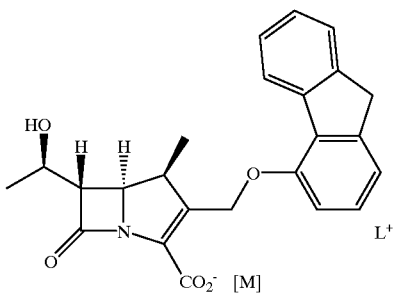 |
| 28 | 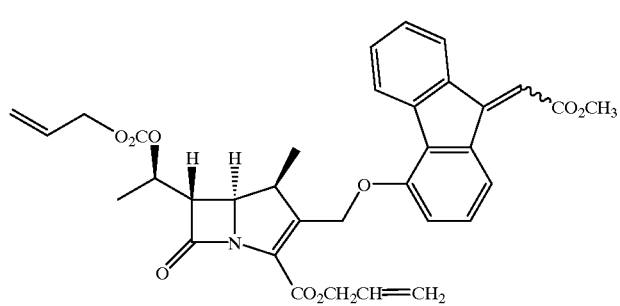 |
| 29 | 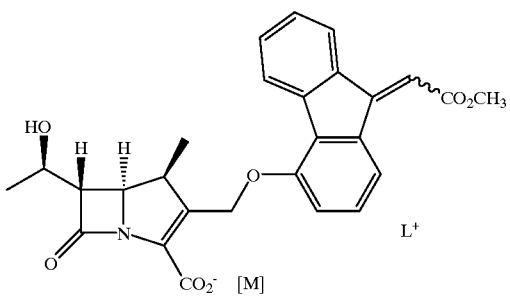 |
| 30 | 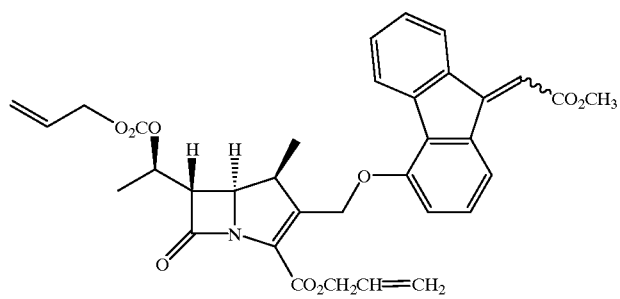 |

TABLE 1-continued
| Cpd No. | Compound |
|---|---|
| 31 | 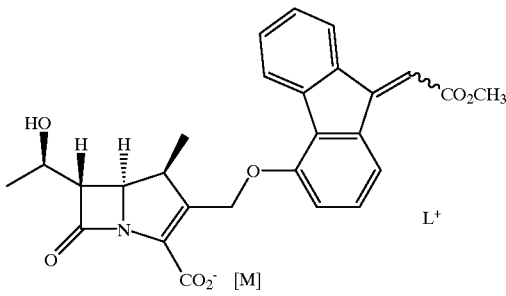 |
| 33 | 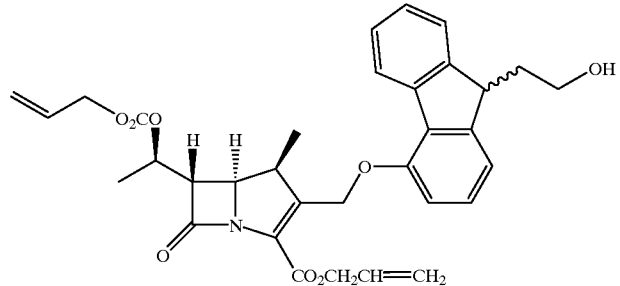 |
| 34 | 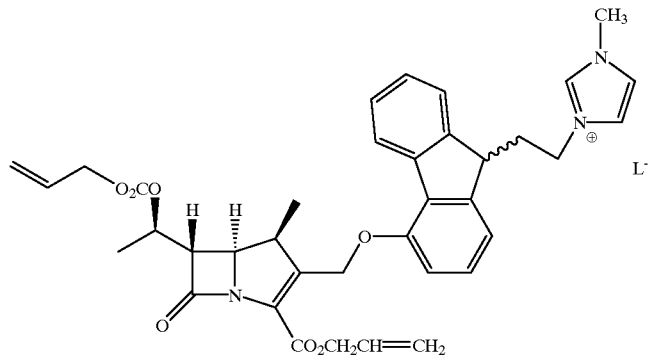 |
| 35 | 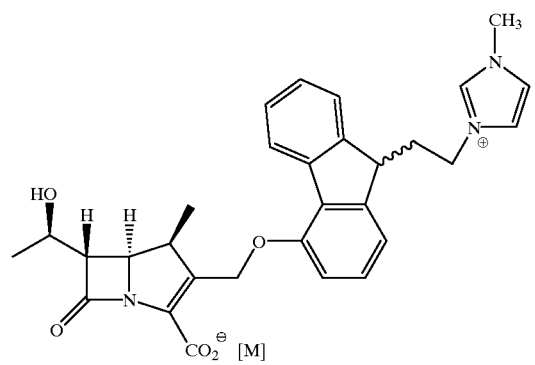 |

TABLE 1-continued
| Cpd No. | Compound |
|---|---|
| 36 | 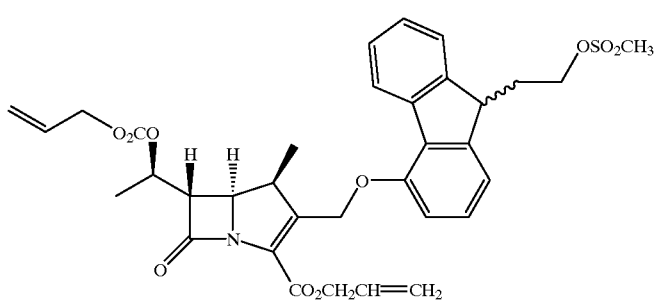 |
| 38 | 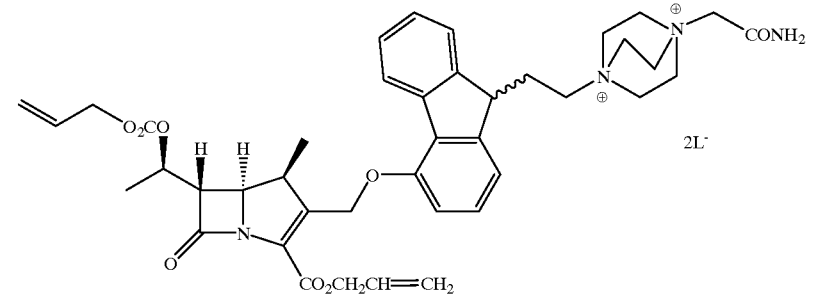 |
| 39 | 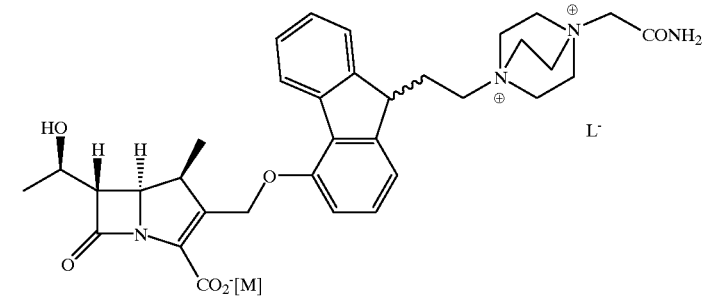 |
| 41 | 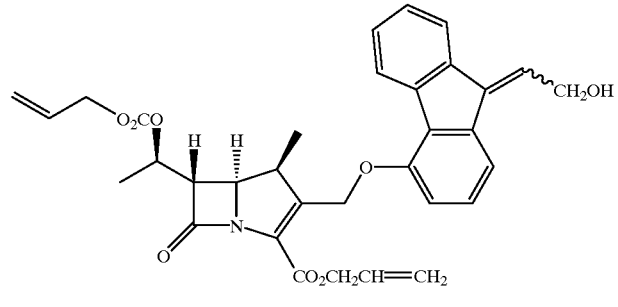 |
| 42 | 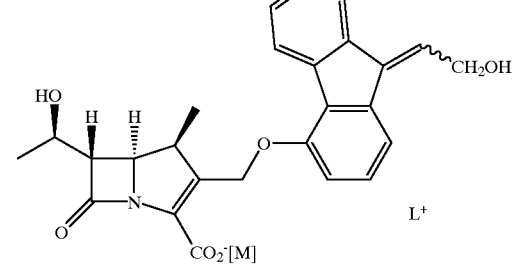 |

TABLE 1-continued
| Cpd No. | Compound |
|---|---|
| 44 | 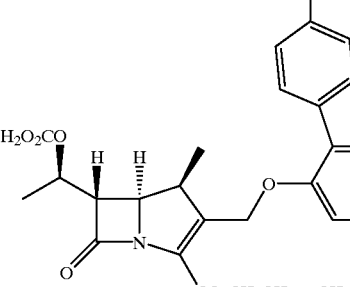 |
| 45 | 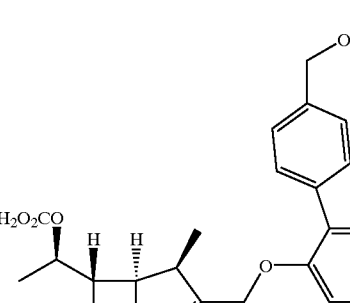 |
| 47 | 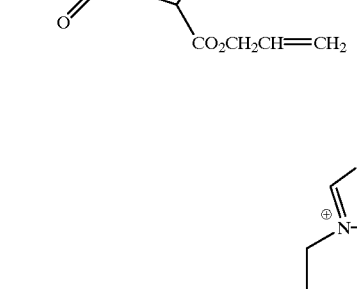 |

TABLE 1-continued
| Cpd No. | Compound |
| --- | --- |
| 48 | 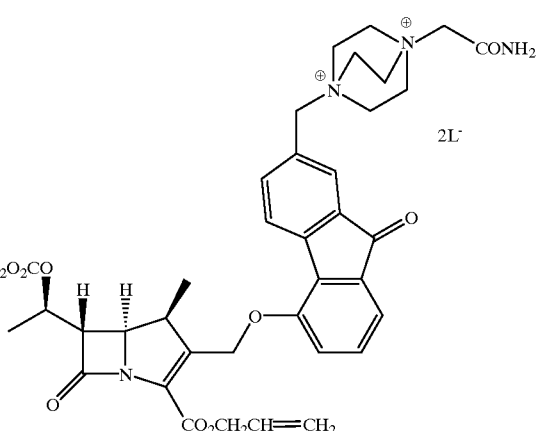 |
| 49 | 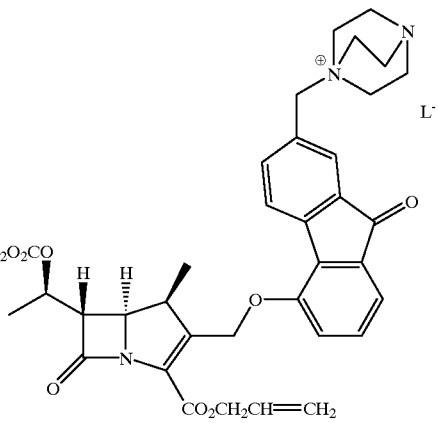 |
| 50 | 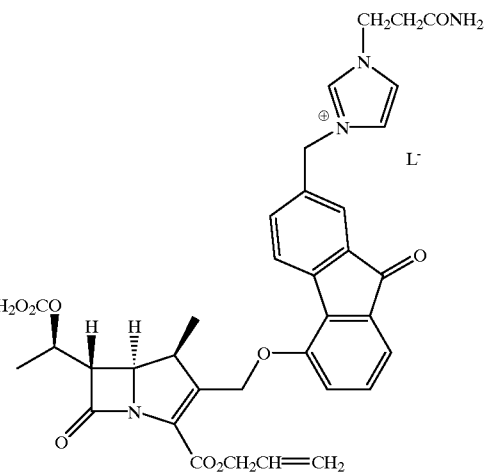 |

TABLE 1-continued
| Cpd No. | Compound |
|---|---|
| 51 | 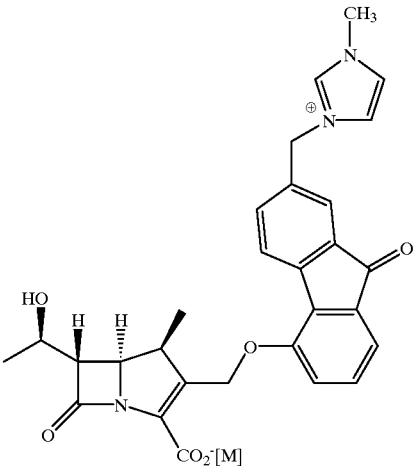 |
| 52 | 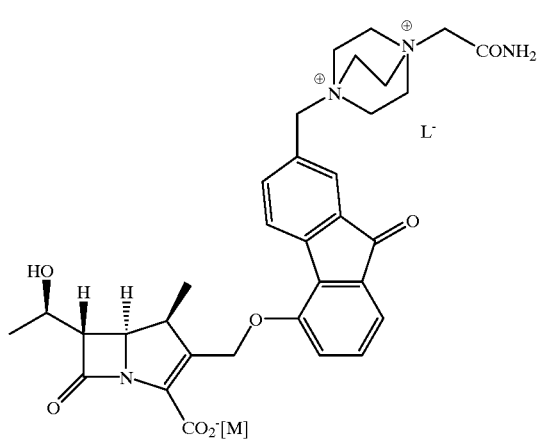 |
| 53 | 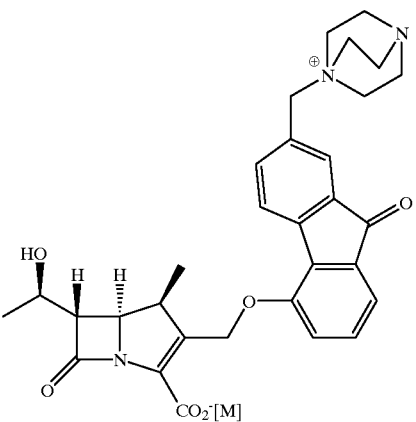 |

TABLE 1-continued
| Cpd No. | Compound |
|---|---|
| 54 | 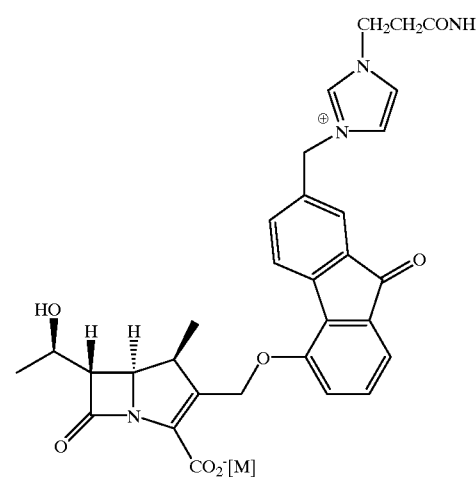 |
| 55 | 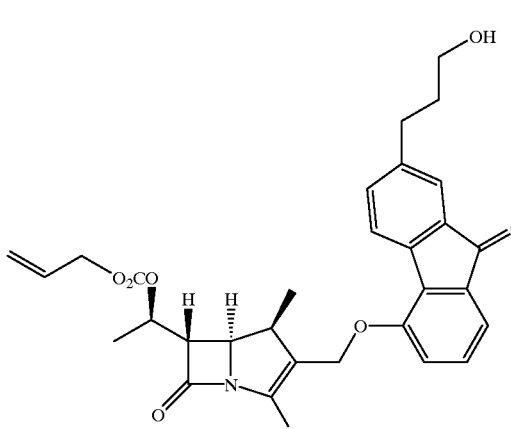 |
| 56 | 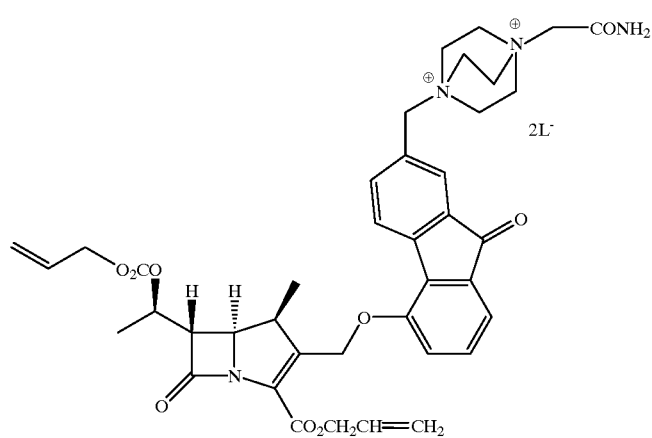 |

TABLE 1-continued
| Cpd No. | Compound |
|---|---|
| 57 | 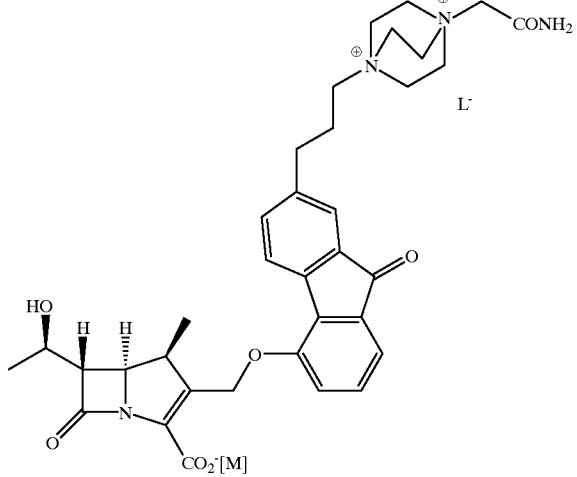 |
| 58 | 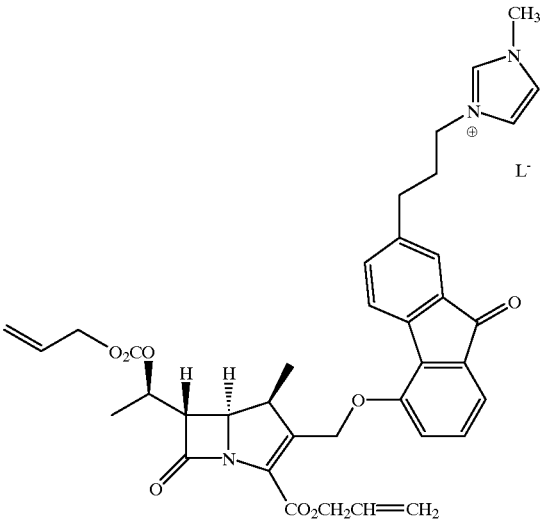 |
| 59 | 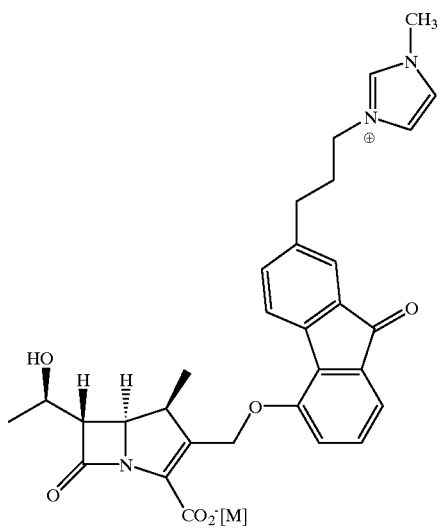 |

TABLE 1-continued
| Cpd No. | Compound |
| --- | --- |
| 60 | 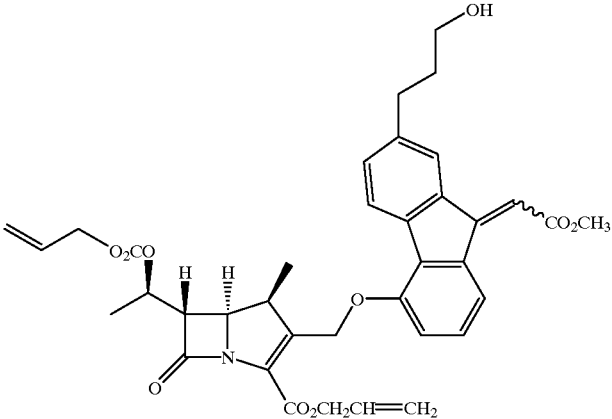 |
| 61 | 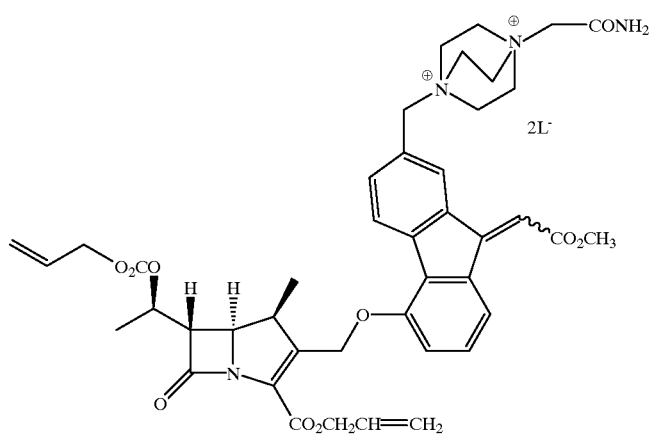 |
| 62 | 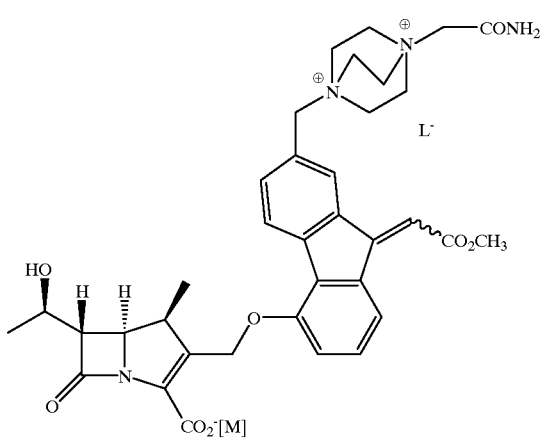 |

TABLE 1-continued

| Cpd No. | Compound |
| --- | --- |
| 63 | |
| 64 | |
| 65 | |

TABLE 1-continued

| Cpd No. | Compound |
|---|---|
| 66 | 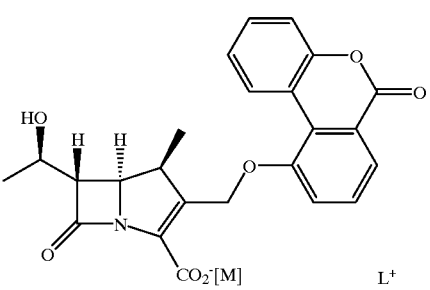 | wherein $L^+$ and $L^-$ represent appropriately charged counterions.

13. A pharmaceutical composition which is comprised of a compound in accordance with claim 1, or a pharmaceutically acceptable salt or hydrate thereof, in combination with a pharmaceutically acceptable carrier.

14. A pharmaceutical composition in accordance with claim 12 further comprised of a compound which inhibits dehydropeptidase.

* * * * *